(12) United States Patent
Stray et al.

(10) Patent No.: US 10,309,959 B2
(45) Date of Patent: *Jun. 4, 2019

(54) CHARGED REACTIVE OLIGOMERS

(71) Applicant: Life Technologies Corporation, Carlsbad, CA (US)

(72) Inventors: James Stray, San Mateo, CA (US); Shaheer H. Khan, Foster City, CA (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/532,271

(22) PCT Filed: Dec. 3, 2015

(86) PCT No.: PCT/US2015/063791
§ 371 (c)(1),
(2) Date: Jun. 1, 2017

(87) PCT Pub. No.: WO2016/090165
PCT Pub. Date: Jun. 9, 2016

(65) Prior Publication Data
US 2018/0031545 A1   Feb. 1, 2018

Related U.S. Application Data

(60) Provisional application No. 62/087,208, filed on Dec. 3, 2014, provisional application No. 62/087,034, filed on Dec. 3, 2014.

(51) Int. Cl.
| | | |
|---|---|---|
| *G01N 33/53* | (2006.01) | |
| *G01N 33/533* | (2006.01) | |
| *C12Q 1/6876* | (2018.01) | |
| *C12Q 1/40* | (2006.01) | |
| *G01N 33/58* | (2006.01) | |
| *G01N 27/447* | (2006.01) | |
| *G16C 20/90* | (2019.01) | |
| *G01N 30/00* | (2006.01) | |
| *G01N 33/66* | (2006.01) | |
| *G16C 99/00* | (2019.01) | |
| *G01N 30/34* | (2006.01) | |
| *G01N 30/88* | (2006.01) | |

(52) U.S. Cl.
CPC .......... *G01N 33/5308* (2013.01); *C12Q 1/40* (2013.01); *C12Q 1/6876* (2013.01); *G01N 27/44726* (2013.01); *G01N 30/00* (2013.01); *G01N 33/533* (2013.01); *G01N 33/58* (2013.01); *G01N 33/582* (2013.01); *G01N 33/66* (2013.01); *G16C 20/90* (2019.02); *G16C 99/00* (2019.02); *G01N 27/447* (2013.01); *G01N 30/34* (2013.01); *G01N 2030/8813* (2013.01); *G01N 2030/8836* (2013.01); *G01N 2333/924* (2013.01); *G01N 2400/00* (2013.01); *G01N 2400/22* (2013.01); *G01N 2458/10* (2013.01); *G01N 2800/26* (2013.01)

(58) Field of Classification Search
CPC ........ G01N 33/5308; C12Q 1/40; C12Q 1/68; C12P 21/005
See application file for complete search history.

(56) References Cited

U.S. PATENT DOCUMENTS

| | | |
|---|---|---|
| 5,140,104 A | 8/1992 | Coughlin et al. |
| 5,521,290 A | 5/1996 | Sivam et al. |
| 5,633,351 A | 5/1997 | Reed |
| 7,351,544 B2 * | 4/2008 | Pierce .................. C12Q 1/6804 435/6.14 |
| 2002/0197614 A1 | 12/2002 | Weir et al. |
| 2010/0145032 A1 | 6/2010 | Laine et al. |
| 2012/0231961 A1 | 9/2012 | La et al. |

FOREIGN PATENT DOCUMENTS

| | | |
|---|---|---|
| HU | 189204 B | 6/1986 |
| WO | WO-8706837 A1 | 11/1987 |
| WO | WO 2013/025527 * | 2/2013 |
| WO | WO-2013173494 A1 | 11/2013 |

OTHER PUBLICATIONS

Ruhak et al, Glycan labeling strategies and their use in identification and quantification, 2010, Anal Bioanal Chem, 397:3457-3481 (Year: 2010).*
Kwon et al, Signal Amplification by Glyco-qPCR for Ultrasensitive Detection of Carbohydrates: Applications in Glycobiology, 2012, Angew. Chem. Int. Ed., 51, 11800-11804 (Year: 2012).*
Database Caplus,, "Cholecystokinin octapeptide sulfate ester and its salts", Chemical Abstracts Service Columbus Ohio Feb. 4, 1989.
Database Caplus,, "L-Aspartic acid, N-[(9H-fluoren-9-ylmethoxy)carbonyl]-, 1-hydrazide, mono(trifluoroacetate)", Chemical Abstracts Service, Columbus, Ohio, Dec. 17, 1984.
Database Caplus,, "Preparation of antibody conjugates of amine derivatives of folic acid analogs", Chemical Abstracts Service, Columbus, Ohio, Jan. 13, 1998.
Database Registry,, "L-Giutamic acid, N-[4-[[(2, 4-diamino-6-pteridinyl) methyl] amino] benzoyll-, 1-hydrazide", Chemical Abstracts Service Columbus Ohio Jan. 13, 1989.
International Search Report and Written Opinion for Application No. PCT/US2015/063791, dated May 3, 2016, 17 pages.
International Search Report and Written Opinion for International Application No. PCT/US2015/063593, dated Jun. 27, 2016, 17 pages.
Kuo-Ting Huang et al: "Combinatorial Self-Assembly of Glycan Fragments into Microarrays", Chembiochem—A European Journal of Chemical Biology., vol. 12, No. 1, Jan. 3, 2011 (Jan. 3, 2011), pp. 56-60.
Leteux, C. et al., "Biotinyi-L-3(2-naphthyl)-alanine hydrazide derivatives of N-glycans: versatile solid-phase probes for carbohydrate-recognition studies", Glycobiology, vol. 8, No. 3, 1998, 227-236.

\* cited by examiner

*Primary Examiner* — Narayan K Bhat

(57) ABSTRACT

Methods, systems, compositions and kits are described for detecting cleaved glycans from a glycoconjugate. After labeling the glycan with a nucleic acid charged oligomer described herein, the labeled glycans can be separated under the influence of an electric field or based on their detectable tag and identified.

11 Claims, 26 Drawing Sheets

Reducing End Conjugation of Glycans

SANH Linker

SHNH Linker

SHTH Linker

Linkers for Glycan Conjugation

Dye-T-G-A-C-T-Hydrazine-Glycan

Dye-T-G-A-C-T-Hydrazine-Glycan

Dye-T-G-A-C-T-SANH

Dye-T-G-A-C-T-Hydrazine-Glycan

2<m<40

CHARGED REACTIVE OLIGOMERS

CROSS REFERENCE

This application claims benefit to U.S. Provisional Application 62/087,208, filed on Dec. 3, 2014, the disclosure of which is each hereby incorporated by reference in its entirety for all purposes.

A PCT application entitled "Hydrazinyl and Aminooxy Compounds and Their Methods of Use", filed on even Dec. 3, 2015, which claims the benefit to U.S. Provisional Application 62/087,034, filed on Dec. 3, 2014, entitled "Hydrazinyl Compounds and Their Methods of Use", the disclosure of which is each hereby incorporated by reference in its entirety for all purposes.

BACKGROUND

Carbohydrates or glycans linked to the surface of proteins play an important role by ensuring correct cellular and protein function and mediating protein folding, signaling, and other important cellular systems. The analysis of glycans is challenging, however, and involves time consuming sample preparation and complex, low-throughput analytical techniques. There is a need for new and improved apparatuses, methods, and computer program products that efficiently and simply allow the performance of hi-throughput analysis of glycans while retaining sufficient resolution and sensitivity. Such a need is especially applicable in numerous fields, including in academic and industrial research and in bioproduction and pharmaceutical industries, for example, where large numbers of glycans need to be analyzed rapidly and efficiently.

The challenge facing the carbohydrate analyst is formidable. Unlike proteins and DNA, where molecular structure is determined by the linear sequence of amino acids or nucleotide bases, carbohydrates are branched and have additional variable features. The fundamental data required to fully characterize a carbohydrate structure are the monosaccharide composition, the order, number, configuration, and ring form of the saccharide residues found in the glycan cleaved from the glycoconjugate, including the position and character of any substituent groups on any residue, the positions of the interresidue linkages including any branching points, and the configuration of the glycosidic linkages. Improved workflows and increased selectivity of glycan cleavage, modification and detection are needed.

Various patents, patent applications, and other publications are referred to herein, all of which are incorporated herein in their entireties by reference. In addition, the following standard reference works are incorporated herein by reference: Current Protocols in Molecular Biology, John Wiley & Sons, N.Y., edition as of October 2007; Sambrook, Russell, and Sambrook, Molecular Cloning: A Laboratory Manual, 3rd ed., Cold Spring Harbor Laboratory Press, Cold Spring Harbor, 2001. In the event of a conflict between the instant specification and any document incorporated by reference, the specification shall control, it being understood that the determination of whether a conflict or inconsistency exists is within the discretion of the inventors and can be made at any time.

Additional features and advantages of the present teachings will be evident from the description that follows, and in part will be apparent from the description, or can be learned by practice of the present teachings. It is to be understood that both the foregoing summary and the following detailed description are exemplary and explanatory only and are intended to provide further explanation of the present teachings without limiting the present teachings.

SUMMARY OF THE INVENTION

In certain embodiments, a method of labeling a glycan on a biomolecule is provided, comprising:
(a) cleaving the glycan from the biomolecule generating a cleaved glycan; and
(b) labeling the cleaved glycan with a nucleic acid oligomer to form a nucleic acid-charged glycan;
wherein the nucleic acid oligomer comprises:
i) a first site comprising an intrinsic charge and a reactive moiety, wherein the reactive moiety enables attachment of the nucleic acid oligomer to the glycan; and
ii) optionally, a second site comprising a detectable tag.

In certain embodiments the method of labeling the glycan further comprises detecting the nucleic acid-charged glycan.

In certain embodiments the cleaved glycan of step (a) is separated in a charge differential field to generate a charged glycan.

In certain embodiments the nucleic acid-charged glycan of step (b) is separated in a charge differential field and is identified by a hybridization step.

In certain embodiments the charge differential field comprises an electric field, a magnetic field, a salt gradient, or a combination thereof.

In certain embodiments the charged glycan has a negative charge.

In certain embodiments the biomolecule is selected from the group consisting of a glycoprotein, a glycolipid, a proteoglycan, a phosphoprotein, a glycosaminoglycan, a phospholipid-protein containing a glycan core, a synthetic glycan, a native glycan, a derivatized glycan, and a combination thereof.

In certain embodiments the glycan as described above has a nucleic acid oligomer that comprises 1 to 20 nucleotides. In other embodiments the nucleic acid oligomer is selected from the group consisting of 1 to 5 nucleotides, 1 to 8 nucleotides, 1 to 10 nucleotides, 1 to 15 nucleotides and 1 to 2 nucleotides.

In certain embodiments the nucleic acid oligomer comprises a deoxyribonucleic acid or analogs thereof, a ribonucleic acid or analogs thereof, a locked nucleic acid (LNA) or analogs thereof, a protein nucleic acid (PNA), a nucleic acid with a phosphorothionate linkage, or a combination thereof. In certain embodiments the first site comprises at least one of a nucleotide base, a 2' sugar, a 3' sugar, or a 5' sugar. In certain embodiments the reactive moiety comprises a protected group, an activatable group, an unprotected group, or a combination thereof. In certain embodiments, optionally, a mobility modifier is attached to the nucleic acid oligomer.

In certain embodiments the detection comprises UV absorbance, fluorescence, visible light, magnetic resonance, chemiluminescence, conductance, an electrical signal, a secondary biological reaction product, or a combination thereof.

In certain embodiments the detectable tag is selected from the group consisting of a radioactive tag, a dye, a fluorescent quencher, a nanocrystal, a spin label, a semiconductor, a biological reporter molecule, and a combination thereof.

In certain embodiments the dye comprises an optically detectable dye, and in other embodiments the optically detectable dye comprises a chemiluminescent dye, a fluorescent dye, or a combination thereof.

In certain embodiments the fluorescent dye is selected from the group consisting of a pyrene dye, a polymer dye, a xanthene dye, cyanine dye, a coumarin dye, a hydrazinyl substituent, a borapolyazaindacine dye, a benzofuran dye, an indole dye, and combinations thereof. In certain embodiments the fluorescent dye comprises a fluorescein, a rhodamine, a d-rhodamine group or a combination thereof. In certain embodiments the fluorescein dye comprises FAM™, JOE™, VIC™, HEX™, TET™, NED™, PET®, or a combination thereof. In certain embodiments the rhodamine comprises TAMRA™, ROX™, R110, R6G, Texas Red®, or a combination thereof. In certain embodiments the dye comprises aminopyrene trisulfonic acid (APTS), NBD, BigDye™, or a tautomer or salt thereof.

In certain embodiments the dye containing a hydrazinyl substituent includes but is not limited to sulfonate, phosphate, phosphonate, and carboxylate groups, or their derivatives. The dyes described above and particularly below may be used to detect a glycan, or to determine a glycan sequence, or can be used in methods employed thereof, or in methods for generating a glycan database, or for labeling a target analyte, for making a labeled, dextran size ladder, or in methods to increase the net charge of an analyte, or in methods used for propelling an analyte in an electric field, or in glycan sequencing kits, or in glycan detection kits, in glycan detection systems, or for making a dye labeled nucleic acid oligomer described above, that is reactive and can attach to a glycan.

In certain embodiments the dye is selected from the group consisting of:
(1) a compound of Formula (I) or a tautomer or salt thereof:

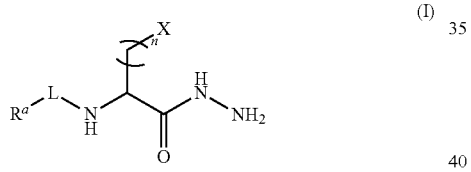

(I)

wherein,
L is a linker;
$R^a$ is a reporter molecule, carrier molecule or a solid support;
n is an integer from 1 to 24; and
X is a molecule containing $SO_3H$, $SO_3^-$, $OPO_3^{2-}$, $OPO_3H_2$, $PO_3H_2$, $PO_3^{2-}$, COOH, or $COO^-$.
or the following compounds:

Compound 1

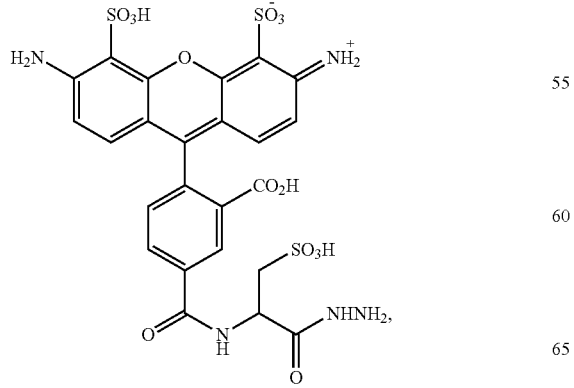

Compound 2

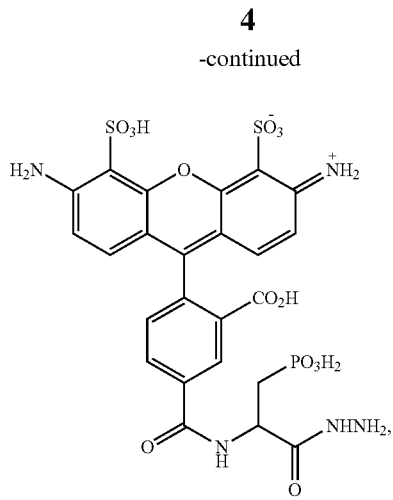

Compound 3

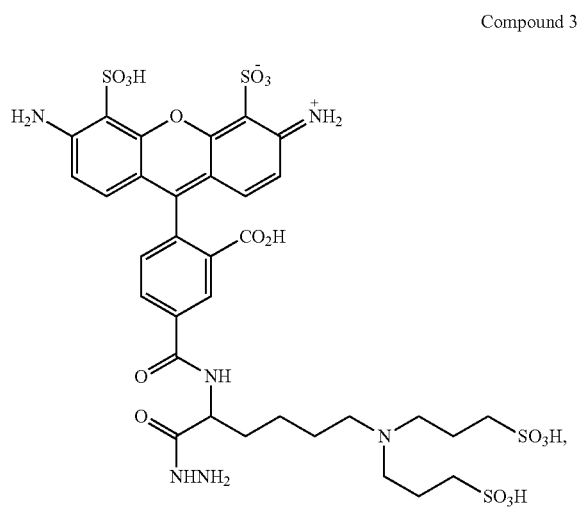

Compound 4

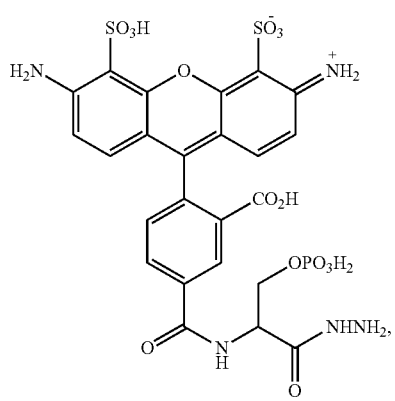

-continued

Compound 5

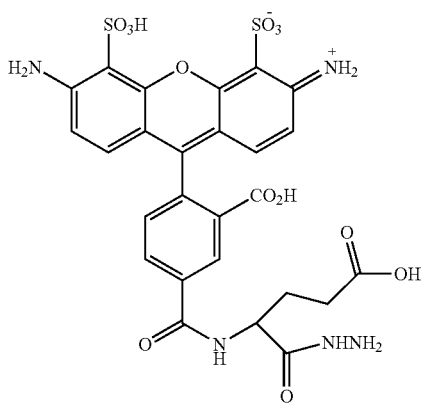

Compound 6

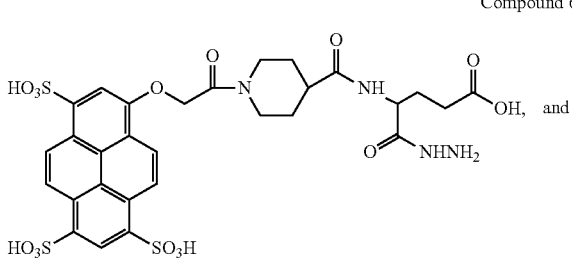
and

Compoud 30

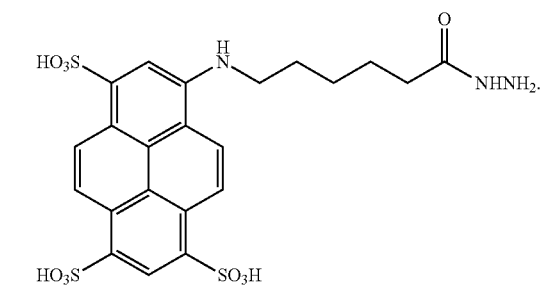

In certain embodiments the cleaving step (a) comprises enzyme hydrolysis, chemical hydrolysis, heat hydrolysis, or a combination thereof.

In certain embodiments the enzyme comprises an endoglycosidase, an exoglycosidase, or a combination thereof. In certain embodiments the endoglycosidase is selected from the group consisting of PNGase (peptide-N4-N-acetyl-beta-glucosaminyl asparagine amidase), endoglycosidase F, endoglycosidase F1, endoglycosidase F2, endoglycosidase F3, endoglycosidase H, endoglycosidase S, endoglycosidase D, α-neuraminidase, α-L-fucosidase, α-mannosidase, β-galactosidase, β-N-acetylglucosaminidase and β-mannosidase.

In certain embodiments the reactive moiety comprises an oxime, a hydrazide, a hydrazine, a sulfahydryl, a phosphine, an aldehyde, an aminooxy, an azide, an alkyne, an amine, or a combination thereof.

In certain embodiments a method for detecting a glycan on a biomolecule is provided, comprising: (a) cleaving the glycan from the biomolecule generating a cleaved glycan; (b) labeling the cleaved glycan with a mobility modifier to form a charged glycan; and (c) detecting the charged glycan, wherein the mobility modifier comprises: i) a first site comprising an intrinsic charge and a reactive moiety, wherein the reactive moiety enables attachment of the nucleic acid oligomer to the glycan; and ii) optionally, a second site comprising a detectable tag.

In certain embodiments, the mobility modifier comprises a polyethylene oxide chain, a linear or branched hydrophilic chain, a linear or branched hydrophobic chain, a linear or branched amphiphillic chain, a hexyl linker, a polypeptide chain, a polyamide chain, or a combination thereof.

In certain embodiments, the detectable tag comprises a radioactive tag, a dye, a fluorescent quencher, a nanocrystal, a spin label, a semiconductor, a biological reporter molecule, or a combination thereof.

In certain embodiments, a method of determining a glycan sequence is provided, comprising:
(a) separating a glycan from a cleaved glycan pool;
(b) labeling the glycan with a nucleic acid oligomer to generate a nucleic acid labeled glycan;
(c) making a plurality of aliquots of the nucleic acid labeled glycan and treating each aliquot with a distinct enzyme mixture generating an enzyme-treated aliquot with a variable, truncated glycan in each aliquot, wherein each distinct enzyme mixture comprises at least one, different, linkage-specific exoglycosidase enzyme;
(d) resolving the plurality of variable, truncated glycans from step (c) by a suitable separation means, to generate a first set of characteristic mobility shift profiles;
(e) optionally, sequentially repeating the enzyme treatment of one or more selected, enzyme-treated aliquot (s) of step (c) with a plurality of distinct enzyme mixtures, until the truncated glycan can no longer be digested, wherein each enzyme treatment generates a plurality of characteristic mobility shift profiles; and
(f) determining the glycan sequence by analyzing the sequential and characteristic mobility shift profiles and mapping the profiles to the linkage-specific exoglycosidases used during enzyme digestion,
wherein the nucleic acid oligomer comprises:
i) an intrinsic charge and a reactive moiety at a first site that enables attachment to the glycan; and
ii) optionally, a detectable tag at a second site on the nucleic acid oligomer.

In certain embodiments, the cleaved glycan pool is obtained by cleaving the glycans from a glycoprotein, a glycolipid, a proteoglycan, a phosphoprotein, a glycosaminoglycan, a glycan core containing phospholipid-protein, a synthetic glycan, a native glycan, a derivatized glycan, or a combination thereof.

In certain embodiments, the nucleic acid oligomer comprises 1 to 20 nucleotides. In other embodiments, the nucleic acid oligomer is selected from the group consisting of 1 to 5 nucleotides, 1 to 8 nucleotides, 1 to 10 nucleotides, 1 to 15 nucleotides and 1 to 2 nucleotides. In certain embodiments, the nucleic acid oligomer comprises a deoxyribonucleic acid or analogs thereof, a ribonucleic acid or analogs thereof, a locked nucleic acid (LNA) or analogs thereof, a protein nucleic acid (PNA), a nucleic acid with a phosphorothionate linkage, or a combination thereof. In certain embodiments, the first site on the nucleic acid oligomer comprises at least one of a nucleotide base, a 2' sugar, a 3' sugar, or a 5' sugar.

In certain embodiments, detection comprises UV absorbance, fluorescence, visible light, magnetic resonance, chemiluminescence, conductance, an electrical signal, a secondary biological reaction product, or a combination thereof.

In certain embodiments, the detectable tag comprises a radioactive tag, a dye, a fluorescent quencher, a nanocrystal, a spin label, a semiconductor, a biological reporter molecule, or a combination thereof.

In certain embodiments, the dye comprises an optically detectable dye. In certain embodiments, the optically detectable dye comprises a chemiluminescent dye, a fluorescent dye, or a combination thereof. In certain embodiments, the fluorescent dye comprises a pyrene dye, a polymer dye, a xanthene dye, cyanine dye, a coumarin dye, a borapolyazaindacine dye, a benzofuran dye, an indole dye, or combinations thereof. In certain embodiments, the fluorescent dye comprises fluorescein, rhodamine, d-rhodamine.

In certain embodiments, the fluorescein dye comprises FAM™, JOE™, VIC™, HEX™, TET™, NED™, PET®, or a combination thereof. In certain embodiments, the rhodamine comprises TAMRA™, ROX™, R110, R6G, Texas Red®, or a combination thereof. In certain embodiments, the dye comprises aminopyrene trisulfonic acid (APTS), NBD, BigDye™, or a tautomer or salt thereof.

In certain embodiments the dye containing a hydrazinyl substituent includes but is not limited to sulfonate, phosphate, phosphonate, and carboxylate groups, or their derivatives.

In certain embodiments of determining a glycan sequence the reactive moiety comprises a protected group, an activatable group, an unprotected group, or a combination thereof. In certain embodiments, the reactive moiety comprises an oxime, a hydrazide, a hydrazine, a sulfahydryl, a phosphine, an aldehyde, an aminooxy, an azide, an alkyne, an amine, or a combination thereof. In certain embodiments, the mobility modifier is either attached to the nucleic acid oligomer, or, the mobility modifier is attached to the dye, and wherein the mobility modifier comprises an instrinsic charge and is reactive. In other embodiments of determining a glycan sequence the mobility modifier comprises a polyethylene oxide chain, a linear or branched hydrophilic chain, a linear or branched hydrophobic chain, a linear or branched amphiphillic chain, a hexyl linker, a polypeptide chain, a polyamide chain, or a combination thereof.

In certain embodiments, a method of generating a glycan database is provided, comprising:
(i) empirically obtaining a plurality of migration times corresponding to a plurality of glycans that have migrated through a capillary, the capillary comprising a sieving polymer, before or upon subjection of the capillary to an electric field; and
(ii) arranging the plurality of migration times in correspondence with an identification information for each member of the glycans, into a database configured to be accessible by a computer,
wherein, the glycan is labeled with a nucleic acid oligomer and optionally, with a detectable tag.

In other embodiments, a method of labeling a glycan on a target analyte is provided, comprising:
(a) cleaving the glycan from the target analyte with an enzyme to generate an enzyme-digestion mixture;
(b) separating the cleaved glycan from the enzyme-digestion mixture of (a); and
(c) labeling the cleaved glycan with a reactive nucleic acid oligomer, wherein the nucleic acid oligomer comprises:
 i) a first site comprising an intrinsic charge and a reactive moiety, wherein the reactive moiety enables attachment of the nucleic acid oligomer to the glycan; and
 ii) optionally, a second site comprising a detectable tag.

In further embodiments of labeling a glycan on a target analyte, a labeled, dextran size ladder is provided comprising: a plurality of dextran oligomers, each having a unique and distinguishable number of dextran units; (i) a nucleic acid oligomer; (ii) optionally, a detectable tag, and wherein, each dextran oligomer is distinguishable due to its own characteristic mobility shift on a given separation means, and wherein, the nucleic acid oligomer comprises a reactive moiety that enables attachment of the nucleic acid oligomer to each dextran oligomer.

In certain embodiments a labeled, dextran size ladder the nucleic acid oligomer is provided that comprises 1 to 20 nucleotides, or, comprises 1 to 5 nucleotides, 1 to 8 nucleotides, 1 to 10 nucleotides, 1 to 15 nucleotides and 1 to 2 nucleotides. In certain embodiments of the labeled, dextran size ladder the nucleic acid oligomer comprises a deoxyribonucleic acid or analogs thereof, a ribonucleic acid or analogs thereof, a locked nucleic acid (LNA), a nucleic acid with a phosphorothionate linkage, protein nucleic acid (PNA), or a combination thereof. In other embodiments, the nucleic acid oligomer comprises at least one of a nucleotide base, a 2' sugar, a 3' sugar, or a 5' sugar. In other embodiments, the nucleic acid oligomer is detected by UV absorbance, or the detectable tag is detected by fluorescence, visible spectrum, a spin label, chemiluminescence, electrochemical conductance, electrical signal, through a secondary biological reaction product, or a combination thereof. In certain embodiments of the labeled, dextran size ladder the detectable tag comprises a radioactive tag, a dye, a fluorescent quencher, a nanocrystal, a spin label, a semiconductor, a biological reporter molecule, or a combination thereof.

In certain embodiments a method of increasing the net charge of an analyte is provided, comprising: labeling the analyte with a nucleic acid oligomer that comprises: i) a reactive moiety at a first site and an intrinsic charge; and, ii) optionally, a detectable tag at a second site. In certain embodiments the analyte is selected from the group consisting of a protein, a lipid, a lipid vesicle, an oligosaccharide, a ligand and a cell. In certain embodiments the cell comprises a whole cell, a part of a cell, a live cell, a dead cell, an infected cell, a cancer cell, a normal cell, an abnormal cell, a virus, a viral envelope, a fragment of the virus, or a combination thereof. In certain embodiments the infected cell is infected due to a group of infectious agents selected from a virus, a bacteria, a protozoan, a fungus, a *chlamydia*, a *mycoplasma*, a prion, or a combination thereof. In certain embodiments the analyte is a protein which is linked to the nucleic acid oligomer through any R side chain of an amino acid on the protein. In certain embodiments the protein is selected from the group consisting of an antibody or its fragments, an enzymatically degraded peptide, non-ribosomal proteins, a posttranslationally modified protein, a metabolically-altered protein, a disease-altered protein, a transmembrane protein/peptide, a cell surface receptor, or a combination thereof. In certain embodiments the metabolically-altered protein comprises either a methionine oxidation or a cysteine sulfonation.

In certain embodiments a method of propelling an analyte in an electric field is provided, comprising: labeling the analyte with a nucleic acid oligomer wherein the nucleic acid oligomer comprises: a) a reactive moiety at a first site and an intrinsic charge; and b) optionally, a detectable tag at a second site; applying an electric field to propel said analyte across the electric field. In certain embodiments the electric field is from an instrument selected from the group consisting of a cell sorter, a cell scanner, a flow cytometer, an electrophoretic chamber, a CE instrument and a combination thereof.

In certain embodiments a method for sorting a plurality of analytes simultaneously from a mixture is provided, comprising: labeling each analyte with at least one nucleic acid oligomer, wherein the nucleic acid oligomer comprises: a) a reactive moiety at a first site and an intrinsic charge; and b)

optionally, a detectable tag at a second site; propelling each analyte in a charge-differential field such that the intrinsic charge on each analyte separates each analyte into a unique location in space on the charge-differential field; identifying, and optionally eluting, each separated analyte in each unique location, wherein, each reactive moiety at said first site of said nucleic acid oligomer enables attachment of each oligomer to each analyte.

In certain embodiments a kit for detecting at least one glycan in a sample is provided, comprising: sample preparation reagents and buffers; at least one glycan-cleaving enzyme; at least one charged, reactive nucleic acid oligomer for labeling the glycan, wherein the charged, reactive nucleic acid oligomer comprises: a) a reactive moiety at a first site on the nucleic acid oligomer; and b) optionally, a detectable tag at a second site on the nucleic acid oligomer; and, instructions for use. In certain embodiments the at least one glycan-cleaving enzyme is immobilized on a solid surface. In certain embodiments it comprises purification beads and the beads are magnetic. In certain embodiments the magnetic purification beads comprise surface modifications configured to bind to the at least one glycan in the sample.

In certain embodiments of the kit the detectable tag is a dye, and further wherein, the dye is selected from the group consisting of a chemiluminescent dye, a fluorescent dye, and further wherein the fluorescent dye is selected from the group consisting of a pyrene dye, a polymer dye, a xanthene dye, cyanine dye, a coumarin dye, a hydrazinyl substituent, a borapolyazaindacine dye, a benzofuran dye, an indole dye, and combinations thereof. In certain embodiments of the kit, a spin column is configured to separate the labeled glycans from unwanted reaction components consisting of: an excess of dye reagent, an unwanted side product, diluting components, buffers and a combination thereof.

In certain embodiments a kit for sequencing a glycan in a sample is provided, comprising:
 i. at least one endoglycosidase enzyme;
 ii. at least one nucleic acid oligomer comprising a detectable tag, an intrinsic charge, a reactive moiety to attach the at least one nucleic acid oligomer to the glycan in the sample, and optionally, a reactive mobility modifier that can also attach to the glycan;
 iii. a plurality of linkage-specific exoglycosidases; and
 (iv) instructions for use.

In certain embodiments the at least one endoglycosidase enzyme is immobilized on a solid surface. In certain embodiments the kit further comprises purification beads and in some embodiments, the beads are magnetic. In certain embodiments the magnetic purification beads comprise surface modifications configured to bind to the glycan in the sample. In certain embodiments the detectable tag labeled, reactive nucleic acid oligomer, or a detectable tag labeled, reactive mobility modifier bind to the glycan to form a labeled glycan. In certain embodiments the kit further comprises a spin column configured to separate the labeled glycans from unwanted reaction components consisting of: an excess of dye reagent, an unwanted side product, diluting components, buffers and a combination thereof.

In certain embodiments a system for detecting at least one glycan in a sample is provided, comprising: (i) at least one nucleic acid oligomer comprising a detectable tag, an intrinsic charge, a reactive moiety to attach said nucleic acid oligomer to said at least one glycan in the sample to generate a labeled glycan, (ii) a channel comprising a sieving polymer; (iii) an anode and a cathode operably connected to the channel, configured to provide an electric field to the channel; and (iv) a detector configured to detect the detectable tag on the labeled glycan, wherein the detector detects ultraviolet absorbance, fluorescence, chemiluminescence, or visible light absorption, and wherein, the at least one nucleic acid oligomer may optionally comprise a mobility modifier. In certain embodiments a data processor is operably connected to the detector. In other embodiments a second analytical mode selected from the group consisting of hydrophilic liquid chromatography, UPLC, mass spectrometry, and UV absorbance.

In certain embodiments a method of making a dye labeled, reactive nucleic acid oligomer on a solid support is provided, comprising: attaching a dye to the solid support; optionally, adding one or more activated linkers; optionally, adding a mobility modifier to said activated linker; attaching a nucleic acid oligomer to said activated linker to generate the dye labeled, reactive nucleic acid oligomer.

In certain embodiments, the kit further comprises instructions for labeling glycans in a sample in preparation of glycan analysis, the method comprising:
treating the sample with a release reagent, such as PNGase F enzyme, with an appropriate buffer under conditions suitable for the release of the glycan from the biomolecule, thereby forming a reaction mixture;
adding beads and buffer to the reaction mixture;
separating the supernatant from the beads;
washing the beads with wash buffer;
eluting the glycans from the beads with elution buffer;
performing dye labeling of the glycans using one or more dye compounds provided herein, thereby forming a glycan-containing solution;
optionally, removing excess dye using fresh beads; washing beads, separating the beads from excess dye/wash solution; and eluting glycans from the beads; and
collecting the glycan-containing solution.

In certain embodiments, the glycan solution may be stored for future use according to instructions provided, or analyzed for its glycan profile using a CE analyzer or uPLC analyzer or a combination thereof.

DESCRIPTION

Figure 1:
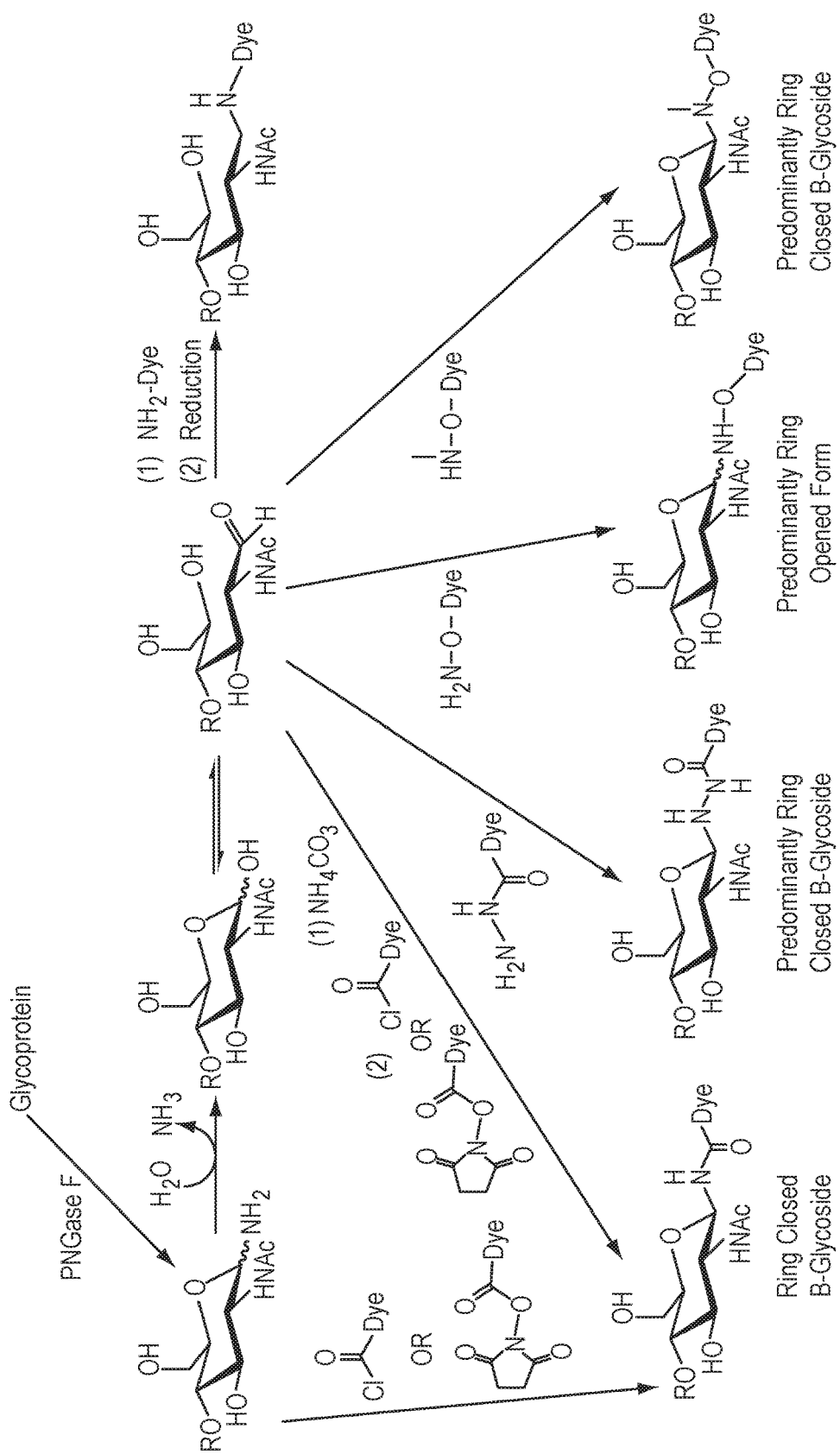
FIG. 1: Schematic for various methods for reduced end conjugation of glycans.

As used herein, "sample" and its derivatives, may be used in its broadest sense and includes any specimen, culture and the like that may be suspected of including a glycoconjugate or a biomolecule which may be treated to provide a glycan for analysis. The sample can include any biological, clinical, surgical, agricultural, atmospheric or aquatic-based specimen containing one or more glycoconjugates or biomolecules.

As used herein, a "biomolecule" may be used in its broadest sense and in some embodiments, biomolecules may include polymers such as proteins and their polymer subunits, polysaccharides and their polymer subunits, nucleic acids and their polymer subunits, proteoglycans, glycosaminoglycans, synthetic glycans, native glycans, derivatized glycans, glycoproteins, glycolipids, phosphoproteins, glycan core containing phospholipid-proteins, lipopolysaccharides, or combinations thereof. The biomolecules can be isolated from any source such as solid tissue, liquid tissues including but not limited to blood, prokaryotic and eukaryotic cells, viruses, and other microorganisms. Methods for isolating biomolecules from these sources are well known in the art. For example, the solid tissue or tissue can be weighed, cut, mashed, homogenized, and the biomolecules can be isolated from the homogenized samples. In some embodiments, a term "glycoconjugate" may be used interchangeably with the term "biomolecule". In some embodiments, a glycoconjugate may refer to a glycoprotein, a glycolipid, or a proteoglycan.

The term "mobility-dependent separation" as used herein refers to the separation of a biomolecule, for example, glycan fragments or labeled glycan fragments due to their charge and size associated with the fragment.

As used herein, a "nucleic acid oligomer" or a "charged nucleic acid oligomer", or a "reactive nucleic acid oligomer", or a "charged, reactive nucleic acid oligomer" refers to any naturally occurring nucleotide, or unnaturally occurring nucleotide, or an analog thereof, that may comprise 1, 2, 3, . . . 50 linked nucleotides, or nucleotide chain that provide an intrinsic charge to any molecule or biomolecule or species it is attached to. In other embodiments, the "nucleic acid oligomer" has a preferred length of 1-10 nucleotides. In yet another embodiment, the "nucleic acid oligomer" has a preferred length of 1-20 nucleotides, 1-30 nucleotides, 1-40 nucleotides, 1-50 nucleotides, 5-15 nucleotides, 5-25 nucleotides, 5-35 nucleotides, 5-4 nucleotides, and so on. In a preferred embodiment, the "nucleic acid oligomer" has a preferred length of 1-5 nucleotides. When a "nucleic acid oligomer" or a "charged nucleic acid oligomer" is attached to a glycan, the glycan may be referred to as a "charge labeled glycan".

The term "detectable tag" as used herein refers to moieties that can be identified, and may be used to directly or indirectly detect the molecule, the sequence, or the part to which the detectable tag may be attached. In some embodiments, the term "detectable tag" may be referred to, or used interchangeably with the term "label". Various detectable tags or labels may be useful, and they include, but are not limited to, a radioactive tag, a dye, a quencher dye, a nanocrystal, a spin label, a semiconductor, a biological reporter molecule, or a combination thereof. Detectable tags may be identifiable by sequence, length, presence or absence of an analog, (for example, a nucleotide analog or a derivatized analog, etc.), dimensional structures (for example, stem-loops, Y-shapes, etc.), dyes (for example, fluorescent, visible, quencher, FRET interaction dyes, etc.), hybridization to templates or probes, presence of restriction enzyme sites, binding properties to bio-affinity ligands (for example, biotin, antibody, etc.), position on an array or on a differential charge field, mass spectrometry, cleavage by enzyme, chemical, physical entity, or electromagnetic radiation (for example, visible light, UV light, etc.), RNase H cleavage (for example, for RNA based tags, etc.), electrical properties (for example, when employing a nanoelectrode, for example see U.S. Pat. No. 7,963,347 hereby incorporated by reference), cleavable base (for example, uracil cleavage with UDG, etc.), or a combination thereof.

The term "fluorescent dye" as used herein refers to moieties that absorb light energy at a defined excitation wavelength and emit light energy at a different wavelength. Preferably, if a plurality of fluorescent dyes may be selected for use in one experiment, they are spectrally resolvable. As used herein, "spectrally resolvable" means that the dyes can be distinguished on the basis of their spectral characteristics, particularly fluorescence emission wavelength, under conditions of operation. For example, the identity of the one or more terminal nucleotides can be correlated to a distinct wavelength of maximum light emission intensity, or perhaps a ratio of intensities at different wavelengths. In certain embodiments, the preferred fluorescent dyes include, but are not limited to, FAM™, JOE™, VIC™, HEX™, TET™, NED™, PET®, TAMRA™, ROX™, R110, R6G, Texas Red®, aminopyrene trisulfonic acid (APTS), NBD, Big-Dye™, or a tautomer or salt thereof, or a combination thereof.

As used herein, the term "nucleotide" and its variants comprises any compound, including without limitation any naturally occurring nucleotide or analog thereof. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide may be referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. .alpha.-thio-nucleotide 5'-triphosphates. For a review of nucleic acid chemistry, see: Shabarova, Z. and Bogdanov, A. Advanced Organic Chemistry of Nucleic Acids, VCH, New York, 1994.

As used herein, the terms "polynucleotide", "nucleic acid", or "oligonucleotide" refers to a linear polymer of nucleosides (including deoxyribonucleosides, ribonucleosides, or analogs thereof) joined by inter-nucleosidic linkages. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides comprising the bases, as is standard in the art. In naturally occurring polynucleotides, the inter-nucleoside linkage may be a phosphodiester bond, and the subunits are referred to as "nucleotides." Oligonucleotide primers comprising other inter-nucleoside linkages, such as phosphorothioate linkages, may be used in certain embodiments of the teachings. Also included herein are nucleotide analogs, for example, a deoxyribonucleic acid or analogs thereof, a ribonucleic acids or analogs thereof, a locked nucleic acid (LNA) or analogs thereof, a protein nucleic acid (PNA), a nucleic acid with a phosphorothionate linkage, or a combination thereof. It will be appreciated that one or more of the subunits that make up such an oligonucleotide primer with a non-phosphodiester linkage may not comprise a phosphate group. Such analogs of nucleotides are considered to fall within the scope of the term "nucleotide" as used herein, and nucleic acids comprising one or more inter-nucleoside linkages that are not phosphodiester linkages are still referred to as "polynucleotides", "oligonucleotides", etc.

As used herein, the term "phosphorothioate linkage" refers to an inter-nucleotide linkage comprising a sulfur atom in place of a non-bridging oxygen atom within the phosphate linkages of a sugar phosphate backbone. The term phosphorothioate linkage refers to both phosphorothioate inter-nucleotide linkages and phosphorodithioate inter-nucleotide linkages. A "phosphorothioate linkage at a terminal 3' end" refers to a phosphorothioate linkage at the 3' terminus, that is, the last phosphate linkage of the sugar phosphate backbone at the 3' terminus.

As used herein, the term "phosphodiester linkage" may refer to the linkage —$PO_4$— which may be used to link nucleotide monomers, such as the inter-nucleotide linkages found in naturally-occurring DNA. Additionally, "phosphodiester linkage" may refer to portions of the NCMs or NCM linkers of the chemically-enhanced primers of the present disclosure.

The term "nucleobase" or "base" as used herein refers to a nitrogen-containing heterocyclic moiety capable of forming Watson-Crick type hydrogen bonds with a complementary nucleobase or nucleobase analog, e.g. a purine, a 7-deazapurine, or a pyrimidine. In certain embodiments, nucleobases included may be naturally occurring nucleobases adenine, guanine, cytosine, 5 mC, uracil, thymine, and analogs of naturally occurring nucleobases, e.g. 7-deazaadenine, 7-deaza-8-azaadenine, 7-deazaguanine, 7-deaza-8-azaguanine, N6-Δ2 isopentenyl-adenine (6iA), N6-Δ2-isopentenyl-2-methylthioadenine (2ms6iA), N2-dimethyl-guanine (dmG), 7-methylguanine (7mG), inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 2-thiopyrimidine, 6-thioguanine, 4-thiothymine, 4-thiouracil, $O^6$-methylguanine, $N^6$-methyl-adenine, $O^4$-methylthymine, 5,6-dihydrothymine, 5,6-dihydrouracil, 4-methylindole, pyrazolo[3,4-D]pyrimidines (see, e.g., U.S.

Pat. Nos. 6,143,877 and 6,127,121 and PCT Published Application WO 01/38584) and ethenoadenine. Nonlimiting examples of nucleotide bases can be found, e.g., in Fasman, Practical Handbook of Biochemistry and Molecular Biology, pp. 385-394, CRC Press, Boca Raton, Fla. (1989).

As used herein, the term "end" or "site" and its variants, when used in reference to a nucleic acid molecule, or on a reactive nucleic acid oligomer and can include the terminal 3 nucleotides, the terminal 2 and even more typically the terminal nucleotide of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that may not linked to a 5' phosphate group of a mononucleotide pentose ring. In some embodiments, the 3' end does not include any unlinked 3' hydroxyl group but includes a reactive moiety capable of reacting with the reducing end of a glycan, i.e. an aldehyde or equivalent functionality. The 3' end may further include a linker portion which links the nucleic acid molecule to the reactive moiety and may include 1-100 non-hydrogen atoms including carbon, nitrogen, oxygen, sulfur, and phosphorus atoms in any arrangement and oxidative states. The linker may be linear or branched, and may include cyclic moieties including carbocyclic, heterocyclic, aryl, or heteroaryl rings. In certain embodiments, the first site on the nucleic acid oligomer comprises a nucleotide base, which may be a reactive site for attachment to a biomolecule. In other embodiments, the first site on the nucleic acid oligomer may be a reactive site on a 2', 3', or 5' position of a sugar.

As used herein, "5' end", and its derivatives, generally refers to an end of a nucleic acid molecule, which in a native nucleic acid may include a free 5' phosphate group or its equivalent. In some embodiments, the 5' end includes a 5' phosphate group that may not linked to a 3' hydroxyl of a neighboring mononucleotide pentose ring, but may be linked, optionally via a 5' linker, to a detectable moiety including a spin label, a biological reporter molecule, a dye, which may include a fluorescent dye (including polymeric or energy transfer dyes), gold nanoparticle or a semiconductor nanocrystal. In some embodiments, the 5' end does not include any unlinked 5' phosphate group but may be linked via a 5' linker to the dye, including all the detectable moieties described for a dye linked via a 5' phosphate group to the nucleic acid. The 5' linker, whether linked directly to the nucleic acid end or to a 5' phosphate group attached thereto, may include 1-200 non-hydrogen atoms including carbon, nitrogen, oxygen, sulfur and phosphate and be linear or branched, and may be charged or uncharged. The linker may further include carbocyclic, heterocyclic, aryl or heteroaryl moieties.

The linker at the 5' end may further include a "mobility modifying moiety" or a "mobility modifier" when it contains a charged portion or an intrinsic charge. The charged portion may adjust the size/charge ratio of the overall nucleic acid/nucleic acid conjugate, and may affect the rate of migration of the biomolecule or glycan conjugate when subjected to a charge differential field, for example, to an electrophoresis method described here. As described herein, a mobility modifier may comprise a polyethylene oxide chain, a linear or branched hydrophilic chain, a linear or branched hydrophobic chain, a linear or branched amphiphillic chain, a hexyl linker, a polypeptide chain, a polyamide chain, or a combination thereof.

In various embodiments, a charge differential field may be employed to separate the "charged reactive oligomer". Exemplary separation tools employed may include, but are not limited to, an electric field, a magnetic field, a salt gradient, or a combination thereof. Separation techniques employed may be capillary electrophoresis that may use a sieving polymer, gel electrophoresis (with or without detergents), chromatography, HPLC, mass chromatography, etc.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Selected compounds having a formal electronic charge may be shown without an appropriate biologically compatible counterion. Such a counterion serves to balance the positive or negative charge present on the compound. As used herein, a substance that is biologically compatible may not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

As used herein, the terms "comprises," "comprising," "includes," "including," "has," "having" or any other variation thereof, are intended to cover a non-exclusive inclusion. For example, a process, method, article, or apparatus that comprises a list of features may not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Methods for Complex Glycan Analysis.

Improved methods are described for detecting at least one glycan in a sample comprising a glycoconjugate, and include the steps of cleaving the at least one glycan from a biomolecule or a glycoconjugate; labeling the at least one glycan with a labeling species to produce at least one labeled glycan; migrating the at least one labeled glycan under the influence of an electric field in a channel, where the channel includes a sieving polymer; and detecting a label of the at least one labeled glycan. Upon detecting the label, determination can be made as to whether the at least one glycan may be present and upon comparison to known migration times under similar conditions, assignment of identity of the at least one glycan can be made.

A sample comprising a biomolecule or a glycoconjugate may be obtained from a wide variety of sources including, but not limited to, therapeutic formulations and biological samples, which may include but is not limited to cell cultures, patient samples (including tissue, sputum, blood or urine) or manufacturing processes for therapeutics or other commercially relevant biomolecule or glycoconjugates of interest. In various embodiments, the biomolecule or glycoconjugate may be a glycoprotein or a glycolipid. In the methods, the at least one glycan may be cleaved chemically, for example, by periodate, producing the at least glycan with an aldehyde functionality which can be further modified to aid in its detection. Alternatively, the at least one glycan may be cleaved using at least one glycan-cleaving enzyme, producing the at least one glycan having a reducing functionality, i.e. a hemiacetal or the like, which can be further modified to aid in its detection. In various embodiments, more than one glycan-cleaving enzyme may be used to produce differing patterns of glycan cleavage. In various embodiments, the at least one glycan-cleaving enzyme may be a glycosidase. In various embodiments, the at least one glycan-cleaving enzyme may be an endoglycosidase.

Glycosidases Useful in the Methods.

Glycosidases are specific enzymes that recognize the sugar linkages, and in some cases, the neighboring sugar in the oligo/polysaccharide before cleaving at the precise linkage. Glycosidases used in this invention may be an endoglycosidase, an exoglycosidase, or a combination thereof. Endoglycosidases cleave oligo or polysaccharides, or glycans, from a biomolecule or glycoconjugate, producing a reducing sugar terminus of a cleaved glycan structure which can be further labeled with various labeling species for detection and identification. Exoglycosidases have varied specificities which can be harnessed to specifically and sequentially cleave glycan structures from a terminus, and so explore glycan structure in a given biomolecule or glycoconjugate. In various embodiments of the methods, cleavage with an endoglycosidase may be performed to release a glycan that may be all or the majority of the polysaccharide attached to the biomolecule or glycoconjugate. In some embodiments, a suitable endoglycosidase used for cleaving a glycan from the biomolecule or glycoconjugate may be endoglycosidase F, endoglycosidase F1, endoglycosidase F2, endoglycosidase H, endoglycosidase S, or endoglycosidase D. Alternatively, one or more exoglycosidase may be used to cleave glycans from the terminus of the glycan, and may include, but is not limited to, one or more of α1-2 fucosidase, α1-2,3 mannosidase, α1-3 6 galactosidase, α1-6 mannosidase, α2-3 neuramidase α2-3 neuramidase S, α2-3,6,8 neuramidase, α2-3, 6, 8, 9 neuramidase A, β-N-acetylhexosamidase$_f$, β-N-acetylglucosamidase, β-N-acetylglucosamidase S, β1-3 galactosidase, β1-4 galactosidase, β1-4 galactosidase S, and the like. In various embodiments, cleaving a glycan from each of the denatured glycoprotein samples may include cleaving the glycans using PNGase F, or using endoglycosidase-H, or using one or more of Endo D, Endo F1, Endo F2, and Endo F3, or using one or more of ABS (*arthrobacter ureafaciens* sialidase), NAN 1 (recombinant sialidase), AMF (almond meal alpha-fucosidase), BKF (bovine kidney alpha-fucosidase), BTG (bovine testes beta-galactosidase), SPG (*streptococcus peneumoniae* beta-galactosidase), GUH (*streptococcus pheumoniae* hexosaminidase, recombinant in *E. coli*), and JBM (jack bean mannosidase), or using peptide-N—(N-acetyl-β-glucosaminyl)asparagine amidase, for example. Cleaving the glycan using peptide-N—(N-acetyl-β-glucosaminyl) asparagine amidase may include cleaving N-linked glycans.

Figure 2:
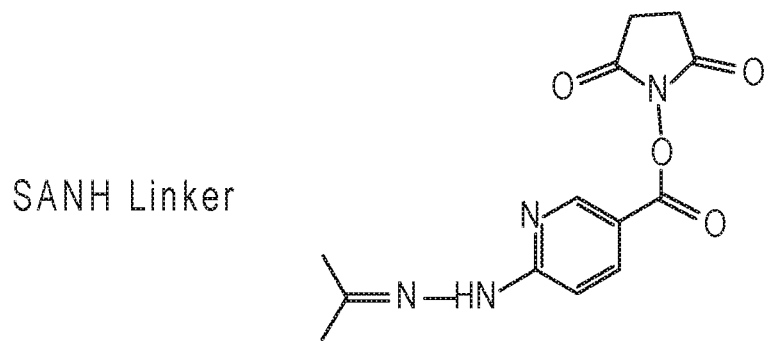
FIG. 2: Structures of exemplary linkers that may be used in glycan conjugation.
Figure 2:
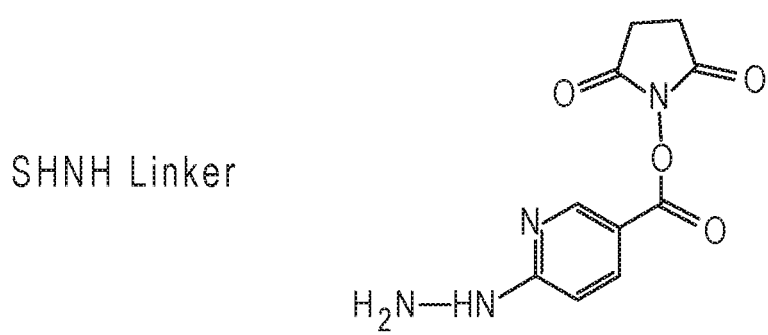
Figure 2:
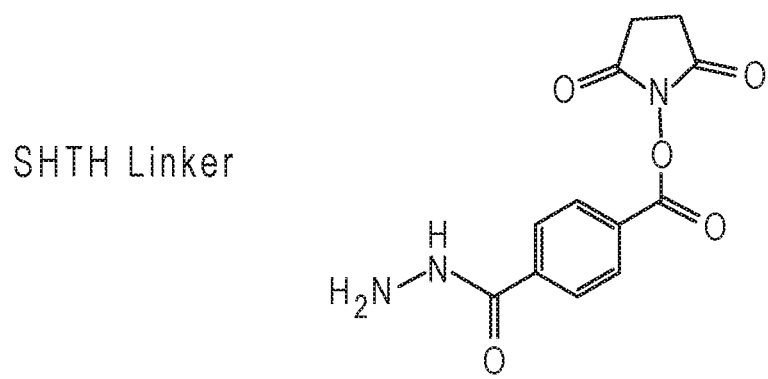
Figure 3A:
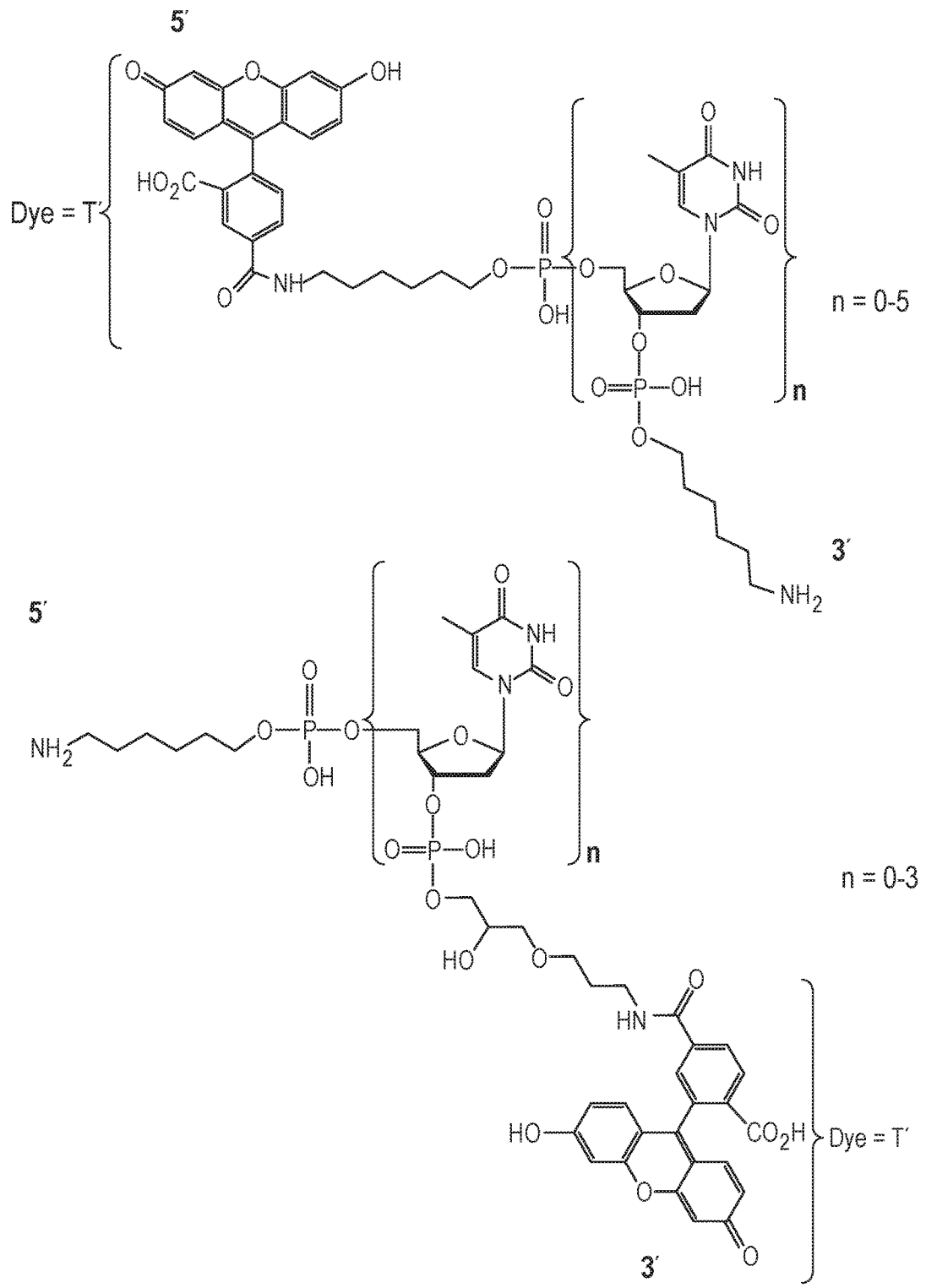
FIG. 3a: Exemplary schematic of a dye labeled nucleic acid oligomer, wherein the dye T' is attached to the 5' end of a nucleotide oligomer (upper panel), or the dye T' is attached to the 3' end of a nucleotide oligomer (lower panel).
Figure 3B:
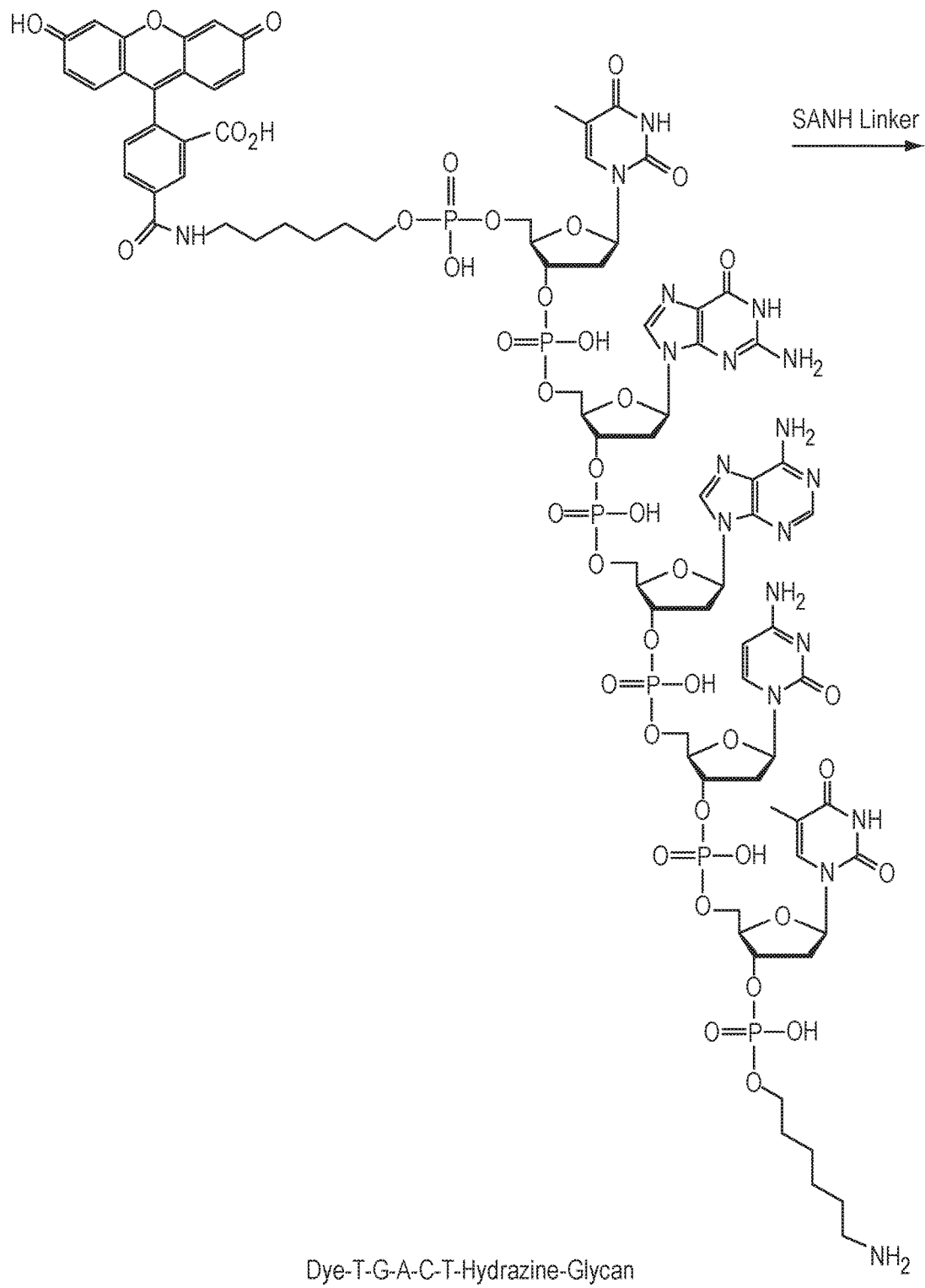
FIG. 3b: Exemplary stepwise solid phase synthesis of a dye labeled nucleic acid oligomer, with attachment of an activated SANH linker, and then conjugation of the dye labeled nucleic acid oligomer to a glycan.
Figure 3B:
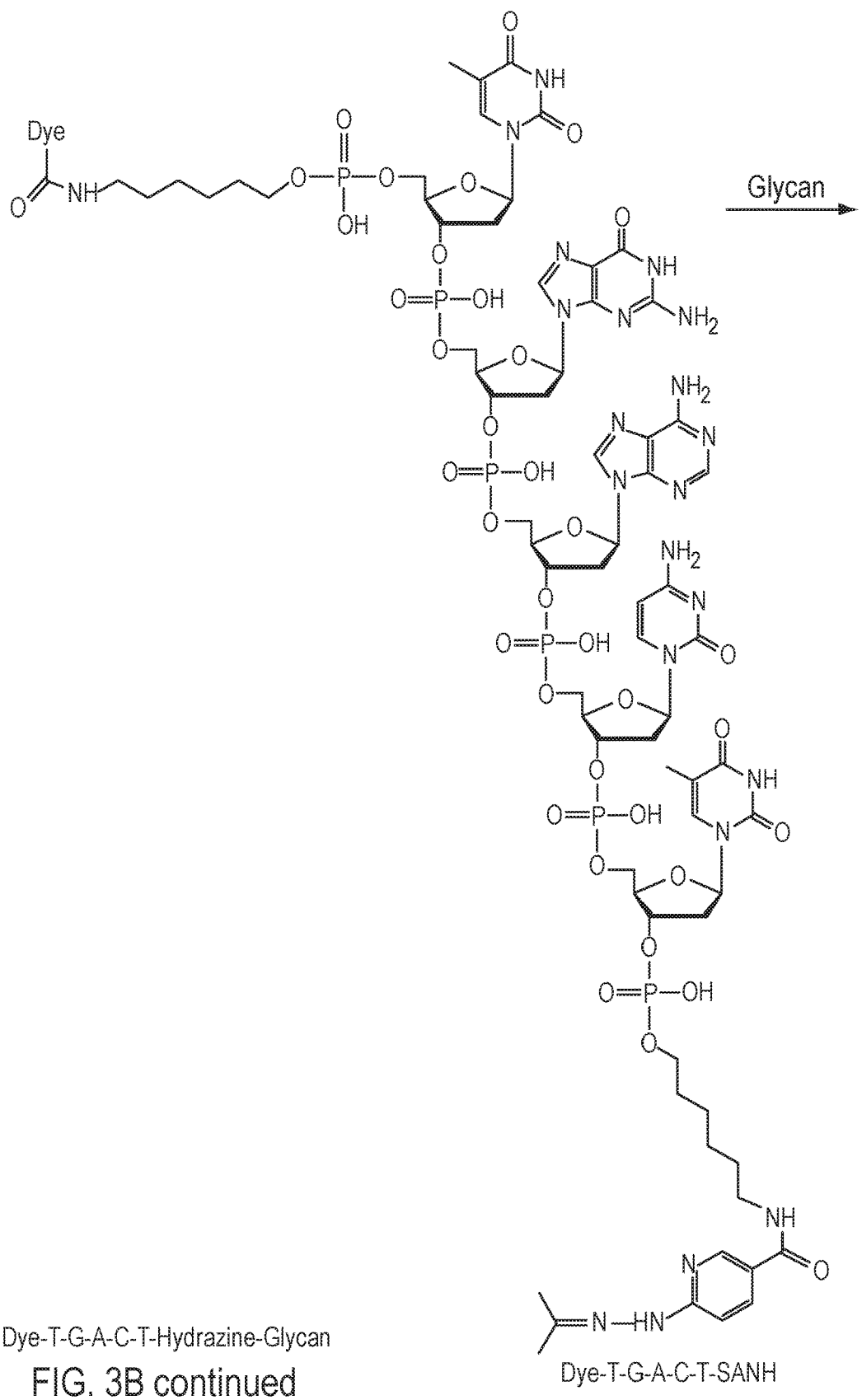
Figure 3B:
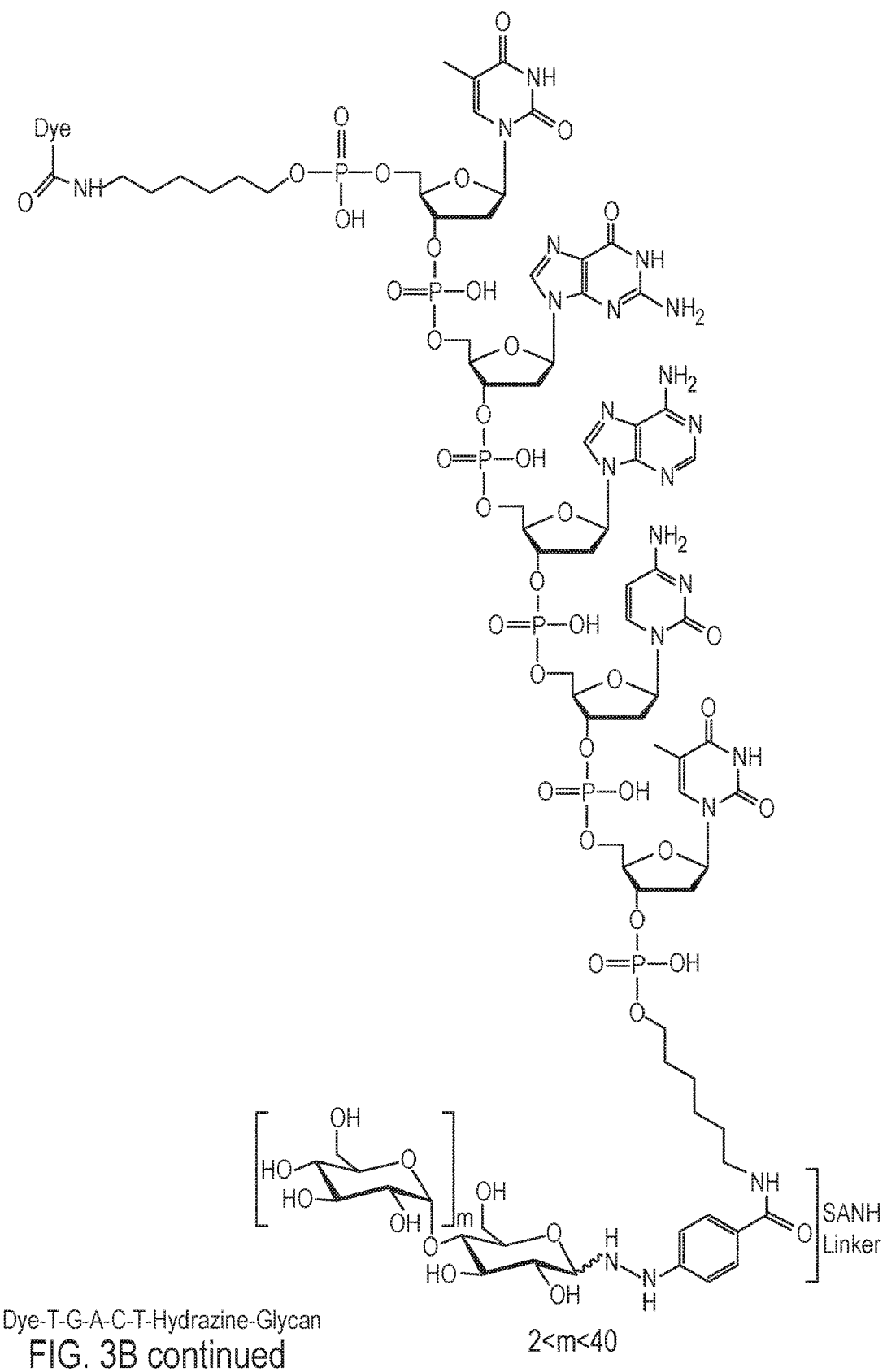
Figure 4:
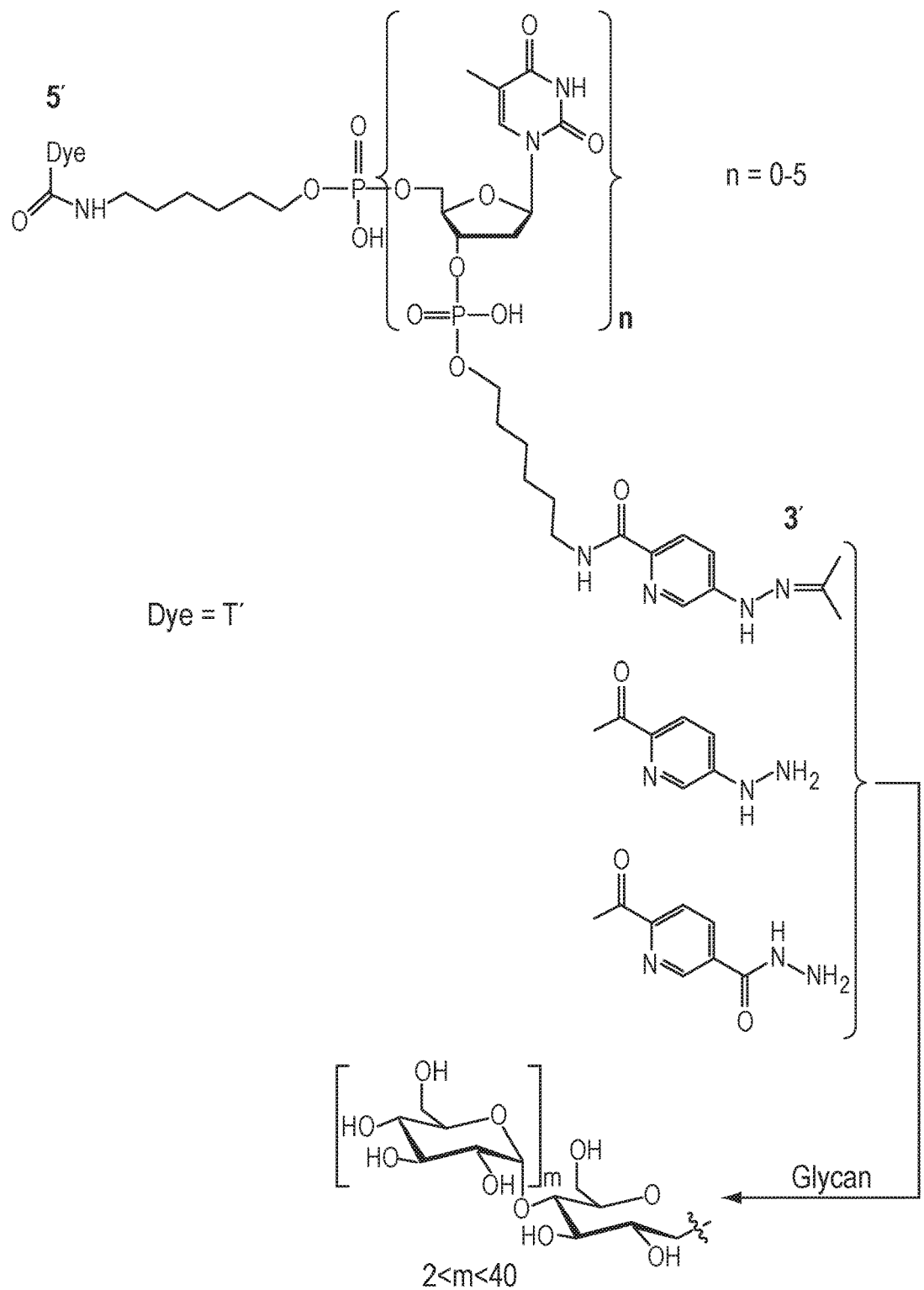
FIG. 4: Exemplary schematic of a dye attached to the 5' end of a nucleic acid oligomer.
Figure 5:
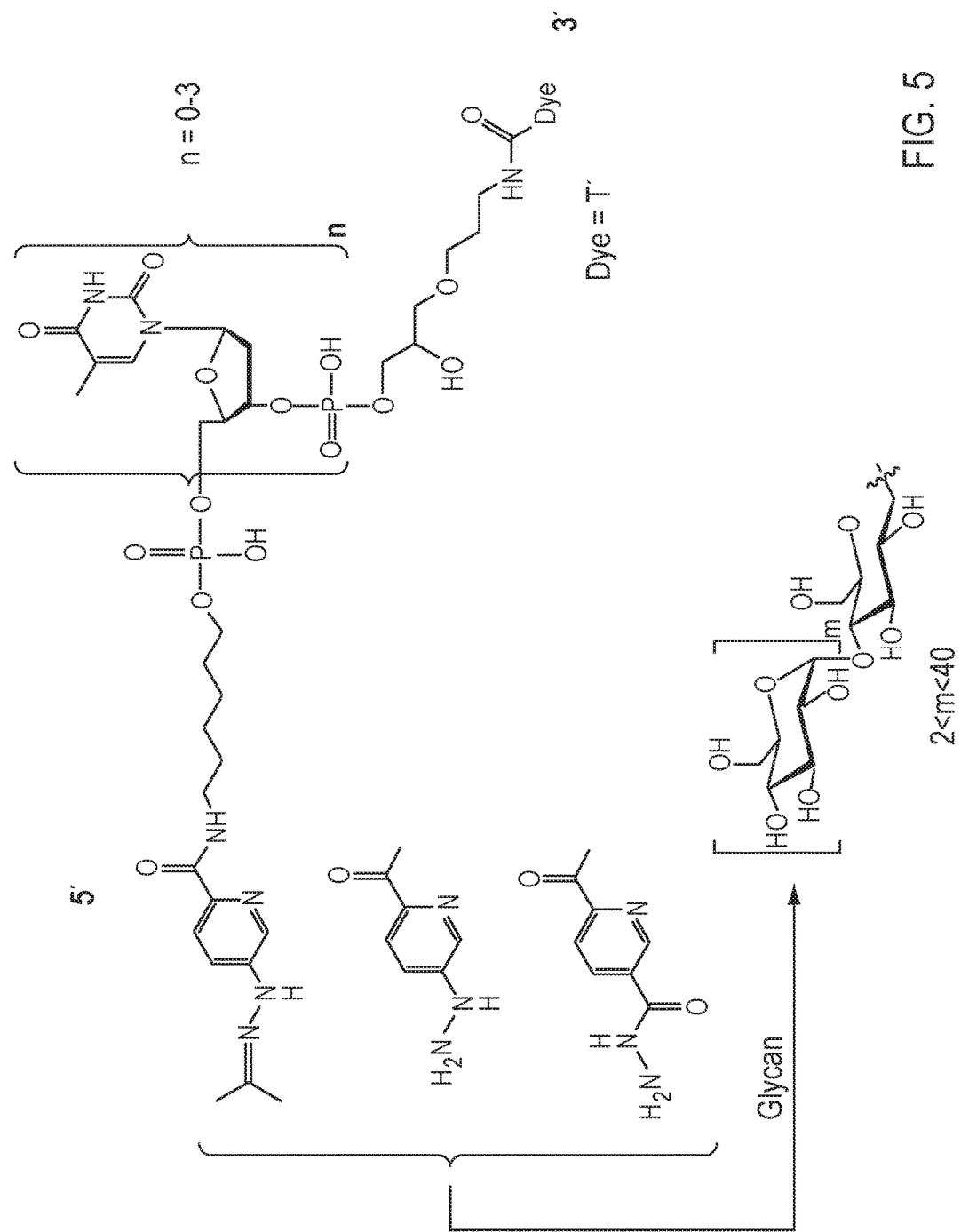
FIG. 5: Exemplary schematic of a dye attached to the 3' end of a nucleic acid oligomer.
Figure 6:
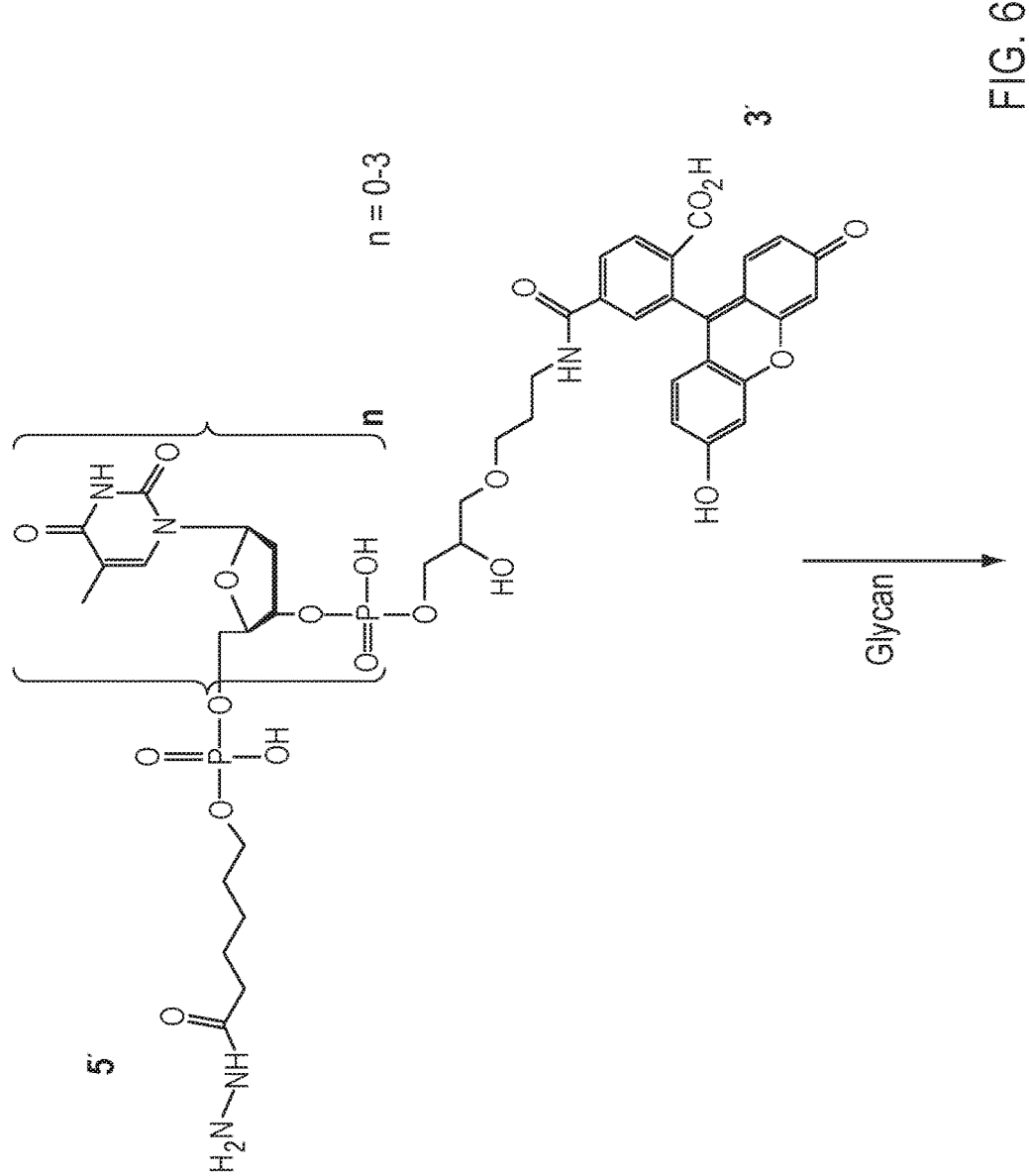
FIG. 6: Exemplary schematic of a dye attached to the 3' end of a nucleic acid oligomer with linkers added manually at the last step.
Figure 6:
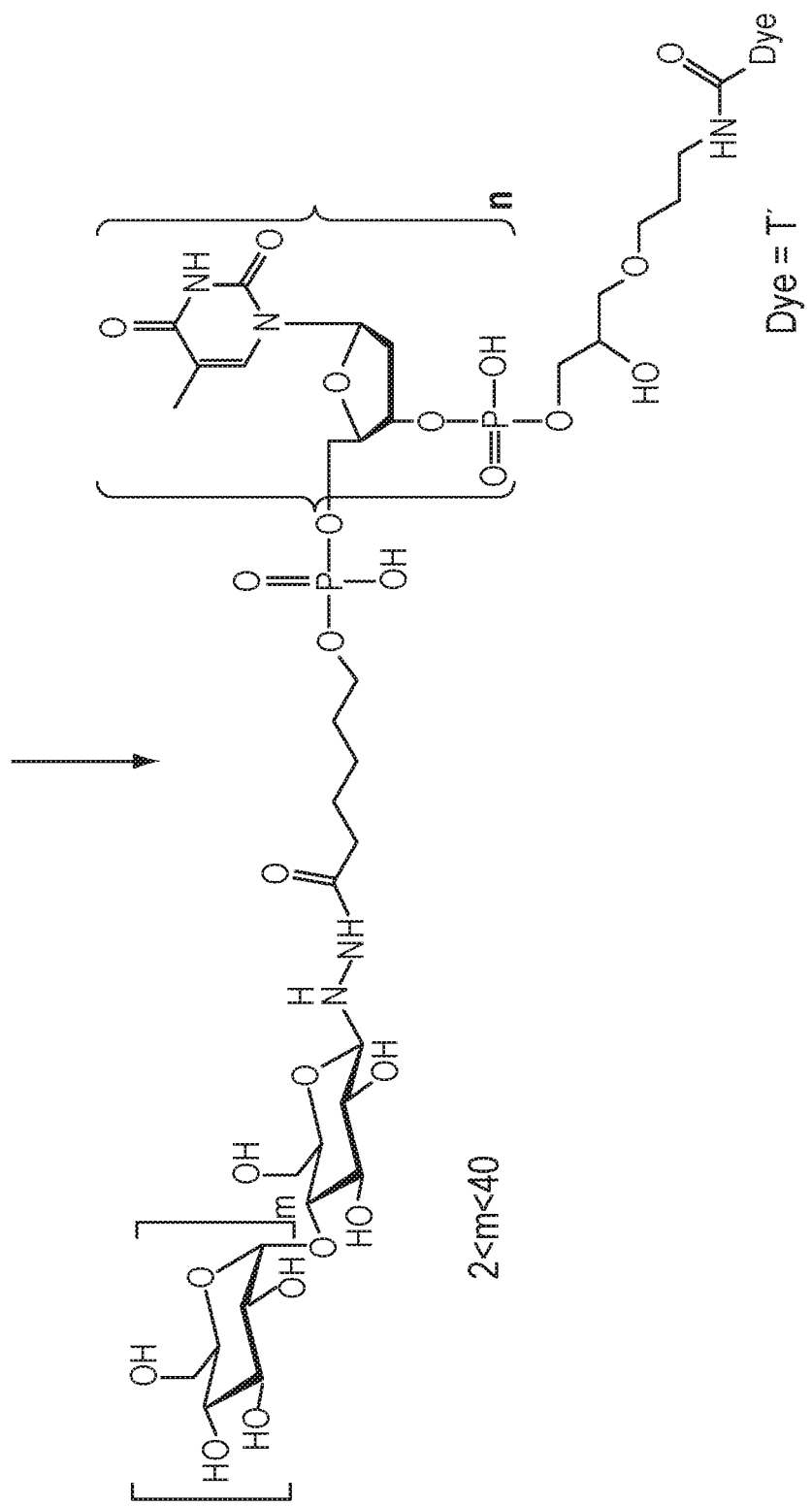
Figure 7:
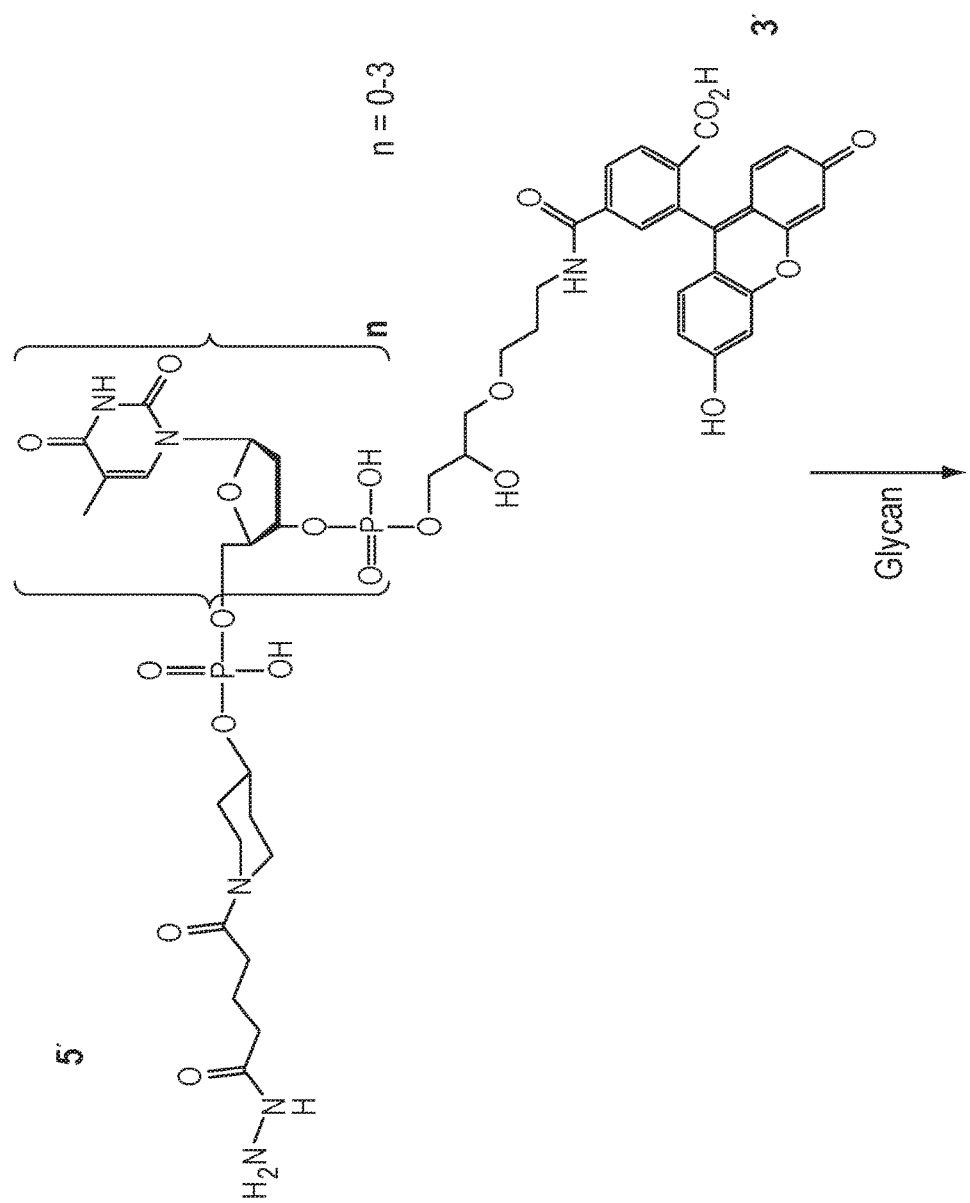
FIG. 7: Another exemplary schematic of a dye attached to the 3' end of a nucleic acid oligomer with straight chain (hydrazide) linker added via solid phase synthesis.
Figure 7:
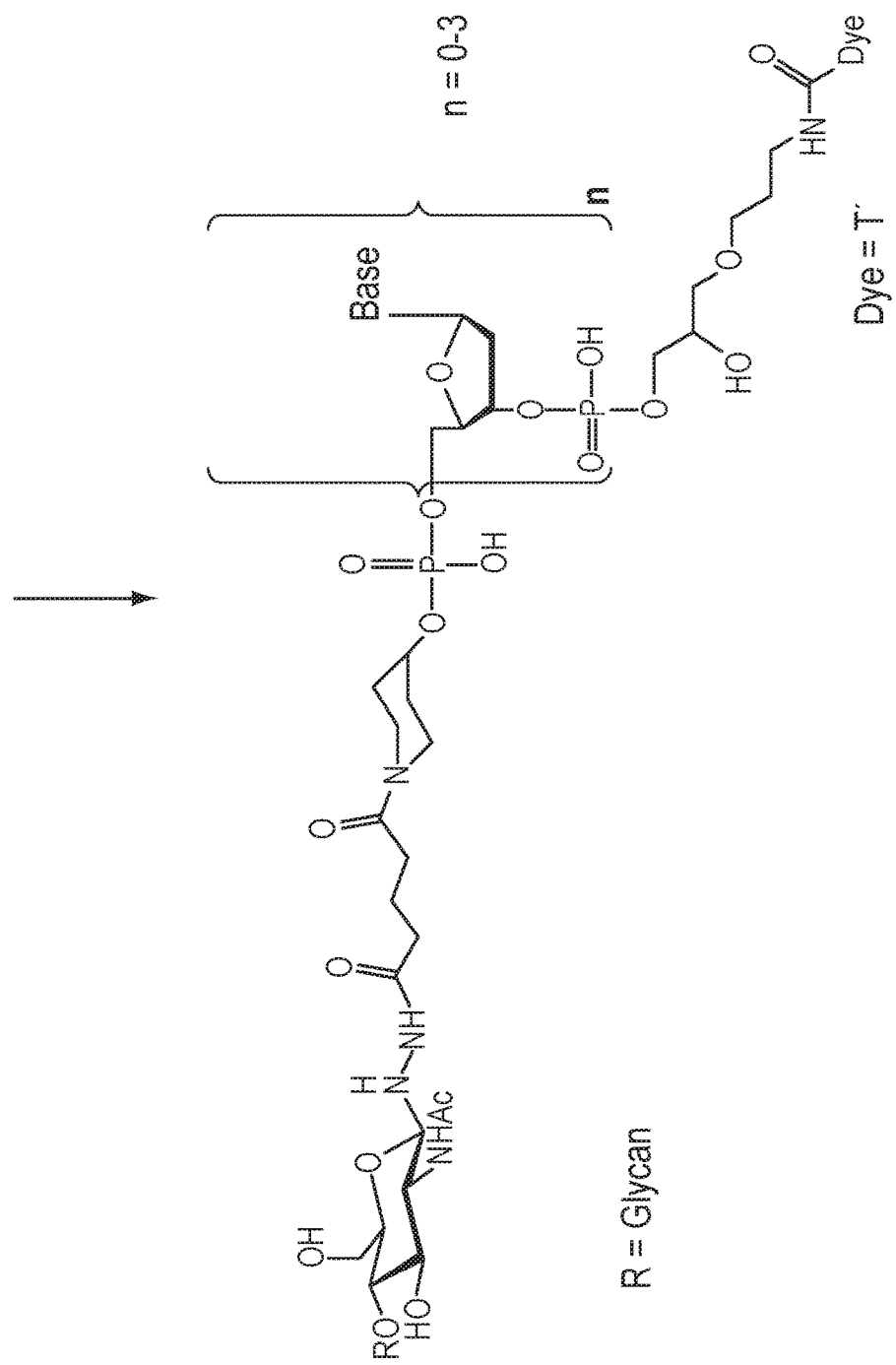
Figure 8:
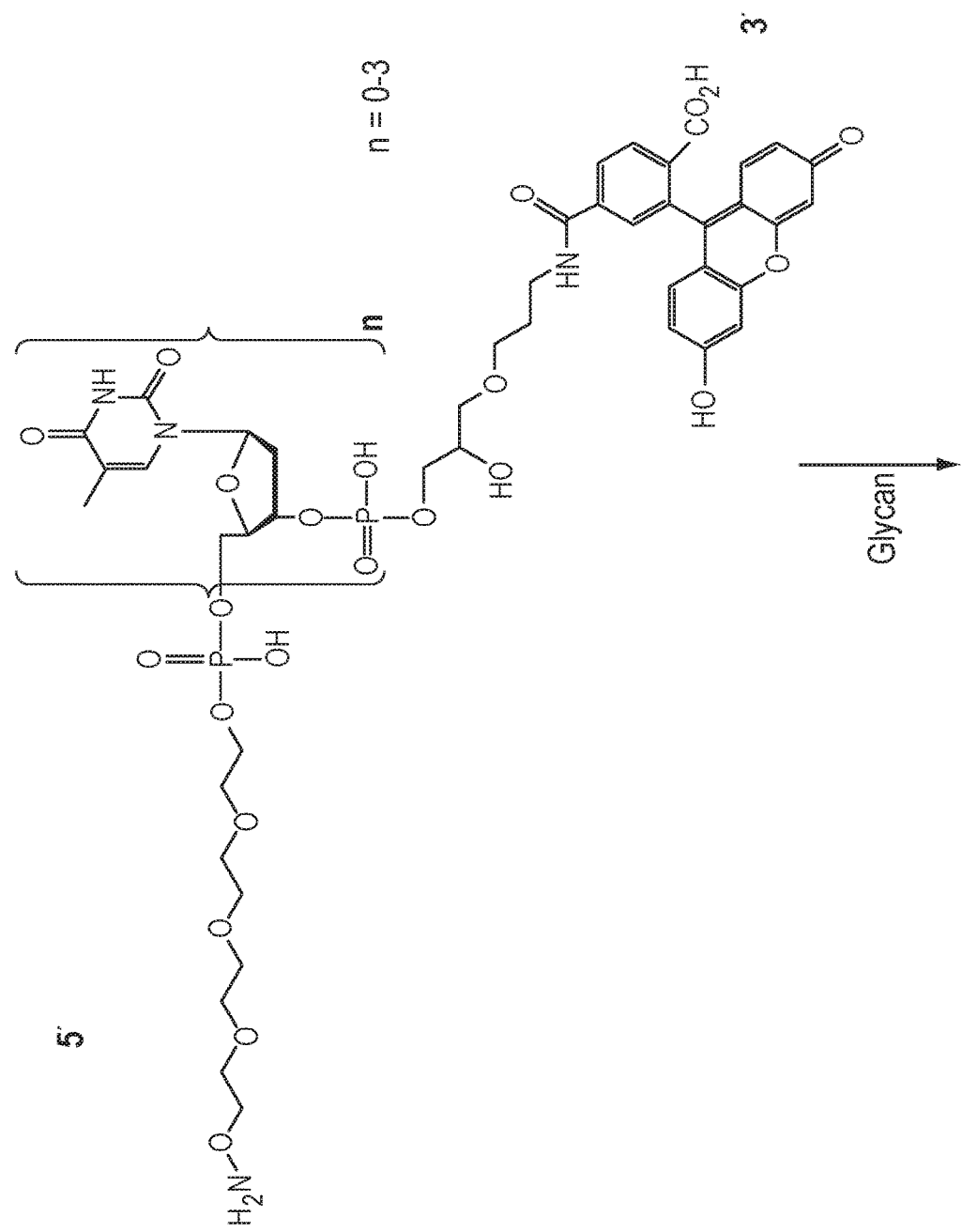
FIG. 8: Another exemplary schematic of a dye attached to the 3' end of a nucleic acid oligomer with 6-membered ring containing aminooxy linker added via solid phase synthesis.
Figure 8:
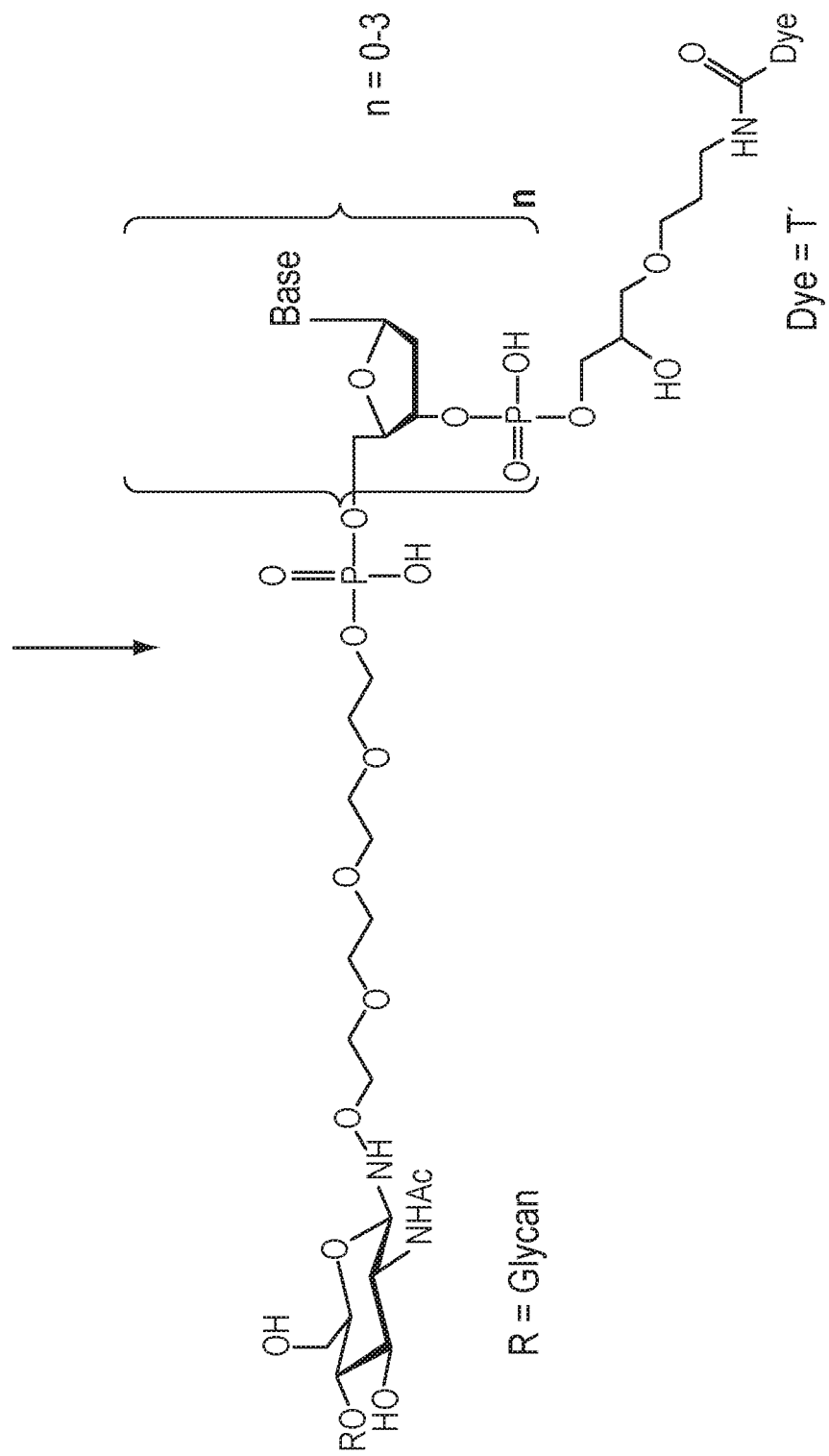
Figure 9:
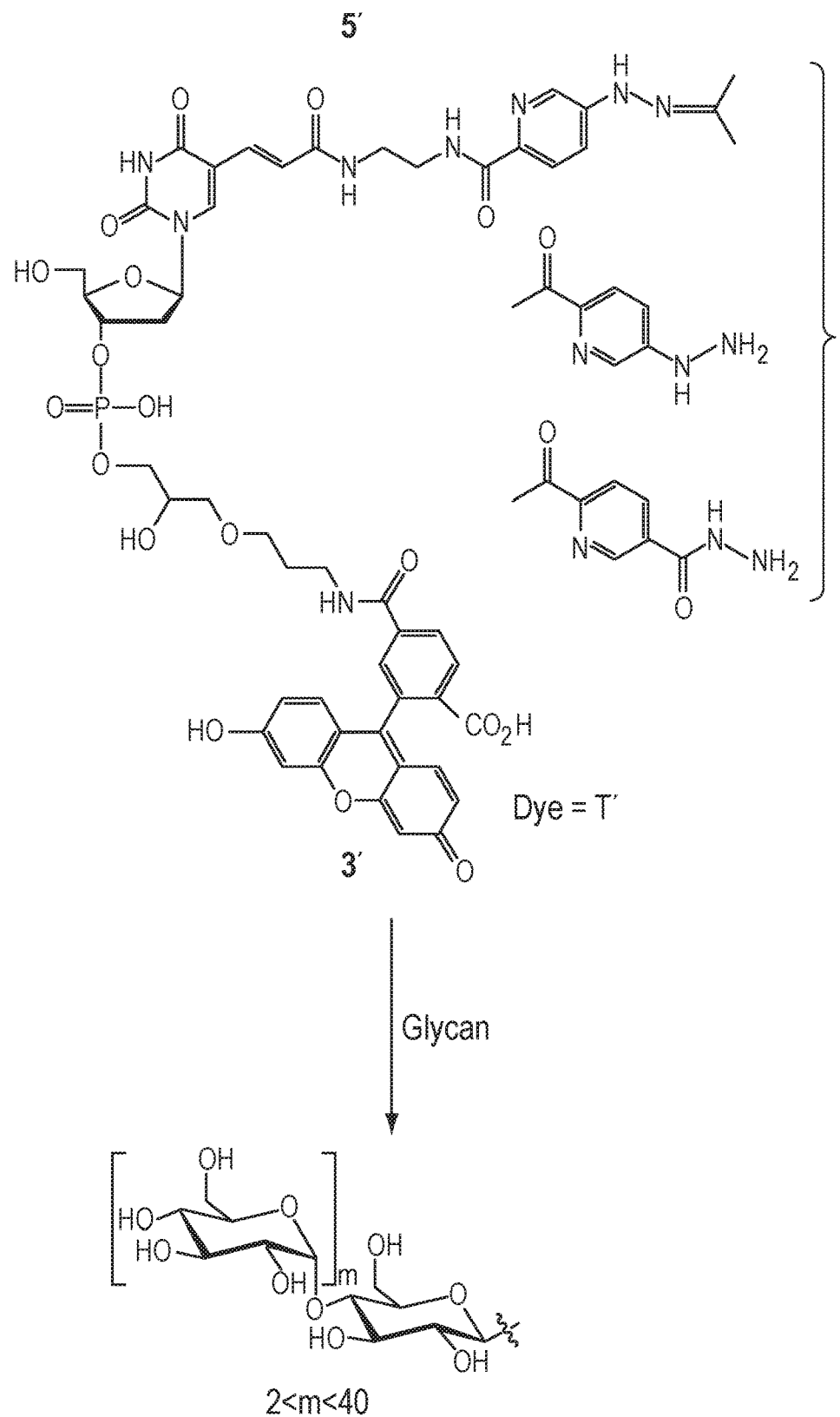
FIG. 9: Another exemplary schematic of a dye attached to the 3' end of a nucleic acid oligomer with linker added manually to the nucleotide base (instead of the sugar), and this labeled nucleic acid oligomer was then conjugated to a glycan.
Figure 10:
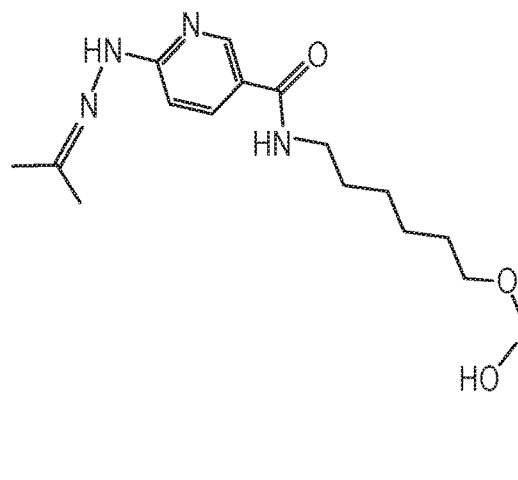
FIG. 10: Schematic of exemplary mobility modifiers (drag chutes) with exemplary dyes (as shown) attached at one end. The mobility modifiers may provide further drag and/or charge to a target molecule to be conjugated.
Figure 10:
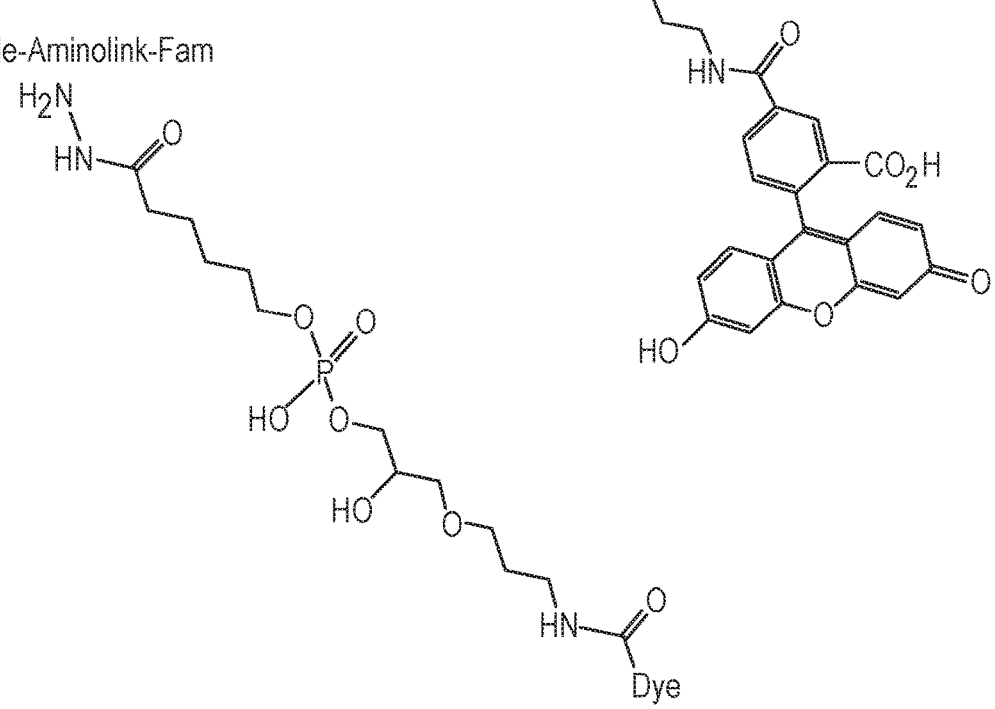
Figure 10:
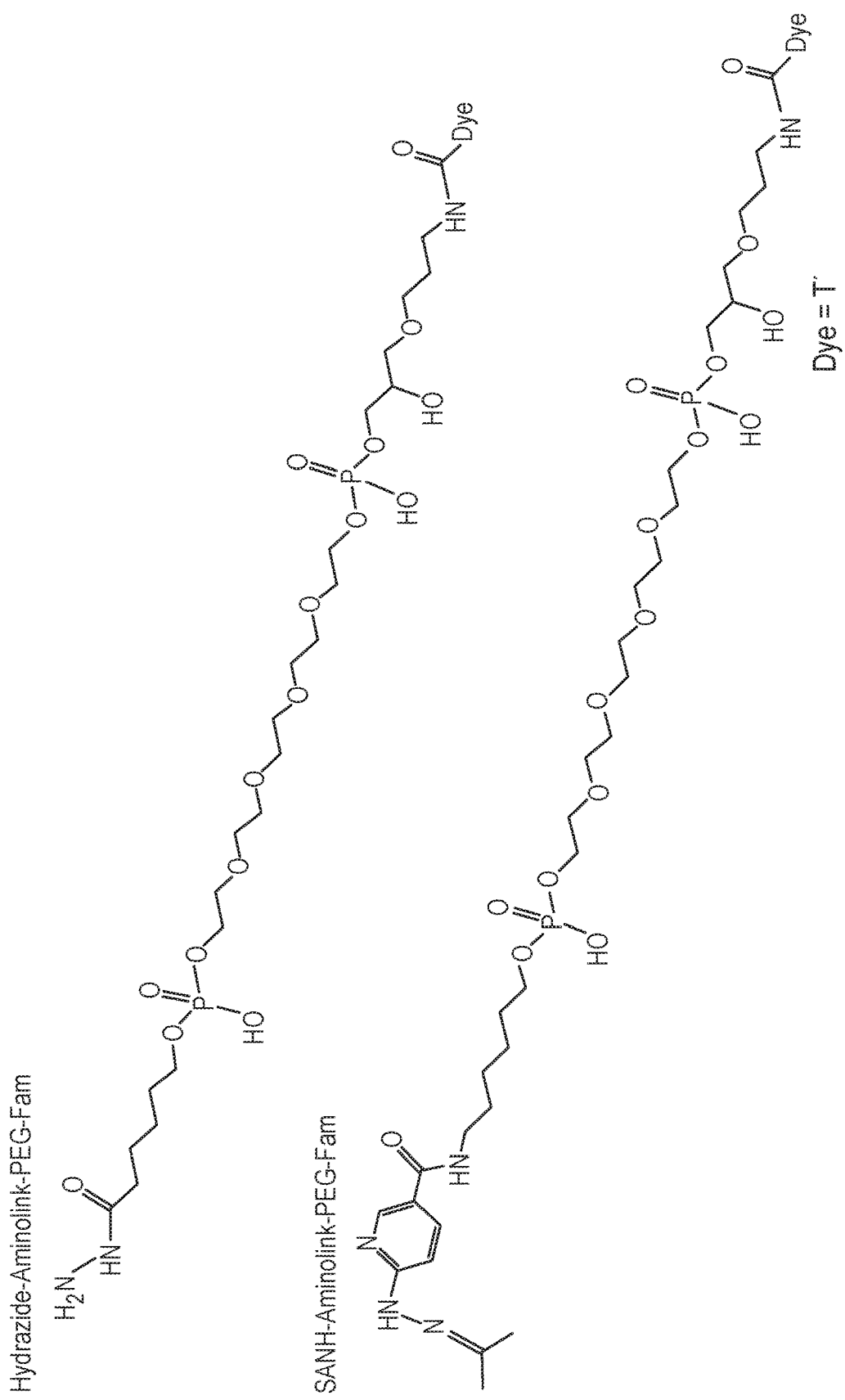
Figure 11:
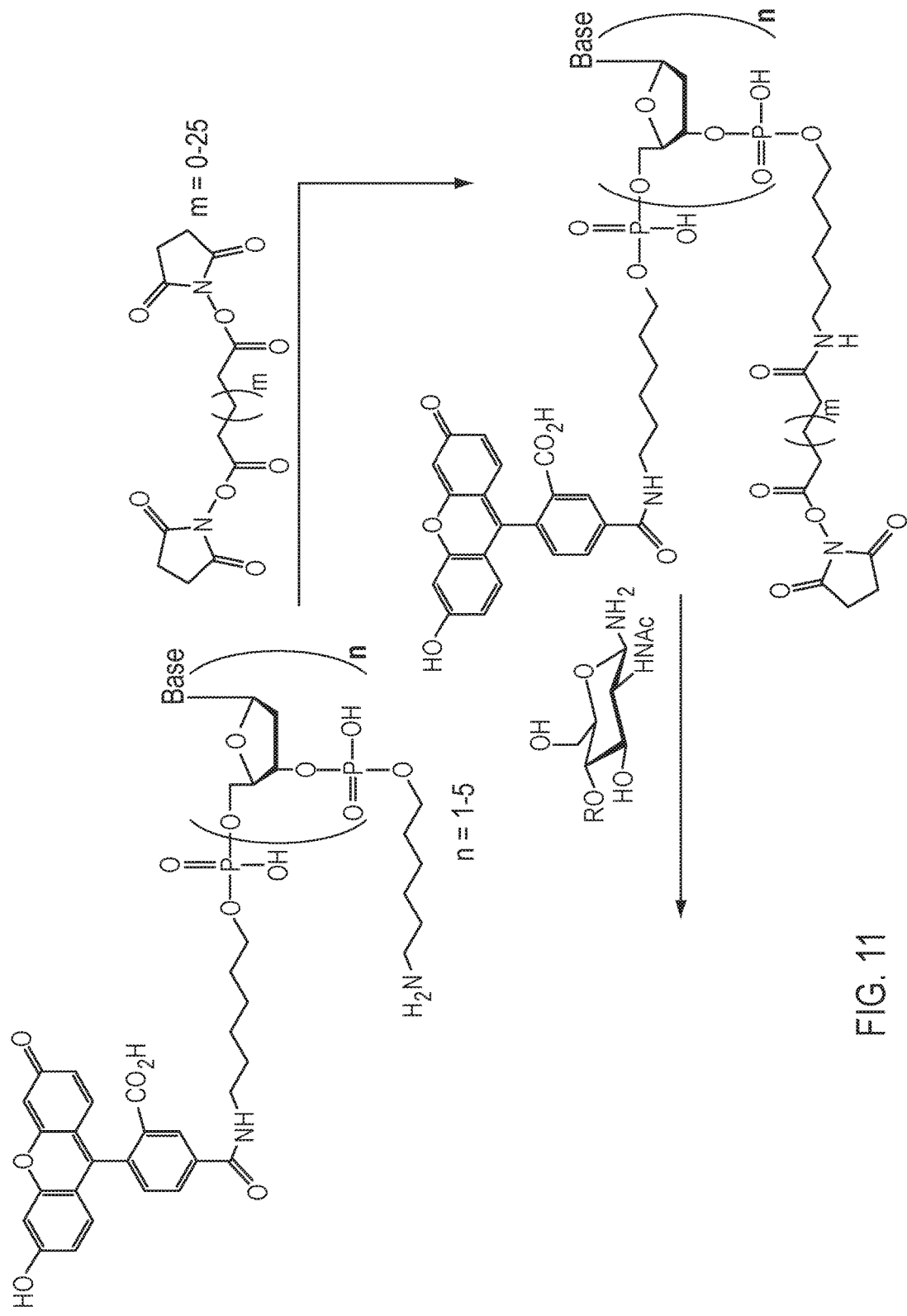
FIG. 11: Schematic of reactivity of an amino sugar instead of a reactive aldehyde. As shown here, a linker having an amino group at the 3' end is functionalized with a bis NHS ester to generate an amino-sugar conjugate.
Figure 11:
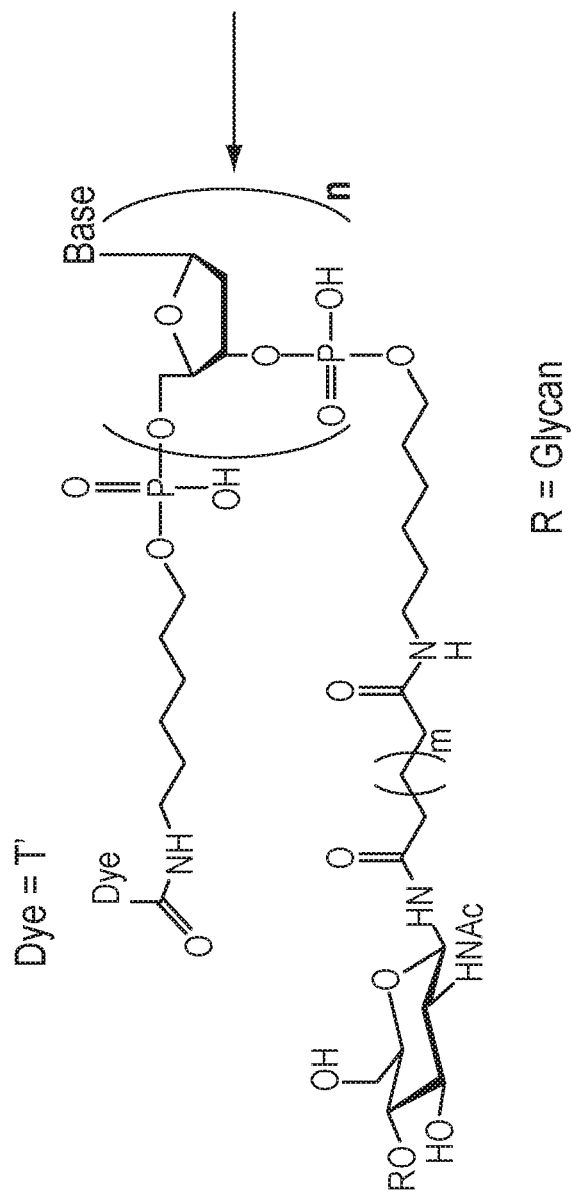
Figure 12:
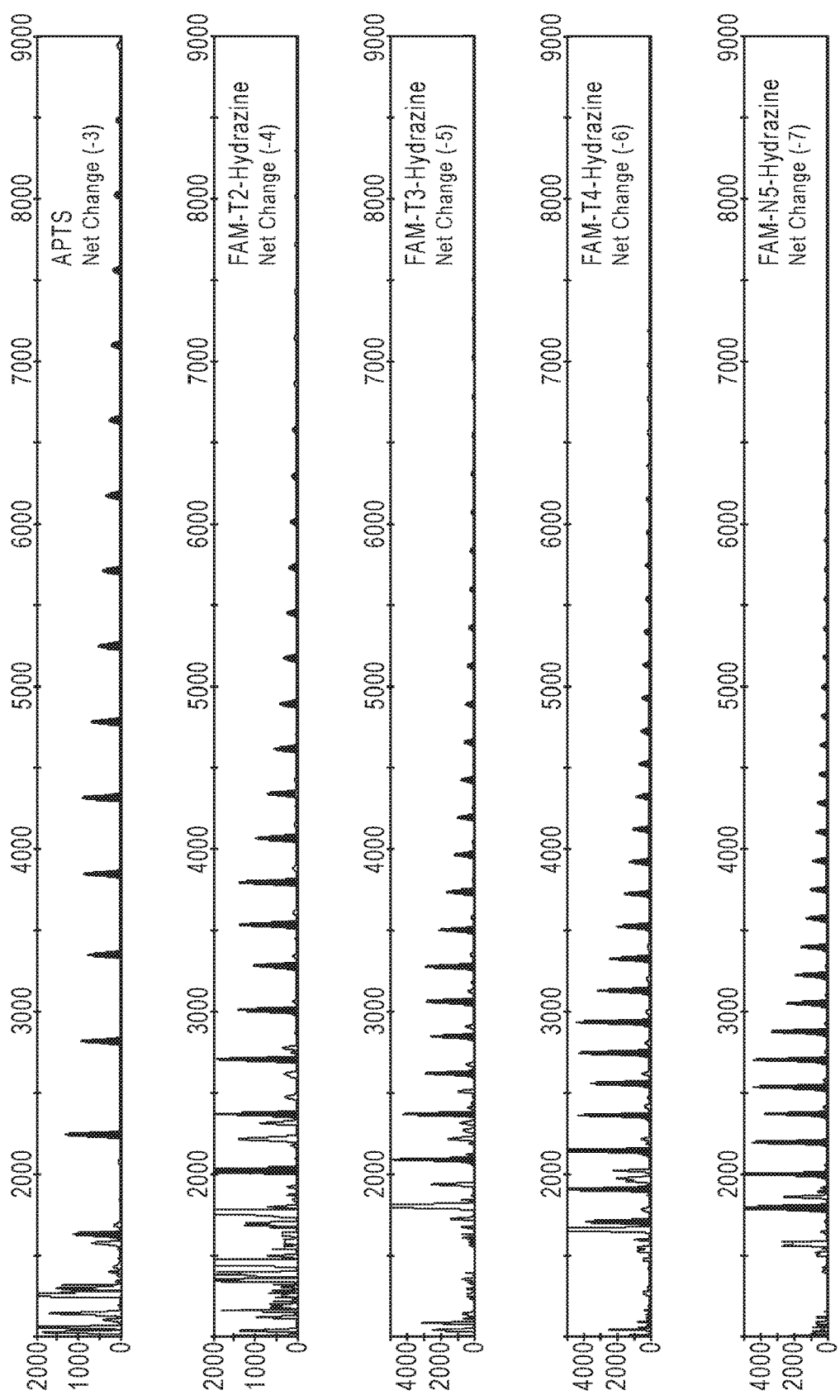
FIG. 12: CE separation of dextran ladders labeled with APTS (top panel) or with variable length fluorescent reactive nucleic acid probes of the general form 5'-FAM-$(T)_n$-hydrazine acetone.
Figure 13:
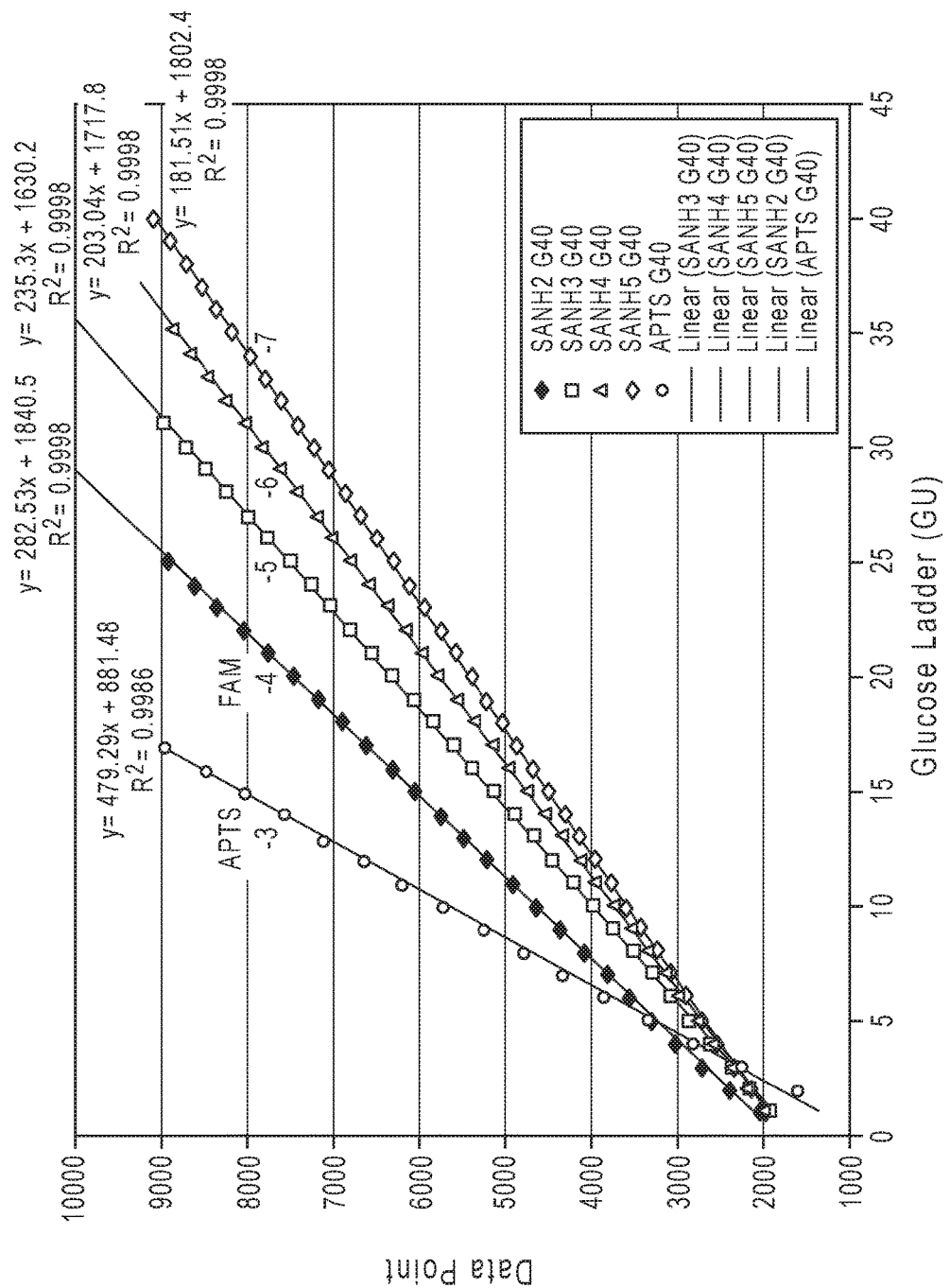
FIG. 13: Elution position in data points (y-axis) plotted against dextran polymer length (number of glucose units) for dextran ladders labeled with APTS (grey circles) or 5'-FAM-$(T)_n$-hydrazine (black), where n=2, 3, 4, or 5 nucleotides.
Figure 14:
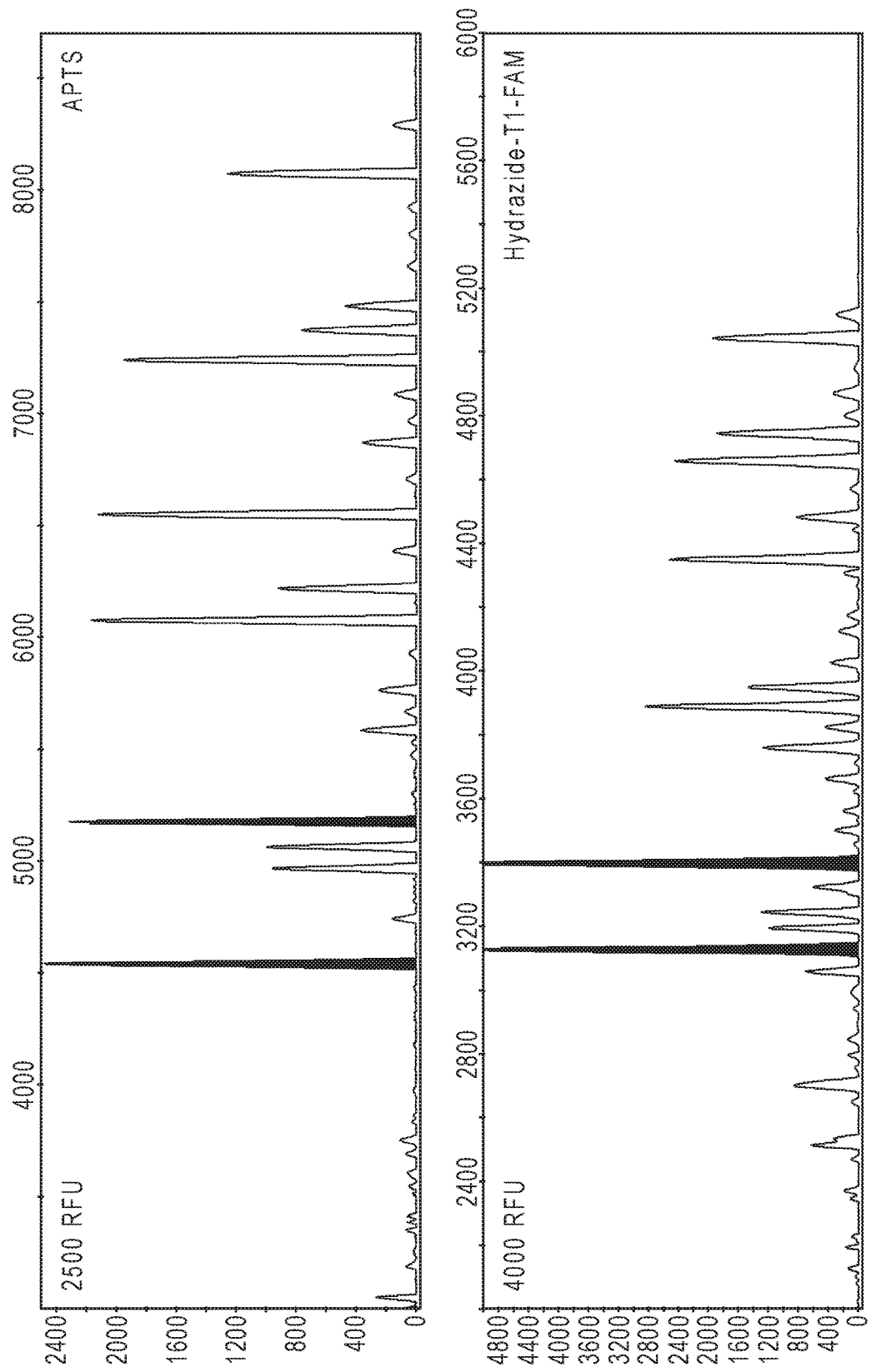
FIG. 14: Electropherograms showing APTS (top) or hydrazide-T1-FAM (bottom) labeled N-glycans derived from purified human serum IgGs. Filled peaks identify APTS (top) or hydrazide-T1-FAM labeled maltodextrin 7 and maltodextrin 8.
Figure 15:
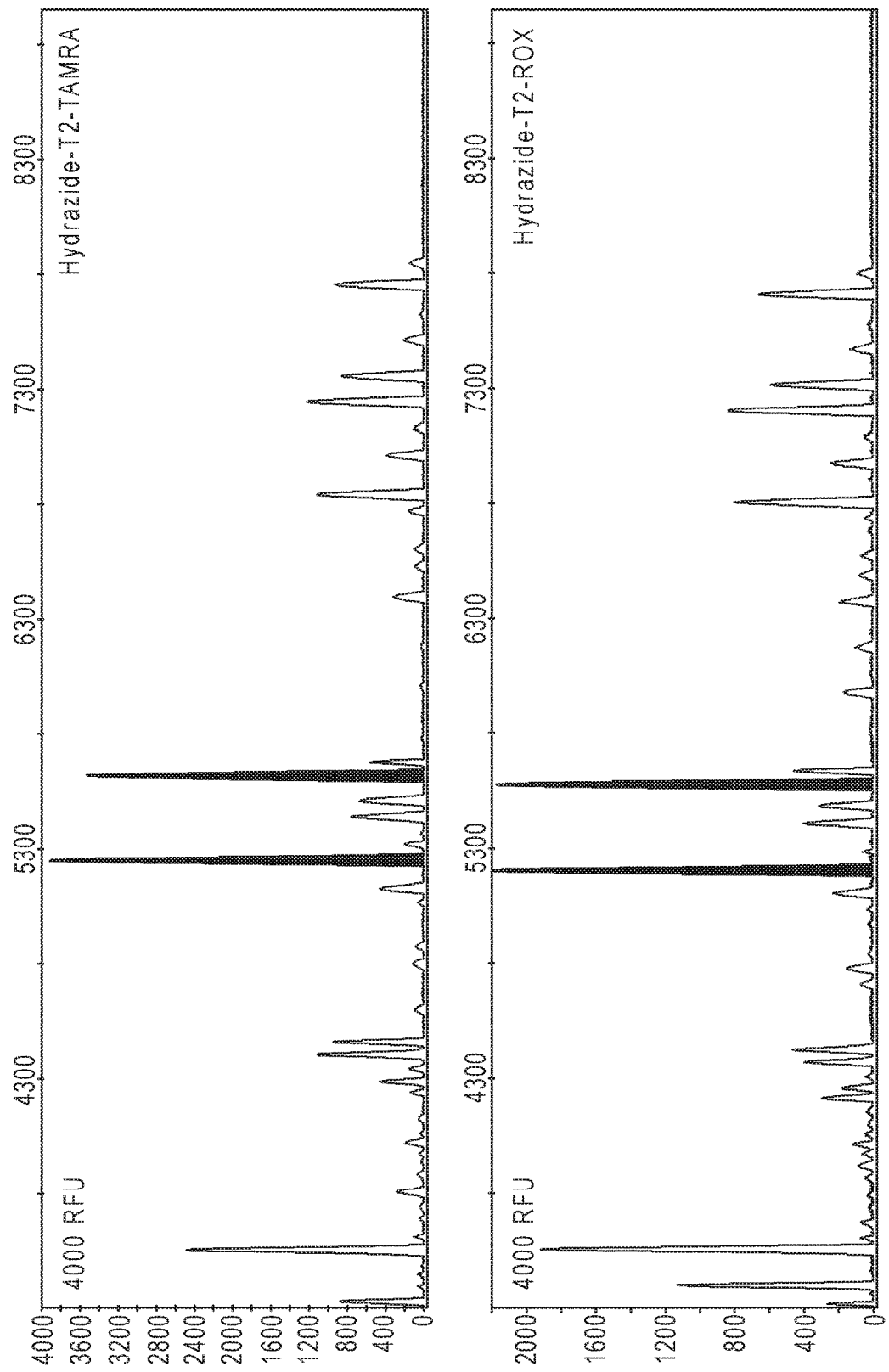
FIG. 15: Electropherograms showing hydrazide-T2-Tamra (top) and hydrazide-T2-Rox (bottom) labeled N-glycans derived from purified human serum IgGs. Filled peaks identify hydrazide-T2-Tamra (top) or hydrazide-T2-Rox (bottom) labeled maltodextrin 7 and maltodextrin 8.
Figure 16:
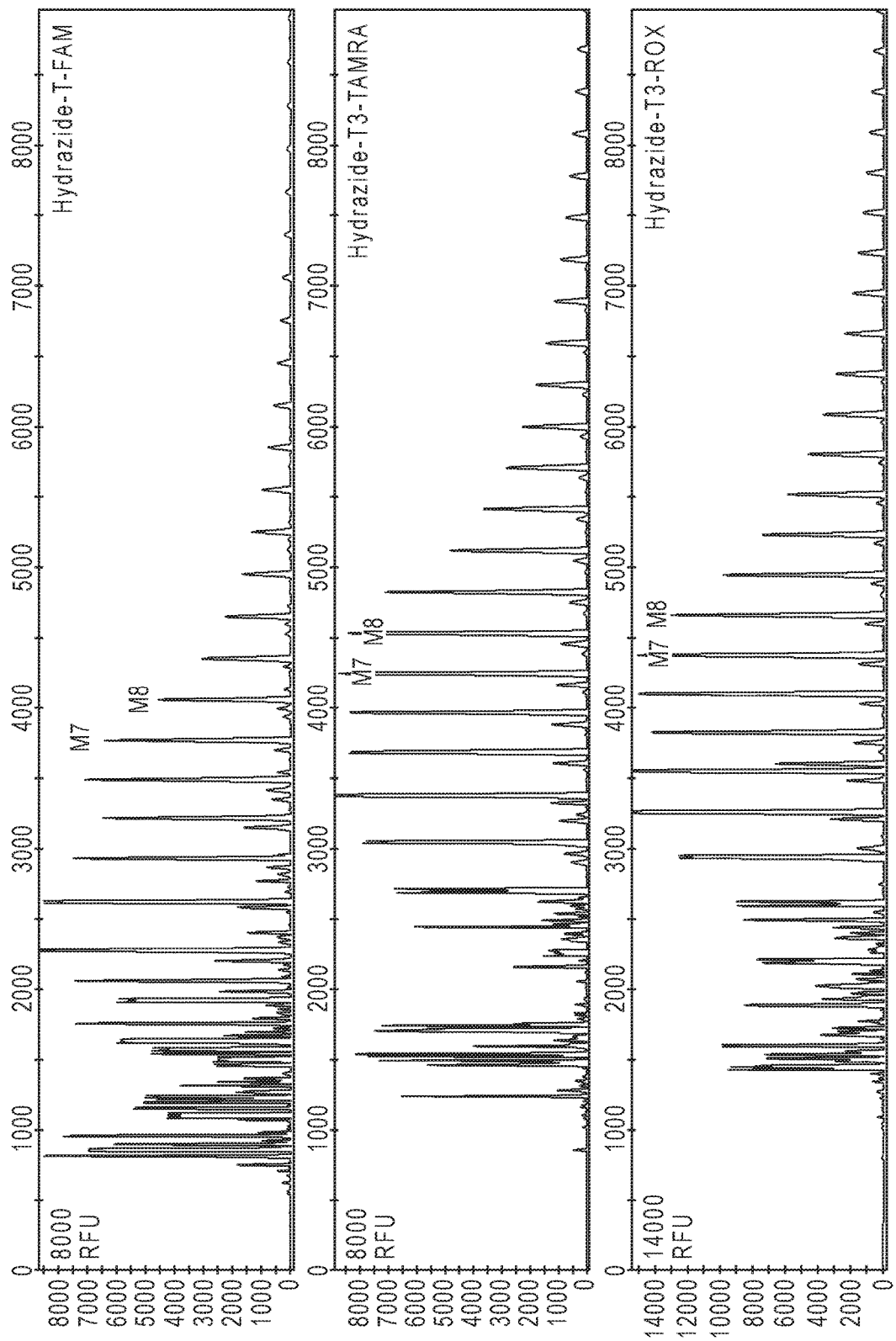
FIG. 16: Electropherograms showing maltodextrin ladders labeled with hydrazide-T1-FAM (top), hydrazide-T3-Tamra (middle), or hydrazide-T3-Rox (bottom). Maltodextrin 7=(M7) and Maltodextrin 8=(M8) and contain 7 or 8 glucose units, respectively.
Figure 17:
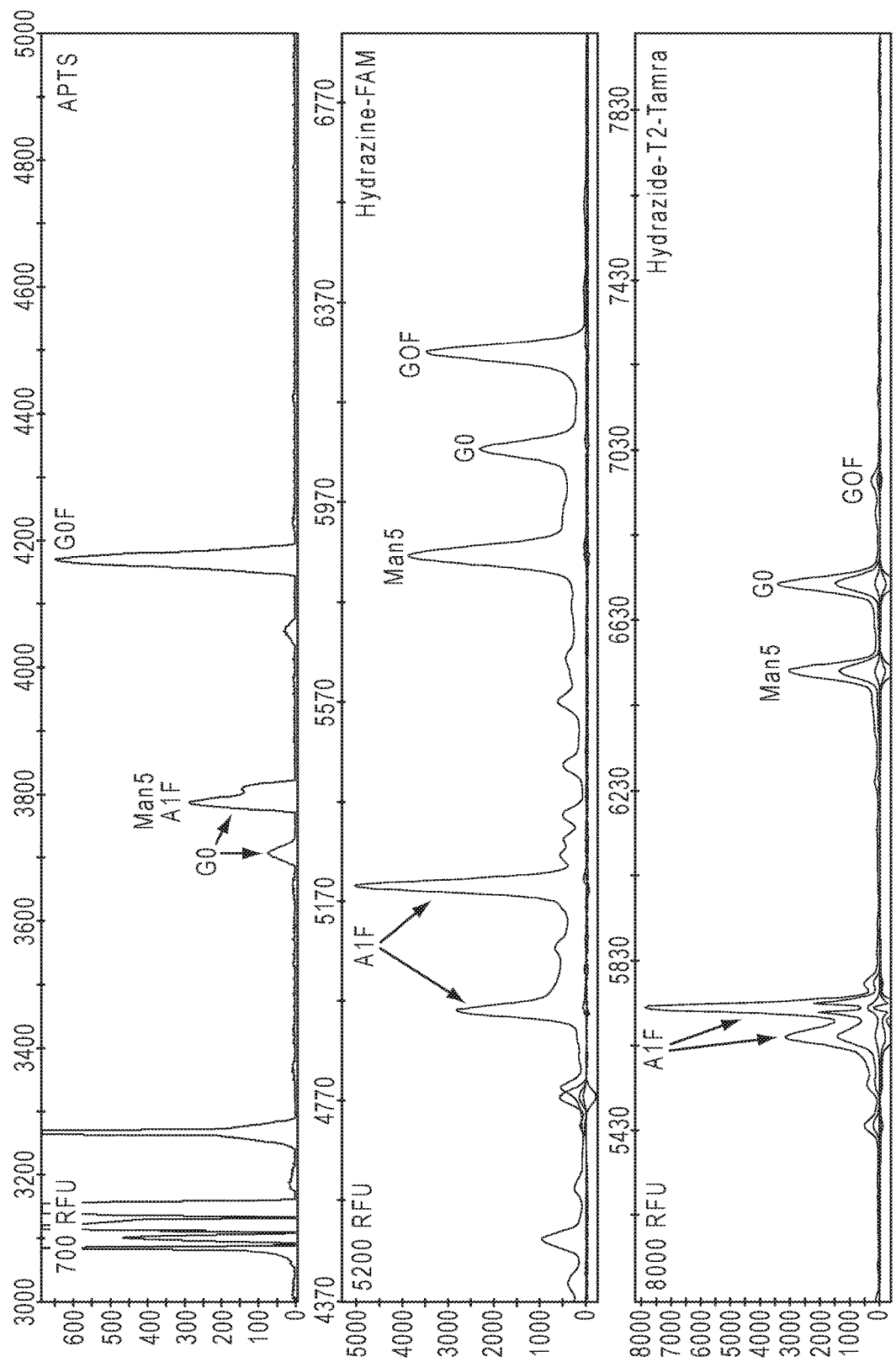
FIG. 17: Comparison of pure glycans A1F, Man5, G0, and G0F labeled with APTS (top), hydrazine-FAM (middle), and Hydrazide-T2-Tamra (bottom). Peaks unresolved by APTS labeling are well resolved when carrying hydrazine (middle), or hydrazide (bottom) functionalities. The reactive FAM construct (middle panel) lacks a nucleoside, and is listed as compound SANH-aminolink-FAM.
Figure 18:
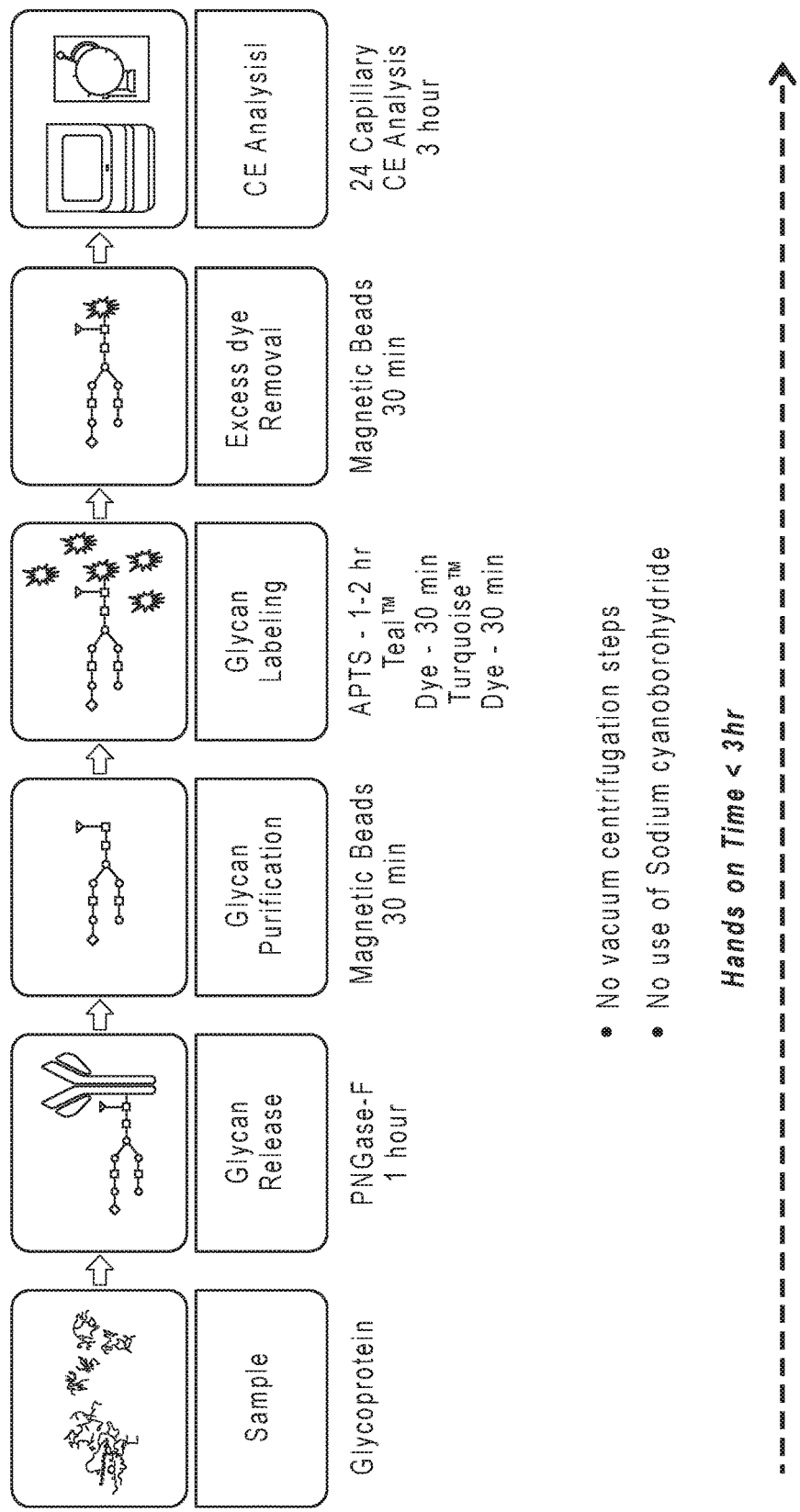
FIG. 18: Schematic of an exemplary workflow for glycan analysis according to certain embodiments disclosed herein.

According to various exemplary embodiments, N-linked glycans may be enzymatically cleaved using PNGase, and glycans may be fluorescently labeled at their reducing end with a modified dye directly (e.g., ALEXA FLUOR 448, etc.) containing either a hydrazide or oxyamine functional group (e.g., a carbonyl reactive group) on-line, in a 100 microliters sample well, or the cleaved glycans may be fluorescently labeled using the charged reactive oligomers (with or without linkers, further, with or without mobility modifiers), some of which have been exemplified in FIGS. 1-11. Labeling may involve the formation of a hydrazone between a sugar carbonyl and the fluorophore hydrazide or the formation of an oxime between the sugar carbonyl and the fluorophore hydroxylamine. The labeled glycans may inherit a negative charge due to sulfonic acids that may be in the dye, or through the charged reactive oligomers (with or without linkers, further, with or without mobility modifiers), and, as a result, they may migrate in any differential charge field, for e.g., an electric field. The labeled glycans can be separated, for e.g., by capillary gel electrophoresis and may be detected by fluorescence using, for example, a laser diode (e.g., 488 nm) for excitation and a CCD camera (including, e.g., a 510 nm bandpass filter) for detection. Detection may generate an electrophoretogram showing peaks representing individual glycans as they migrate paste the laser/detector. Exemplary electrophoretograms are shown in FIGS. 12-17. When an ALEXA FLUOR 448 dye is used, it may provide fluorescence at a sufficient linear range to be used quantitatively.

In various embodiments, the at least one glycan-cleaving enzyme may be immobilized on a bead. In some embodiments, immobilizing the at least one glycan-cleaving enzyme on a bead may provide less onerous cleavage reactions conditions, minimizing cross contamination, and may permit multiplexing of multiple samples or multiplexing different glycan cleavages exploiting differing specificities performed on several aliquots of the same sample. In some embodiments, the bead may be a magnetic bead, which may further aid in simplifying handling of the sample during cleavage of the at least one glycan from the biomolecule or glycoconjugate.

Labeling Species.

In various embodiments, the at least one cleaved glycan may be labeled with a labeling species to produce at least one labeled glycan. The type of labeling species may be selected based on the choice of detection mode employed. For example, if visible detection is chosen, the labeling species may include a visible dye tag. In another example, labeling species that include a fluorescent tag, may permit detection by fluorescence. In some embodiments, the labeling species may confer charge to the at least one glycan by including charged moieties. Since the at least one glycan typically may have no net charge, introduction of charge may not permit the use of differing types of electrophoretic separation modes for the at least one labeled glycan.

Alternatively, a labeling species having no charge can still provide a labeled glycan that may be detected by being migrated in a channel under the influence of an electric field, using differing techniques. For example, CE separation may be performed at near-zero electroosmotic flow in a channel having no sieving polymer with a suitable electrolyte as a running buffer and may further provide a hydrophilic coating to the channel to optimize migration of the neutral labeled glycan.

In various embodiments, the labeling species may be charged. In other embodiments, the labeling species may be uncharged. A labeling species may include a reactive nucleic acid, a dye, a fluorescence quencher moiety, or a mobility modifying moiety. In some embodiments, the labeling species includes more than one of a reactive nucleic acid, a dye, a fluorescence quencher moiety, or a mobility modifying moiety. The labeling species includes a reactive moiety, which may be selected from an oxime, a hydrazide, a hydrazine, a phosphine, an azide, an alkyne, or an amine. The reactive moiety may be configured to react with the at least one glycan to form a covalent bond. In various embodiments, the reactive moiety reacts with the at least one glycan to form a covalent bond that does not require further chemical modification with a reducing agent such as sodium cyanoborohyride and the like. Borohydride reducing agents may cause other unwanted modification of the at least one glycan. When the labeling species is a reactive nucleic acid or a mobility modifying moiety, then the labeling species may further include a tag including a dye, a biological reporter molecule, a gold nanoparticle, a semiconductor nanocrystal, for example, a quantum dot, or a spin label.

In various embodiments, the labeling species has a structure of the following formula: T-$L_1$-RM, where T may be a tag; $L_1$ may be a linker linking the tag to the reactive moiety and RM may be the reactive moiety. In various embodiments, the labeling species may have a structure of the following formula:
T-OLIGO-RM, where T may be a tag, and OLIGO-RM may be a reactive nucleic acid. The labeling species of this class may further have a structure of the following formula: T-$L_1$-OLIGO-$L_2$-RM, where T may be a tag; $L_1$ may be a linker linking the tag to the oligo portion of the reactive nucleic acid; and $L_2$ may be a linker linking the oligo to the reactive moiety of the reactive nucleic acid label species. $L_1$, $L_m$, and $L_2$ linkers are each independently a single covalent bond or a series of stable covalent bonds incorporating 1-50 nonhydrogen atoms selected from the group consisting of C, N, O, S and P that covalently attach the fluorogenic or fluorescent compounds to another moiety such as a chemically reactive group or a biological and non-biological component. Exemplary linking members may include a moiety that includes —C(O)—, —C(O)NH—, —C(O)O—, —NH—, —S—, —O—, —OP(O)O—, —S(O)$_2$— and the like, and may be further substituted by one or more carboxylate, sulfonate, or phosphate groups. $L_1$, $L_m$, and $L_2$ linkers may be -alkyl, -substituted alkyl-, -alkenyl-, -substituted alkenyl-, -carboxamidyl-, substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-linkers.

In other embodiments, the labeling species has a structure of the following formula: T-MM-RM, where T may be a tag; MM may be a mobility modifier moiety; and RM may be a reactive moiety. In other embodiments, the labeling species has a structure of the following formula: MM-RM, where MM may be a mobility modifier moiety; and RM may be a reactive moiety. In various embodiments, the labeling species has a structure of one of the following formulae: MM-$L_2$-RM or T-$L_1$-MM-$L_2$-RM, where T may be a tag; $L_1$ may be a linker linking the tag to MM; MM may be a mobility modifier moiety; $L_2$ may be a linker linking the mobility modifier moiety to the reactive moiety of the labeling species; and RM may be a reactive moiety. $L_1$, $L_m$, and $L_2$ linkers are defined as above.

In various embodiments, the labeling species has a structure of the following structure: T-MM-OLIGO-RM, where T may be a tag; MM may be a mobility modifier moiety; OLIGO may be a nucleic acid portion of a reactive nucleic acid; and RM may be a reactive moiety of the reactive nucleic acid. In yet other embodiments, the labeling species has a structure of the following formula: T-$L_1$-MM-$L_m$-OLIGO-$L_2$-RM, where T may be a tag; $L_1$ may be a linker linking the tag to MM; MM may be a mobility modifier moiety; $L_m$ may be a linker linking the mobility modifier moiety to the nucleic acid portion of a reactive nucleic acid; $L_2$ may be a linker linking the nucleic acid portion to the reactive moiety of a reactive nucleic acid label species; and RM may be a reactive moiety. $L_1$, $L_m$, and $L_2$ linkers are defined as above.

Reactive Moiety.

Reactive functional groups include those used to prepare bioconjugates, e.g., phosphoramidites, N-hydroxysuccinimide esters, maleimides and the like. In various embodiments, a reactive moiety may be an oxime, a hydrazide, a hydrazine, a sulfahydryl, a phosphine, an azide, an alkyne, or an amine, an aminooxy, or a combination thereof, which can react with a glycan, a protein, a lipid, or any part of a biomolecule. Methods to prepare each of these functional groups are well known in the art and their application to or modification for a particular purpose is within the ability of one of skill in the art (see, for example, Sandler and Karo, (eds.), ORGANIC FUNCTIONAL GROUP PREPARATIONS, Academic Press, San Diego, 1989). In other embodiments, a reactive moiety may be an acrylamide, an activated ester of a carboxylic acid, an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine, a hydrazide, an imido ester, an isocyanate, an isothiocyanate, a maleimide, a phosphoramidite, a reactive platinum complex, a sulfonyl halide, a thiol group, or a photoactivatable group, wherein such moieties may react with substrates including but not limited to solid substrates, polymers, or conjugates including tags such as dyes.

Dyes.

A dye may be a visible dye, a fluorescent dye, or a chemiluminescent dye. In various embodiments, the fluorescent dye may be a pyrene dye, a naphthalene dye, an aminopyridine dye, a xanthene dye which may be a fluorescein, rhodol or rhodamine dye, a cyanine dye, a coumarin dye, a borapolyazaindacine dye, a benzofuran dye, or an indole dye. In some embodiments, the fluorescent dye may be aminopyrene trisulfonic acid (APTS). In other embodiments, the fluorescent dye may be a fluorescein dye or a rhodamine dye. In various embodiments, more than one dye may be incorporated in the labeling species. When more than one dye may be incorporated in the labeling species, the fluorescent dye may be a polymeric dye or an energy transfer dye. An energy transfer dye may have a donor dye and an acceptor dye, where the donor dye may be configured to absorb energy at one wavelength and emit energy at a second wavelength which emitted energy excites the acceptor dye at the second wavelength. The acceptor dye then emits at a third wavelength, which may be detectable. If more than one labeling species may be used in a glycan detection assay where more than one energy transfer dye may be used to label various different glycans, then the more than one energy transfer dyes are configured to be detected at different wavelengths, and therefore are spectrally resolvable.

In other embodiments, the energy transfer dye may be attached to the linker at the same point of attachment, i.e. may be attached at one atom of the labeling species. In other embodiments, the energy transfer dye may be attached to different atoms in the labeling species, while still being configured to donate and accept excitation energy for energy transfer dye performance.

In other embodiments, the labeling species may be labeled with a quencher dye which may be configured to quench fluorescence of a fluorescent dye. In yet other embodiments, the labeling species may contain a fluorescent dye and a quencher dye.

Fluorescent Dye Tags.

The labeling species may have a structure of any one of the following: T-$L_1$-RM; T-OLIGO-RM; T-$L_1$-OLIGO-$L_2$-RM; T-MM-RM; T-$L_1$-MM-$L_2$-RM; T-MM-OLIGO-RM; and: T-$L_1$-MM-$L_m$-OLIGO-$L_2$-RM, which include a fluorescent dye tag T.

In certain embodiments, T includes, but are not limited to, FAM™, JOE™, VIC™, HEX™, TET™, NED™, PET®, TAMRA™, ROX™, R110, R6G, Texas Red®, aminopyrene trisulfonic acid (APTS), NBD, BigDye™, or a tautomer or salt thereof, or a combination thereof.

In certain embodiments T is:

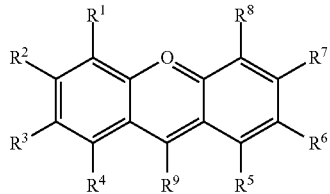

Formula $T^1$ or a tautomer or salt thereof;
wherein $R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonyl-amino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and
one of $R^1$, $R^2$, $R^3$, $R^4$, $R^5$, $R^6$, $R^7$, $R^8$ and $R^9$ is the point of attachment to $L_1$ through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In some embodiments, $R^9$ may be a substituted aryl. In yet other embodiments, the substituted aryl $R^9$ is substituted with two halo substituents, which may be the same or different halide. In other embodiments, the two halo substituents are each chloro. In yet other embodiments, the substituted aryl $R^9$ has two halo substituents and a third substituent is the point of attachment to $L_1$ through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-. In some embodiments, at least one $R^9$ substituent is a covalent bond, -alkyl-, -substituted alkyl-, -carboxamidyl-, substituted carboxamidyl-, -carbonyl-, -substituted carbonyl-, -alkoxy-, -substituted alkoxy-, -sulfonamidyl-, or -substituted sulfonamidyl-. In yet other embodiments, the at least one $R^9$ substituent is a covalent bond, -carboxamidyl-, substituted carboxamidyl-, -carbonyl-, -substituted carbonyl-, -alkoxy-, -substituted alkoxy-, -sulfonamidyl-, or -substituted sulfonamidyl-.

In certain embodiments, T is:

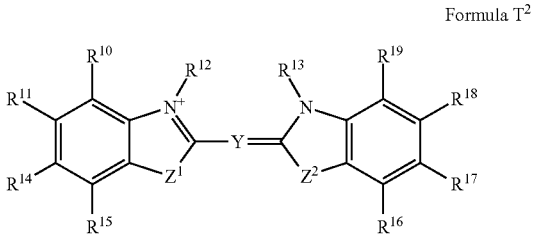

Formula $T^2$ or a tautomer or salt thereof;
wherein, $Z^1$ and $Z^2$ are each independently O, S, $NR^{23}$ or $CR^{24}R^{25}$;
Y is —$CR^{20}$=$(CR^{21}$—$CR^{22}$=$)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and
one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, T is:

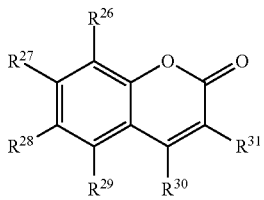

Formula T³ or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, T is:

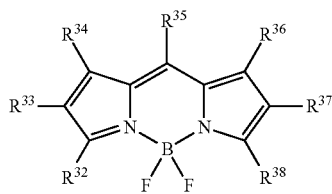

Formula T⁴ or a tautomer or salt thereof;
wherein $R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, T is:

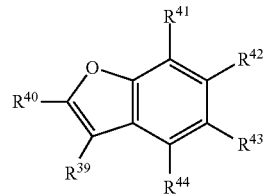

Formula T⁵ or a tautomer or salt thereof;
wherein $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, T is:

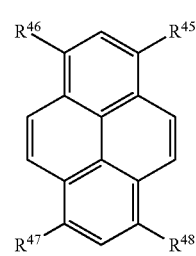

Formula T⁶ or a tautomer or salt thereof;
wherein $R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a compound of Formula $T^1$ has the structure of formula $T^{1a}$ or a tautomer or salt thereof is provided:

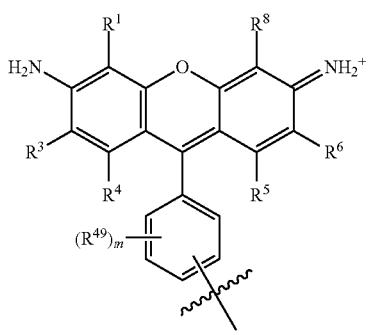

(T$^{1a}$)

wherein

is the point of attachment to $L_1$ through a moiety as defined above for the compound of Formula $T^1$;

$R^1$, $R^3$, $R^4$, $R^5$, $R^6$, and $R^8$ are each as defined for Formula $T^1$ and $R^{49}$ is independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2.

In certain embodiments, $R^1$ and $R^8$ are each sulfo; $R^2$, $R^3$, $R^4$, $R^5$, $R^6$, and $R^7$ are each H; $R^{49}$ is carboxy; and m is 1.

In certain embodiments, a compound of Formula $T^2$ has a structure of Formula $T^{2a}$ or a tautomer or salt thereof:

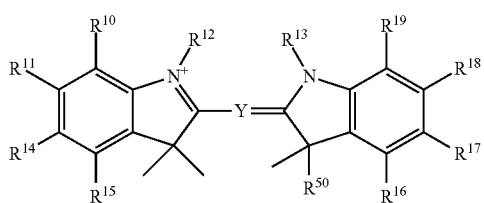

(T$^{2a}$)

wherein,

Y is $-CR^{20}=(CR^{21}-CR^{22}=)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and where one of $R^{13}$ or $R^{50}$ is

, where

is the point of attachment to $L_1$ through a moiety as defined above for the compound of Formula $T^2$.

In certain embodiments, $R^{50}$ is alkyl.

In certain embodiments, a compound of Formula $T^6$ has a structure of Formula $T^{6a}$ or a tautomer or salt thereof:

Formula T$^{6a}$

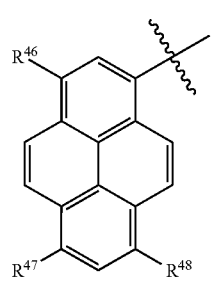

Wherein wherein

is the point of attachment to $L_1$ through a moiety as defined above for the compound of Formula $T^{6a}$; and $R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

Suitable detectable labels include, for example, fluorosceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC; Alexa Fluors® (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels can also be used (see, e.g., US Pub. No. 2009/0197254), as would be known to those of skill in the art.

Fluorescent Labeling Species.

In various embodiments, a labeling species having a fluorescent dye tag of structure T-$L_1$-RM may be provided, having a structure of Formula (I) or a tautomer or salt thereof:

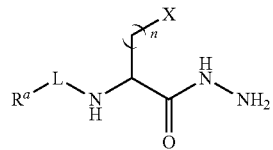

wherein L is a linker;

$R^a$ is a reporter molecule;

n is an integer from 1 to 24; and

X is a molecule containing $SO_3H$, $SO_3^-$, $OPO_3^{2-}$, $OP_3H_2$, $PO_3H_2$, $PO_3^{2-}$, COOH, or $COO^-$.

In certain embodiments, L is a covalent bond, -alkyl-, -substituted alkyl-, -alkenyl-, -substituted alkenyl-, -carboxamidyl-, substituted carboxamidyl-, -heterocyclyl-, -substituted hetero-cyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino- In certain embodiments, $R^a$ is a dye. More particularly, the dye may be a pyrene, a xanthene, a cyanine, an indole, a benzofuran, a coumarin, or a borapolyazaindacine.

In certain embodiments, the compound of Formula (I) is a salt. More particularly, the salt may include a potassium or sodium ion.

In one aspect, tag compounds are provided selected from the group consisting of:

Compound 1

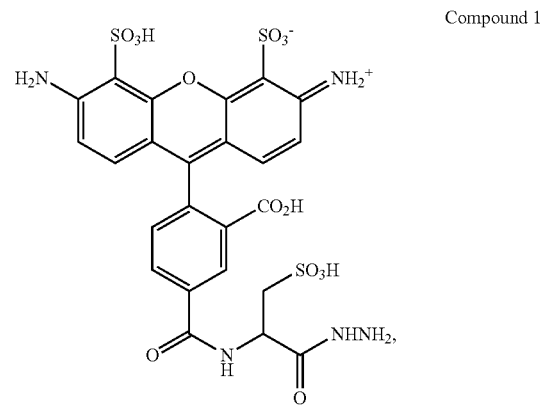

Compound 2

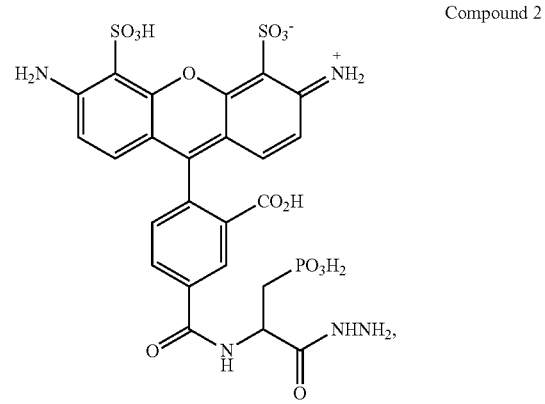

Compound 3

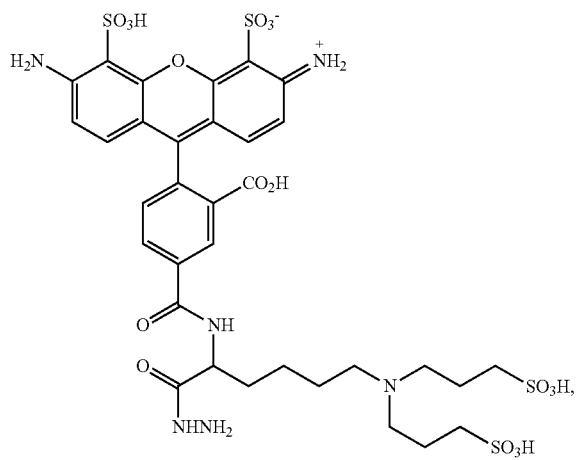

Compound 4

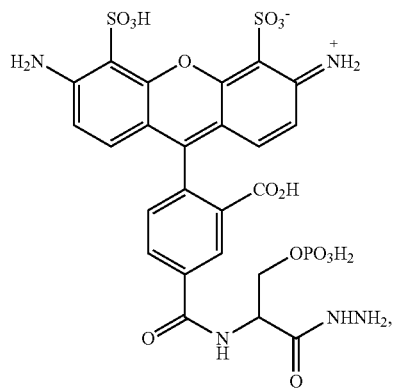

Compound 5

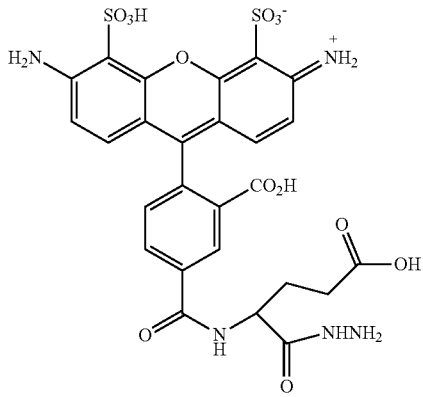

Compound 6

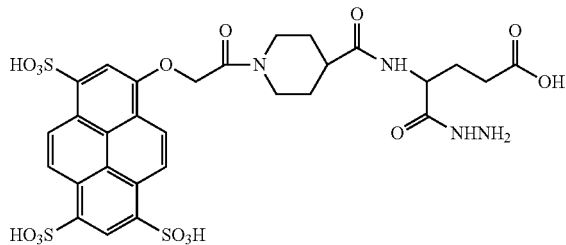

and

Compound 30

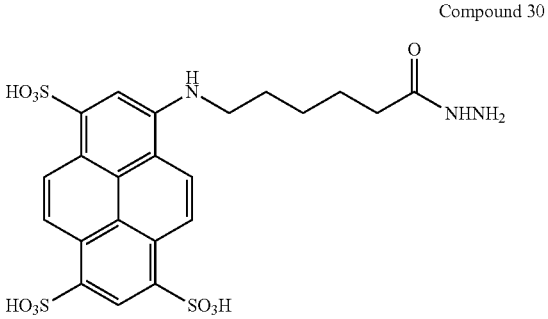

Reactive Nucleic Acids.

In various embodiments, the labeling species may include a reactive nucleic acid, which may have a formula of any one of $T-L_1$-OLIGO-$L_2$-RM; OLIGO-$L_2$-RM; MM-$L_m$-OLIGO-$L_2$-RM; or $T-L_1$-MM-$L_m$-OLIGO-$L_2$-RM, as defined above. The OLIGO portion of the reactive nucleic acid may be DNA, RNA, nucleotide analogs, or a combination thereof. OLIGO may include non-natural internucleosic bonds, and/or non-natural nucleobases. The OLIGO may have a length of about 1 nucleotide to about 50 nucleotides in length. In some embodiments, the OLIGO has a length of about 1 nucleotide to about 5 nucleotides in length or about 2 nucleotides to about 5 nucleotides in length. In some other embodiments, the OLIGO has a length of about 1 nucleotide to about 10 nucleotides in length. In various embodiments, the OLIGO may be about 3 nucleotides, about 5 nucleotides, about 10 nucleotides, about 15 nucleotides or about 20 nucleotides in length. In yet other embodiments, the OLIGO has a length of about 20 nucleotides to about 50 nucleotides. The reactive moiety may be any one of the reactive moieties as described above. The reactive moiety may be attached to the nucleic acid OLIGO portion of the reactive nucleic acid via linker $L_2$ at a position selected from a 3' position of a terminal deoxyribose/ribose, a 5' position of a terminal deoxyribose/ribose, a 2' position of a terminal deoxyribose/ribose, or a nucleobase of the reactive nucleic acid. The label T may be attached to the nucleic acid OLIGO portion of the reactive nucleic acid via linker $L_1$ at a position selected from a 3' position of a terminal deoxyribose/ribose, a 5' position of a terminal deoxyribose/ribose, a 2' position of a terminal deoxyribose/ribose, or a nucleobase of the reactive nucleic acid. The label T can also be attached on the base via linker $L_1$ at any base in the DNA. The labeling species having a reactive nucleic acid may further include a mobility modifying moiety MM, when the labeling species has a formula of MM-$L_m$-OLIGO-$L_2$-RM or $T-L_1$-MM-$L_m$-OLIGO-$L_2$-RM. When a mobility modifying moiety may be included, the mobility modifying moiety may be attached to the nucleic acid OLIGO portion via linker $L_m$ at a position selected from a 3' position of a terminal deoxyribose/ribose, a 5' position of a terminal deoxyribose/ribose, a 2' position of a terminal deoxyribose/ribose, or a nucleobase of the reactive nucleic acid.

Other Labels.

In some embodiments, T may be a semiconductor nanocrystal, such as a quantum dot. In some embodiments, the quantum dot may be a Qdot®, available from Thermo Fisher Scientific. In other embodiments, T may be selected from a radiolabel, a metal ion or metal ion containing substance, a phosphor, or a fluorogen. Each of these species may be attached via linker $L_1$ as defined above to the remainder of the labeling species.

Biological Reporter Molecules.

In certain embodiments, T may be a chelating moiety, a hapten, an antibody, an enzyme, a bioluminescent substance, a chemiluminescent substance. More particularly, T may be avidin, streptavidin or an analog thereof. The biological reporter molecule T may be attached via linker $L_1$ as defined above to the remainder of the labeling species, which may further include a mobility modifying moiety and or OLIGO portion of a labeling species.

Mobility Modifying Moiety.

In various embodiments, the labeling species has a formula of one of following formulae: $MM\text{-}L_2\text{-}RM$; $T\text{-}L_1\text{-}MM\text{-}L_2\text{-}RM$; $MM\text{-}L_m\text{-}OLIGO\text{-}L_2\text{-}RM$; or $T\text{-}L_1\text{-}MM\text{-}L_m\text{-}OLIGO\text{-}L_2\text{-}RM$, where T, $L_1$, $L_m$, OLIGO, $L_2$ and RM are as defined above. A mobility-modifying moiety may be included to change the effective size or charge of the at least one labeled glycan, which can then change the mobility of the at least one labeled glycan when it subjected to migration under the influence of an electric field in order to separate and select it. A mobility modifying moiety contains polymeric units, which may have no charge, which may impart an effective "larger" size to the labeled glycan as it adds molecular weight without adding any charge, thus slowing the labeled glycan's rate of migration when subjected to migration under the influence of an electrical field. In other embodiments, the polymeric mobility modifying moiety may incorporate one or more charges which may speed or inhibit the rate of migration of the labeled glycanm depending on the nature and size of the net charge of the at least one labeled glycan.

Some non-limiting examples of mobility modifying containing labeling species as follows:

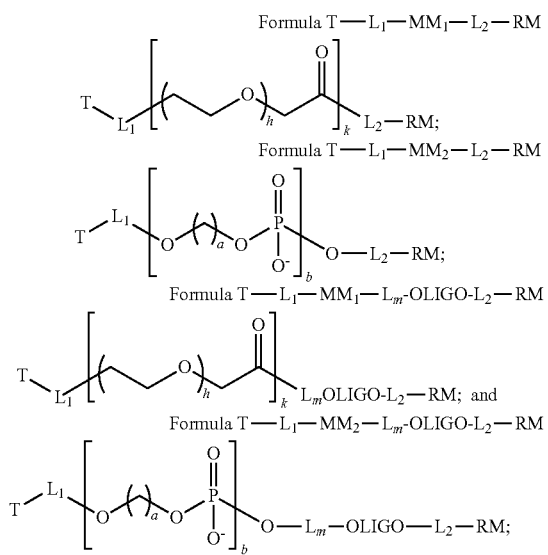

where $T_1$, $L_1$, $L_m$, $L_2$, OLIGO and RM are as defined above; and a may be an integer of about 2 to about 10; b may be an integer of about 1 to about 20; h may be an integer of about 1 to about 10; and k may be an integer of about 1 to about 15. The labeling species incorporating mobility modifying moiety $MM_1$ has no charge added by its incorporation and $MM_1$ imparts an effective larger size to the labeled glycan incorporating such mobility modifying moiety. In some embodiments, h may be about 3 to about 6 and k may be about 1 to about 10. $L_m$ may be attached to the OLIGO portion of the labeling species, when present, at a 3' position of a terminal deoxyribose/ribose, a 5' position of a terminal deoxyribose/ribose, a 2' position of a terminal deoxyribose/ribose, or a nucleobase of the reactive nucleic acid. The labeling species incorporating mobility modifying moiety $MM_2$ has additional positive charges added by its incorporation and may impart an altered size to charge ratio to the labeled glycan incorporating such mobility modifying moiety, depending on the nature and number of charges already present in the glycan labeled with a labeling species incorporating $MM_2$. Not shown, but also envisioned are mobility modifying moieties which add positive charges to the labeled glycan such as polymeric species including amines, amino acids, and the like.

Purification of the Cleaved and/or Labeled Glycan.

The at least one labeled glycan may be purified after the labeling reaction and prior to detecting the at least one labeled glycan. In some embodiments, the at least one labeled glycan may be purified using purification beads. The beads may be charcoal beads, or size exclusion beads, or any suitable material. In some embodiments, the purification beads may be magnetic. In other embodiments, the at least one labeled glycan may be purified using a spin column to separate the at least one labeled glycan from the reagents used to label the glycan. In some embodiments, Lectin molecules may be used to bind different sugar molecules tightly and assist in purification. For examples, concanavalin A binds α-D-mannosyl and α-D-glucosyl residues, and branched α-mannosidic structures (high α-mannose type, or hybrid type and biantennary complex type N-Glycans). Lentil lectin binds to fucosylated core regions of bi- and triantennary complex type N-Glycans. Different lectin molecules may be conjugated to magnetic particles by direct chemical epoxy linkage, or biotin-streptavidin. The lectin-conjugated magnetic particles can be used in purification of glycan molecules after enzymatic digestion reactions and after labeling reactions to remove the excess fluorescent dye or other labeling reagents. In other embodiments, boronic acid has been shown to bind to sugars well and can be used in purification of glycan molecules. The surface of magnetic particles can be modified by coating it with boronic acid moeities to bind sugars. Lectin-coated and/or boronic acid-coated magnetic particles can be used separately or together to purify glycan molecules after digestion, after labeling or just prior to detection of the labeled glycan.

Separation.

The at least one labeled glycan may be separated from different labeled glycan species or from impurities remaining in the post labeling sample by migrating the at least one labeled glycan under the influence of an electric field in a channel. Electrophoresis provides such differential migration as mobility may be dependent upon both size and charge characteristics. In various embodiments, the channel includes a sieving polymer in the separation medium used for the separation of the at least one labeled glycan. The channel may contain a separation medium containing a buffer and additional components, for example, a sieving polymer, as described here, which may be selected to provide electrophoretic force to the at least one labeled glycan and permit a distinct migration time to be detected for each of the at least one labeled glycan species present in the electrophoretic separation. The migration time of the at least one labeled glycan may be moderated by choice of electric field strength, length of channel, polarity, ionic strength of the separation medium amongst other variables.

Buffer.

A buffer composition configured to permit migration of the at least one labeled glycan may be included in the channel when the at least one labeled glycan may be subjected to the influence of an electric field. Any suitable buffer may be used. A buffer for use in CE may have one or more of the following properties: good buffering capacity in the pH range of choice; low absorbance at the wavelength of detection; large, minimally-charged ions, which may be useful to minimize current generation.

Dextran Ladder.

The dextran ladder may include oligomers having an increasing number of glucose molecules, the increasing number going from one glucose molecule to about twenty glucose molecules, or may include a linear oligomer having a plurality of synthesized maltoses, for example. The dextran ladder may be extracted from digested starch. The dextran ladder may further be labeled with any of the detectable labels as described herein, including but not limited to reactive nucleic acids or fluorescent dyes linked to the dextran ladder, such that it may be detectable under the same conditions as that employed to detect the labeled glycan.

Glycan Sequencing:

An exemplary method of determining a glycan sequence may comprise: (a) separating a glycan from a cleaved glycan pool; (b) labeling the glycan with a nucleic acid oligomer to generate a labeled glycan; (c) making a plurality of aliquots of the labeled glycan and treating each aliquot with a distinct enzyme mixture generating an enzyme-treated aliquot with a variable, truncated glycan in each aliquot, wherein each distinct enzyme mixture comprises at least one, different, linkage-specific exoglycosidase enzyme; (d) resolving the plurality of variable, truncated glycans from step (c) by a suitable separation means, to generate a first set of characteristic mobility shift profiles; (e) optionally, sequentially repeating the enzyme treatment of one or more selected, enzyme-treated aliquot(s) of step (c) with a plurality of distinct enzyme mixtures, until the truncated glycan can no longer be digested, wherein each enzyme treatment generates a plurality of characteristic mobility shift profiles; and, (f) determining the glycan sequence by analyzing the sequential and characteristic mobility shift profiles and mapping the profiles to the linkage-specific exoglycosidases used during enzyme digestion, wherein the nucleic acid oligomer comprises: i) an intrinsic charge and a reactive moiety at a first site that enables attachment to the glycan; and ii) optionally, a detectable tag at a second site on the nucleic acid oligomer.

Upon detecting the label, determination can be made as to whether the at least one glycan may be present and upon comparison to known migration times under similar conditions, assignment of identity of the at least one glycan can be made. The migrated charged labeled glycan may be subjected to a second or third, orthogonal methods of detection, such methods including but not limited to Hydrophilic Liquid Chromatography, Mass Spectrometry, Nuclear Magnetic Resonance Spectrometry, or electrochemical detection.

Uses of the Methods.

The labeling species and methods of the present disclosure can be applied to glycans derived from samples obtained from a wide variety of sources including, but not limited to, therapeutic formulations and biological samples. A biological sample may undergo one or more analysis and/or purification steps prior to or after being analyzed according to the present disclosure. To give but a few examples, in some embodiments, a biological sample may be treated with one or more proteases and/or glycosidases (e.g., so that glycans are released); in some embodiments, glycans in a biological sample are labeled with one or more labeling species provided herein. Any of a variety of separation and/or isolation steps may be applied to a biological sample in accordance with the present disclosure.

The labeling species and methods of the present disclosure can be utilized to analyze glycans in any of a variety of states including, for example, free glycans, glycoconjugates (e.g., glycopeptides, glycolipids, proteoglycans, etc.), or cells or cell components, etc.

The labeling species and methods of the present disclosure can be used to significantly expedite one or more stages of process development for the production of a therapeutic or other commercially relevant glycoprotein of interest. Non-limiting examples of such process development stages that can be improved using methods of the present disclosure include cell selection, clonal selection, media optimization, culture conditions, process conditions, and/or purification procedure. Those of ordinary skill in the art will be aware of other process development stages that can be improved.

The methods and labeling species disclosed herein can also be used to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The methods and labeling species disclosed herein can also be utilized to assess glycosylation characteristics of cells and or cell lines that are being considered for production of a particular desired glycoprotein (for example, even before the cells or cell lines have been engineered to produce the glycoprotein, or to produce the glycoprotein at a commercially relevant level).

In some embodiments, a desired glycosylation pattern for a particular target glycoprotein may be known, and the technology described herein allows the monitoring of culture samples to assess progress of the production along a route known to produce the desired glycosylation pattern. For example, where the target glycoprotein may be a therapeutic glycoprotein, for example, having undergone regulatory review in one or more countries, it may often be desirable to monitor cultures to assess the likelihood that they may generate a product with a glycosylation pattern as close to identical with the established glycosylation pattern of the pharmaceutical product as possible, whether or not it is being produced by exactly the same route. As used herein, "close to identical" refers to a glycosylation pattern having at least 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

Whether or not monitoring production of a particular target protein for quality control purposes, the labeling species, compositions, methods and kits of the present disclosure may be utilized, for example, to monitor glycosylation at particular stages of development, or under particular growth conditions.

In some particular embodiments of the present disclosure, the methods and labeling species provided herein can be used to characterize and/or control or compare the quality of therapeutic products. To give but one example, the present methods and labeling species can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the methods and labeling species provided herein can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for example, erythropoietins, blood-clotting factors, etc.), interferons, colony stimulating factors, antibodies, enzymes, and hormones.

In some embodiments, the disclosure provides methods in which glycans from different sources or samples are compared with one another. In certain embodiments, the disclosure provides methods used to monitor the extent and/or type of glycosylation occurring in different cell cultures. In some such examples, multiple samples from the same sourced are obtained over time, so that changes in glycosylation patterns (and particularly in cell surface glycosylation patterns) are monitored. In some embodiments, one of the samples is a reference sample. For example, in certain embodiments, the methods and labeling species provided herein can be used to monitor the extent and/or type of glycosylation occurring in different cell cultures.

In some embodiments, the methods and labeling species disclosed herein can be used to compare glycans from different cell culture samples prepared under conditions that differ in one or more selected parameters (e.g., cell type, culture type, culture conditions, culture time, isolation steps, etc.) but are otherwise identical in order to determine the effects of the single selected parameter on the glycosylation pattern. Among other applications, therefore, use of the labeling species and methods disclosed herein may facilitate determination of the effects of particular parameters on glycosylation patterns in cells.

In some embodiments, glycans from different batches of a glycoprotein of interest (e.g., therapeutic glycoprotein), whether prepared by the same method or by different methods, and whether prepared simultaneously or separately, are compared. In such embodiments, the methods and labeling species provided herein are used to facilitate quality control of glycoprotein preparation. Alternatively or additionally, some such embodiments facilitate monitoring of progress of a particular culture producing a glycoconjugate of interest (e.g., when samples are removed from the culture at different time points and are analyzed and compared to one another). In any of these embodiments, features of the glycan analysis can be recorded, for example in a quality control record. As indicated above, in some embodiments, a comparison is with a historical record of a prior or standard batch and/or with a reference sample of glycoprotein.

In certain embodiments, the methods, labeling species, compositions and kits of the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, the methods and dye compounds of the present disclosure are applied to glycans that are present on the surface of cells. In some such embodiments, the analyzed glycans are substantially free of non-cell-surface glycans. In some such embodiments, the analyzed glycans, when present on the cell surface, are present in the context of one or more cell surface glycoconjugates (e.g., glycoproteins or glycolipids).

In some particular embodiments, cell surface glycans are analyzed in order to assess glycosylation of one or more target glycoproteins of interest, particularly where such target glycoproteins are not cell surface glycoproteins. Such embodiments can allow one to monitor glycosylation of a target glycoprotein without isolating the glycoprotein itself. In certain embodiments, the methods disclosed herein utilize cell-surface glycans as a readout of or proxy for glycan structures on an expressed glycoprotein of interest. In certain embodiments, such methods include, but are not limited to, post process, batch, screening or "in line" measurements of product quality. Such methods can provide for an independent measure of the glycosylation pattern of a produced glycoprotein of interest using a byproduct of the production reaction (e.g., the cells) without requiring the use of destruction of any produced glycoprotein. Furthermore, methods of the present disclosure can avoid the effort required for isolation of product and the potential selection of product glycoforms that may occur during isolation.

In certain embodiments, the methods, labeling species, compositions and kits of the present disclosure are applied to glycans that are secreted from cells. In some such embodiments, the analyzed glycans are produced by cells in the context of a glycoconjugate (e.g., a glycoprotein or glycolipid).

The methods, labeling species, compositions and kits described herein can be used to detect desirable or undesirable glycans, for example to detect or quantify the presence of one or more contaminants in a product, or to detect or quantify the presence of one or more active or desired species.

In various embodiments the methods provided herein can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, the methods facilitate detection of glycans that are present at very low levels in a source (e.g., a biological sample). In such embodiments, it is possible to separate over 10, 20, 30, 40, 50, 60, 70, 80, 90 or 100 glycan components of a mixture.

In some embodiments, the techniques may be combined with one or more other technologies for the detection, analysis, and or isolation of glycans or glycoconjugates.

Compositions.

Kits.

Kits are described for detecting at least one glycan in a sample containing a glycoconjugate, which include at least one glycan-cleaving enzyme; and at least one labeling species for labeling the at least one glycan. A kit can also optionally include instructions for use. In various embodiments, the at least one glycan-cleaving enzyme may be immobilized on a bead. The immobilized glycan-cleaving enzyme may be immobilized on a magnetic bead.

The kit may further include purification beads. The beads may be charcoal beads, or size exclusion beads, or any suitable material. In some embodiments, the purification beads may be magnetic.

In various embodiments, the magnetic purification beads may include surface modifications configured to bind to the at least one glycan. In other embodiments, a kit may include one or more spin columns configured to separate labeled glycans from excess reagents and side products of a glycan cleavage reaction and/or a labeling reaction.

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be purchased and/or delivered to the intended recipient together or separately. For example, a first container may contain an enzyme for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Systems.

A system for detecting at least one glycan in a sample containing a biomolecule or a glycoconjugate, includes a channel comprising a sieving polymer; an anode and a cathode operably connected to the channel, configured to provide an electric field to the channel; and a detector configured to detect a charged labeled glycan, wherein the detector detects ultraviolet absorbance, fluorescence, chemiluminescence, or visible light absorption; further comprising a data processor operably connected to the detector. The system may further comprise a second analytical mode selected from the group consisting of hydrophilic liquid chromatography, mass spectrometry, and UV absorbance, a buffer filled channel comprising sieving polymer; and may include an interface for introducing the sample into the channel through electrokinesis or physical fluid transfer; an anode and a cathode operably connected to the channel, configured to provide an electric field to the channel; and an incident beam module configured for continuous excitation for in-line monitoring; and may include a detector cell configured to detect responses deriving from the charged labeled glycan.

An apparatus for glycan analysis may include: (1) at least one loading well adapted to receive at least one labeled glycan; (2) at least one channel arranged in correspondence with the loading well; and optionally (3) at least one eluting well arranged in correspondence with the channel and adapted to receive a portion of the sample having traversed the channel. In various embodiments, a plurality of loading wells are arranged in correspondence with a plurality of channels, and optionally each of the plurality of channels is arranged in correspondence with a respective eluting well.

Each loading well may be a receptacle in fluid communication through an ion permeable membrane with its respective channel. Each loading wells may have a volume capacity of between about 10 µl and about 500 µl, or of between about 50 µl and about 150 µl, for example. Each eluting well may have a volume capacity of between about 10 µl and about 500 µl, or of between about 50 µl and about 150 µl, for example. The apparatus may further include a reservoir including a buffer solution, the reservoir being in fluid communication through an ion permeable membrane with the loading well. The buffer solution may be any suitable buffer for separating labeled glycans. The apparatus may further include a sample loader configured to load samples in the loading wells.

If a plurality of channels are present, the plurality of channels may be substantially parallel to one another. A channel may have a substantially circular cross-section, or may have a substantially rectangular cross-section, for example. The plurality of channels may be connected structurally to form a channel array unit that may be removable as a whole, and may further include first and second support structures arranged at opposite sides so as to form a single channel array unit. The channel array unit may be configured for a single use and disposable. A channel may be configured for a single use and disposable. A total length of a channel may be between about 10 cm to about 50 cm, about 10 cm to about 30 cm, or may be about 10 cm, for example. In some embodiments, the channel may have a length of less than 10 cm. The channel array may include at least five channels, at least ten channels, or at least twenty channels, for example. A channel may have an internal diameter of between about 150 micrometers and about 250 micrometers, or between about 50 micrometers and about 100 micrometers, or between about 0.1 millimeter and about 2.5 millimeters, or between about 0.5 millimeter and about 1.5 millimeters, for example.

The apparatus may further include an ion permeable membrane 8 arranged between the loading well and the channel. The apparatus may further include at least two electrodes arranged on opposite sides of the channel, and the at least two electrodes may be platinum electrodes and may include a positive electrode arranged between the channel and the eluting well and a negative electrode arranged between the channel and the loading well. The apparatus may further include a power source connected to the at least two electrodes and configured to subject at least part of the channel to an electric field. The electric field may have an intensity of between about 200 V/cm and about 400 V/cm, or of between about 250 V/cm and about 350 V/cm, for example. The apparatus may further include a light source configured to subject at least one region of the channel to electromagnetic radiation, and the light source may be a diode laser, a blue Argon ion laser, or a yellow Krypton ion laser, for example. The electromagnetic radiation may be radiation having a wavelength in the range of about 400-500 nm or in the range of about 500-600 nm, for example. The apparatus may further include a fluorescence detector configured to detect fluorescence emitted from the capillaries, and the fluorescence detector may be a CCD camera or a CMOS camera. The apparatus may further include a bandpass filter arranged between the channel and the CCD camera and configured to allow radiation having a wavelength of about 510 nm to pass. The apparatus may be a bench top apparatus, and may have a largest width, depth, or height that does not exceed about twelve inches.

The apparatus may further include a signal processor configured to process a signal related to fluorescence detected by the fluorescence detector, and the signal processor may be configured to generate an electrophoretogram showing peaks representing individual glycans having migrated through the channel so as to reveal a time point at which each glycan passed across the fluorescence detector before eluting off the end of the channel. The apparatus may further include a computer in communication with the fluorescence detector, the computer being configured to process a signal related to fluorescence detected by the fluorescence detector. The computer may be configured to generate an electrophoretogram showing peaks representing individual glycans having migrated through the channel so as to reveal a time point at which each glycan passed across the fluorescence detector before eluting off the end of the channel. The computer may include or be configured to access an empirically-derived database of glycan migration times, and may include or be configured to access and run a computer program product configured to consult the empirically-derived database of glycan migration times to compare migration times obtained by running an experiment with the apparatus to identify individual glycans having migrated through the channel during the experiment.

Library.

According to an exemplary embodiment, there may be provided an array of channels for glycan analysis, including: (1) at least five channels arranged substantially parallel to one another, each of the channels including buffer suitable for migrating glycans, and further where the buffer inside each of the channels contains sieving polymer, and (2) first and second support structures arranged at opposite sides of the at least five channels such that the at least five channels form a single unit, i.e. an array.

According to an exemplary embodiment, there may be provided a library of information elements stored in a medium readable by a computer, including: (1) a plurality of empirically-derived channel migration times corresponding to a plurality of individual charged, fluorescently-labeled glycans having migrated through a channel where the channel contains sieving polymer, upon placing the channel under the influence of an electric field; and (2) a migration time corresponding to a dextran ladder. The dextran ladder may act as an internal reference or may be run in a separate electrophoretic separation before or after the glycan may be subjected to electrophoresis.

The empirically-derived migration times corresponding to a plurality of individual glycans may include empirically-derived migration times corresponding to a plurality of polysaccharides, or a plurality of oligosaccharides, or a plurality of proteoglycans, or a plurality of glycoproteins, or a plurality of glycolipids, or a plurality of O-linked glycans, or a plurality of N-linked glycans, for example. The library may further include a plurality of empirically-derived electrophoretogram showing peaks representing individual glycans, and may further include an empirically-derived electrophoretogram showing peaks including at least one peak corresponding to a dextran ladder.

In some embodiments, methods for generating a glycan database, may comprise: obtaining a plurality of empirically-derived migration times corresponding to a plurality of individual charged, fluorescently-labeled glycans having migrated through a channel under the influence of an electric field, wherein the channel comprises sieving polymer; and arranging the collected plurality of empirically-derived migration times in correspondence with an identification information of each of the plurality of individual charged, fluorescently-labeled glycans into a database configured to be accessible by a computer.

Additional Analytical Components.

The system may be connected to additional components to provide a second analytical measurement, differing from the electrophoretic separation described above. The second analytical measurement may be selected from mass spectrometry, UV absorbance, Hydrophilic Liquid Chromatography, nuclear magnetic resonance, or other analysis methods offering differing or orthogonal analysis modes. The second analytical measurement could include a second electrophoretic separation under differing buffer or electric field conditions, such that differing migration forces may effect a different migration behavior of the glycan. The output of the first electrophoretic separation may be connected operably with the input of the second analytical instrument or the glycan separated in the first electrophoretic separation may be transferred manually to the second analytical instrumentation.

Those skilled in the art understand that the detection techniques employed are generally not limiting. Rather, a wide variety of detection means are within the scope of the disclosed methods and kits, provided that they allow the presence or absence of an amplicon to be determined. While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations may be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

EXAMPLES

Example 1

In an illustrative embodiment for the use of compounds (described above) that were synthesized using the methods described above, a family of reactive, fluorescently tagged oligonucleotides were prepared and conjugated to hydrolyzed dextran ladders, and to purified hexose polymers. The resulting glycoconjugates were resolved by capillary gel electrophoresis (CE) using standard DNA sequencing equipment (i.e., AB 3130xl/3500xl, POP7 polymer, 50 cm capillary and 488/505 nm laser excitation). Baseline resolution was achieved for linear dextran polymers, and the spacing between successive glucose units was constant and highly linear beyond 40 glucose units. In addition to remaining constant when driven by a given charge, the unit spacing between successive glucose units decreased as the length of the oligonucleotide increased (or) as the negative charge of the reactive NA probe increased. This showed that the migration of glycans can be tuned (and this principle may also be applied to other biomolecules) by varying the number of phosphodiester linkages within the reactive nucleic acid. In this exemplary illustration, a negative charge of -7 did not overwhelm the ability of the polymer system to baseline resolve single glucose differences in linear glycans. These findings establish a facile technology by which different fluorphores can be mixed and matched with reactive chemistries to build variably charged reactive fluorphores (VCRF's) for use as mobility tags.

Materials and Methods:

Reactive Nucleic Acid Probes:

The following series of oligonucleotides bearing 5' fluorescent dyes and amine terminated 3' were prepared by solid phase synthesis: (5'-FAM-TGACT-NH2-3') (5'-FAM-TTTT-NH2-3') (5'-FAM-TTT-NH2-3') (5'-FAM-TT-NH2-3') (5'-FAM-T-NH2-3') (5'-VIC-TTTTT-NH2-3') (5'-VIC-TTTTT-NH2-3') (5'-VIC-TTTT-NH2-3') (5'-VIC-TTT-NH2-3') (5'-VIC-TT-NH2-3') (5'-VIC-T-NH2-3') (5'-HEX-TTT-NH2-3') (5'-HEX-TT-NH2-3') (5'-HEX-T-NH2-3') (5'-ROX-TTT-NH2-3') (5'-ROX-TT-NH2-3') (5'-ROX-T-NH2-3'). Oligonucleotide probes bearing 3' fluorescent dyes and functionalized 5' with oximes or hydrazides were generated by solid phase synthesis.

(5'-Oxime-TTTTT-FAM-3') (5'-Oxime-TTTT-FAM-3') (5'-Oxime-TTT-FAM-3') (5'-Oxime-TT-FAM-3') (5'-Hydrazide-TTTTT-FAM-3') (5'-Hydrazide-TTTT-FAM-3') (5'-Hydrazide-TTT-FAM-3') (5'-Hydrazide-TT-FAM-3') (5'-Hydrazide-T-FAM-3') (5'-Hydrazide-TTTTT-TAMRA-3') (5'-Hydrazide-TTTT-TAMRA-3') (5'-Hydrazide-TTT-TAMRA-3') (5'-Hydrazide-TT-TAMRA-3'). All VCRF's were HPLC purified over C18 column in a volatile buffer system (ref) and quantified by UV absorbance. Post synthesis derivatization with hydrazine, protected hydrazine or hydrazide functionalities was accomplished through reactions with succinimide esters SHNH, SANH and SHTH under aqueous conditions (pH 9) and HPLC purified by C18 reverse phase and ion exchange.

Reverse Phase HPLC:

Column: Spheri-5 RP-C18, 5 μm particle size, 220×4.6 mm (PE Applied Biosystems); generic gradient: 95% triethylammonium acetate (TEAA, 0.1M) to 40% acetonitrile: 60% TEAA at 1.5 ml/min over 20 min followed by 40% to 100% acetonitrlie at 1.5 mL/min over 5 min. In individual purifications, different variants of this gradient were used.

Anion Exchange HPLC:

Column: Aquapore™ AX-300, 7 μm particle size, 220× 4.6 mm (PE Applied Biosystems); generic gradient: 20% acetonitrile: 80% triethylammonium bicarbonate (TEAB, 0.1M) to 20% acetonitrile: 80% TEAB (1.5 M) at 1.5 ml/min over 20 min, followed by isocratic elution. In individual purifications, different variants of this gradient were used.

Detection:

UV/VIS: 260, 290 nm and 500 nm or 560 etc. depending on the absorption of the dye.

Dextran Labeling:

Dextran ladders derived from acid hydrolyzed corn starch were purchased from Sigma or obtained as gift from Grain Processing Corporation, Muscatine, Iowa Purified maltodextrins of defined length (maltopentaose and maltohexaose) were purchased from Sigma. Labeling reactions were carried out for 1-5 hours in an Eppendorf themomixer at 37-65° C. with shaking. Stock formulations of dextran ladders (1 ug/mL) or purified maltodextins [0.1-1 mM] were prepared in dH$_2$O and stored at −20 C. Labeling reaction were assembled with 1-2 ug of dextran ladder or 0.1-1 nmole maltodextrin, 10-200 uM reactive dye conjugate, in 10-20 mM acetic acid.

In addition to carbohydrate analysis, the invention discloses the use of these dye conjugates as fluorescent motor probes for use in propelling neutral or high drag biopolymers such proteins, peptides, lipids, vesicles, etc., through liquid hydrogels, capillary gel polymer systems, or any charge gradient or charge differential field where separation of such charged species may be possible. The invention also discloses that when the variably charged reactive fluorphores (VCRF's) are linked to immunoglobins, receptors or affinity tags, the highly charged versions of these fluorescent oligomers could also drive selective the migration of whole living cells, dead cells, microorganisms, vesicles, viruses, etc. across a charge differential field.

Labeling glycans with multiple dyes of superior sensitivity described in throughout this application, and in PCT application LT00887 PCT, entitled "Hydrazinyl and Aminooxy Compounds and Their Methods of Use", filed on Dec. 3, 2015, which claims benefit to U.S. Provisional Application LT00887PRO, filed on Dec. 3, 2014, the disclosure of which is each hereby incorporated by reference in its entirety for all purposes, enable a simpler sample prep for glycan analysis, and a more efficient workflow. The sensitive dyes also provided reproducible, overlapping glycan peaks in assays (for example, an overlay of 288 injections produced completely overlapping glycan peaks). The superior dye sensitivity also requires lower glycoprotein (sample) input. Further glycans can be labeled with the nucleic acid oligomers and mobility modifying tags described in the application herein, to further increase the specificity, sensitivity and reproducibility of glycan detection.

Sample handling is further simplified by using magnetic bead based sample prep. Thus, in a typical sample preparation, the hands-on-time can be reduced, for example, to <3 hrs for 96 samples, while current methods can take up to 24 hours for sample prep. In certain aspects, sample prep & data for 96 samples can be collected within 7-9 hours, depending on the dye type used in labeling. A typical, exemplary glycan analysis workflow is: enzymatic glycan release (1 hour), magnetic bead glycan purification (30 min), glycan dye labeling (2 hour), optional (depending on choice of dye), excess dye removal (30 min), CE analysis (3 hour).

Some additional advantages seen due to the use of the improved dyes and modifiers described herein are: lesser number of pipetting steps during sample prep since steps like purification of excess dye after labeling are unnecessary when certain dyes are used in labeling, elimination of the use of toxic sodium cyanoborohydride from the CE analysis method, elimination of vacuum centrifugation steps. Here are some glycan species that were resolved distinctly using the methods described: sialyated glycans, glycan structural isomers, fucose species, high mannose species, and others.

What is claimed is:

1. A method of labeling a glycan on a biomolecule, comprising:
    (a) cleaving the glycan from the biomolecule generating a cleaved glycan; and
    (b) labeling the cleaved glycan with a nucleic acid oligomer to form a nucleic acid-charged glycan;
    wherein the nucleic acid oligomer comprises:
    i) a first site comprising an intrinsic charge and a reactive moiety, wherein the reactive moiety enables attachment of the nucleic acid oligomer to the glycan; and
    ii) a second site consisting of at least one detectable tag selected from:

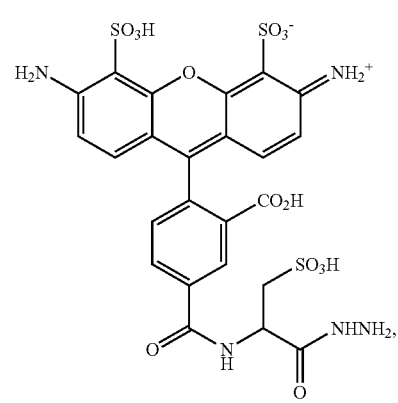

Compound 1

-continued

Compound 2

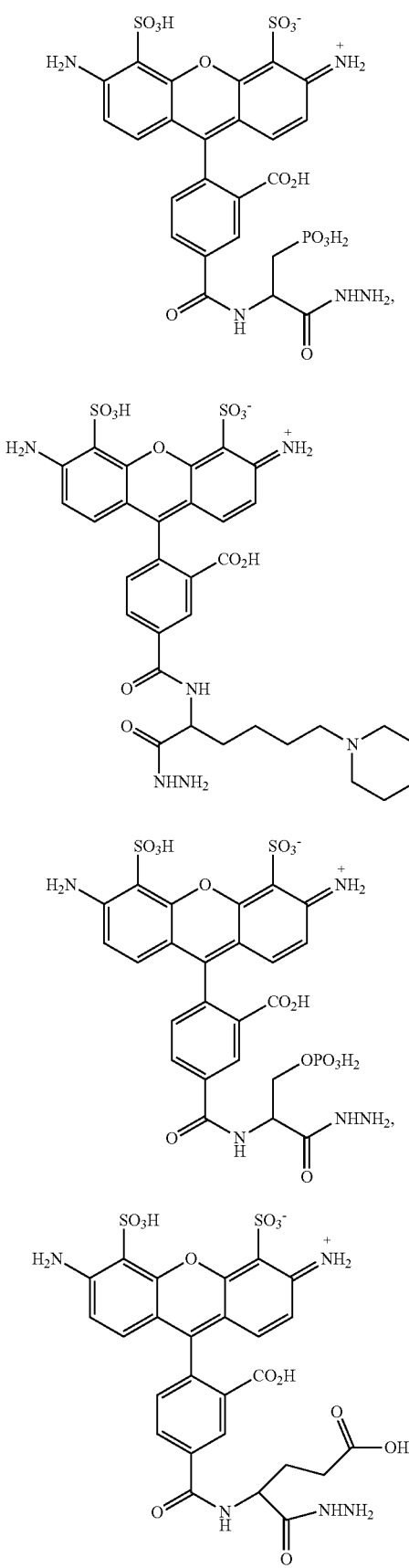

Compound 3

Compound 4

Compound 5

-continued

Compound 6

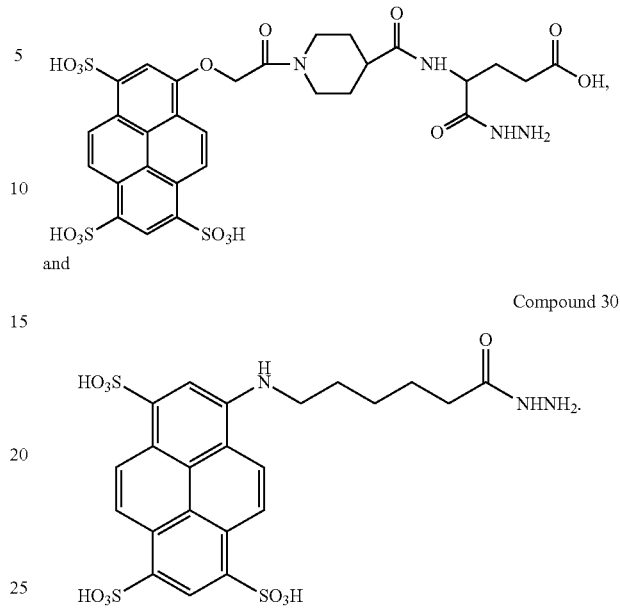

and

Compound 30

2. The method of labeling the glycan of claim 1, further comprising detecting the nucleic acid-charged glycan.

3. The method of labeling a glycan in claim 2, wherein said detection is selected from the group consisting of UV absorbance, fluorescence, visible light, chemiluminescence, conductance and an electrical signal.

4. The method of labeling a glycan of claim 1 wherein, the cleaved glycan of step (a) is separated in a charge differential field to generate a charged glycan, or wherein, the nucleic acid-charged glycan of step (b) is separated in a charge differential field and is identified by a hybridization step.

5. The method of labeling a glycan of claim 4 wherein, the charge differential field comprises an electric field, a magnetic field, a salt gradient, or, wherein said charged glycan has a negative charge.

6. The method of labeling a glycan of claim 1, wherein said biomolecule is selected from the group consisting of a glycoprotein, a glycolipid, a proteoglycan, a phosphoprotein, a glycosaminoglycan, a phospholipid-protein containing a glycan core, a synthetic glycan, a native glycan, a derivatized glycan, or, wherein said nucleic acid oligomer comprises 1 to 20 nucleotides.

7. The method of labeling a glycan of claim 6, wherein said nucleic acid oligomer is selected from the group consisting of 1 to 5 nucleotides, 1 to 8 nucleotides, 1 to 10 nucleotides, 1 to 15 nucleotides and 1 to 2 nucleotides.

8. The method of labeling a glycan of claim 1, wherein said nucleic acid oligomer comprises a deoxyribonucleic acid or analogs thereof, a ribonucleic acid or analogs thereof, a locked nucleic acid (LNA) or analogs thereof, a protein nucleic acid (PNA), or a nucleic acid with a phosphorothionate linkage.

9. The method of labeling a glycan of claim 1, wherein the first site comprises at least one of a nucleotide base, a 2' sugar, a 3' sugar, or a 5' sugar.

10. A method for detecting a glycan on a biomolecule, comprising:
(a) cleaving the glycan from the biomolecule generating a cleaved glycan;

(b) labeling the cleaved glycan with a mobility modifier to form a charged glycan; and (c) detecting the charged glycan, wherein the mobility modifier comprises:

i) a first site comprising an intrinsic charge and a reactive moiety, wherein the reactive moiety enables attachment of the nucleic acid oligomer to the glycan; and ii) a second site consisting of at least one detectable tag selected from:

Compound 1

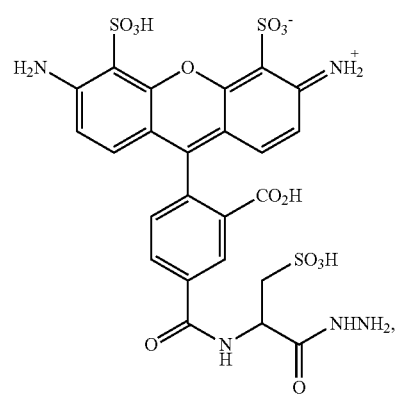

Compound 2

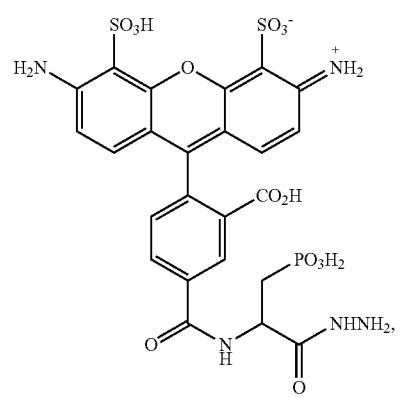

Compound 3

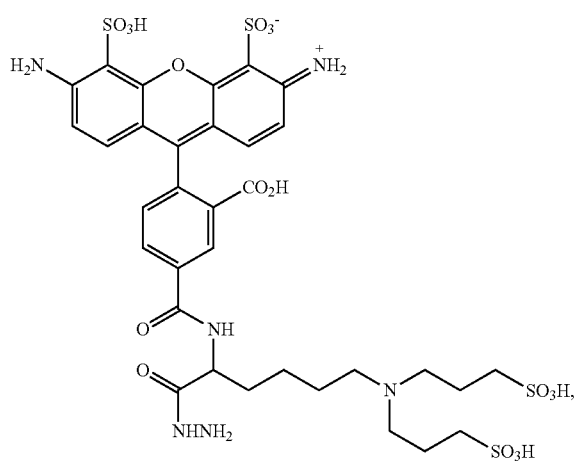

Compound 4

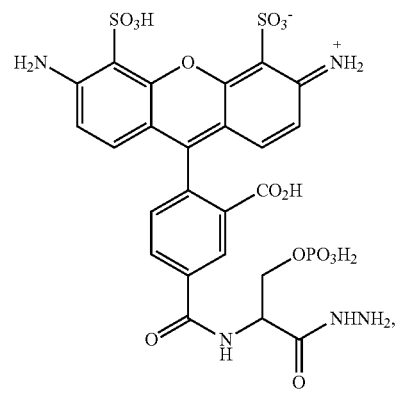

Compound 5

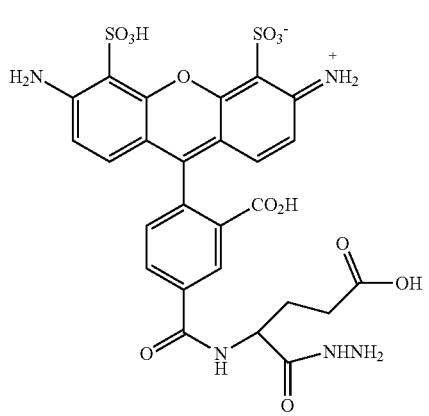

Compound 6

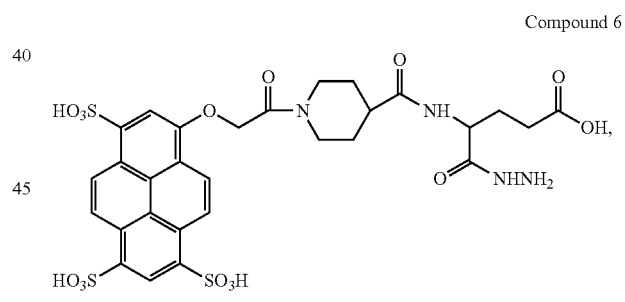

and

Compound 30

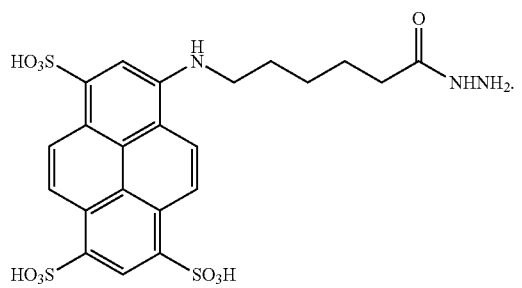

11. A method of determining a glycan sequence, comprising:
   (a) separating a glycan from a cleaved glycan pool;
   (b) labeling the glycan with a nucleic acid oligomer to generate a nucleic acid labeled glycan;
   (c) making a plurality of aliquots of the nucleic acid labeled glycan and treating each aliquot with a distinct enzyme mixture generating an enzyme-treated aliquot with a variable, truncated glycan in each aliquot, wherein each distinct enzyme mixture comprises at least one, different, linkage-specific exoglycosidase enzyme;
   (d) resolving the plurality of variable, truncated glycans from step (c) by a suitable separation means, to generate a first set of characteristic mobility shift profiles;
   (e) optionally, sequentially repeating the enzyme treatment of one or more selected, enzyme-treated aliquot (s) of step (c) with a plurality of distinct enzyme mixtures, until the truncated glycan can no longer be digested, wherein each enzyme treatment generates a plurality of characteristic mobility shift profiles; and
   (f) determining the glycan sequence by analyzing the sequential and characteristic mobility shift profiles and mapping the profiles to the linkage-specific exoglycosidases used during enzyme digestion,
   wherein the nucleic acid oligomer comprises:
   i) an intrinsic charge and a reactive moiety at a first site that enables attachment to the glycan; and
   ii) a second site consisting of at least one detectable tag selected from:

Compound 1

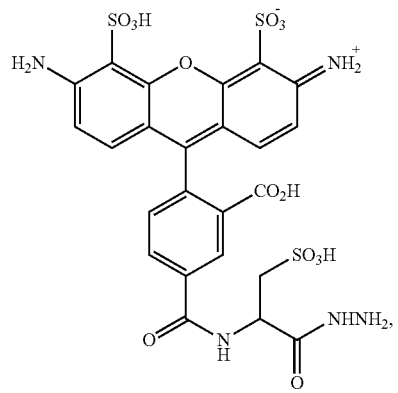

Compound 2

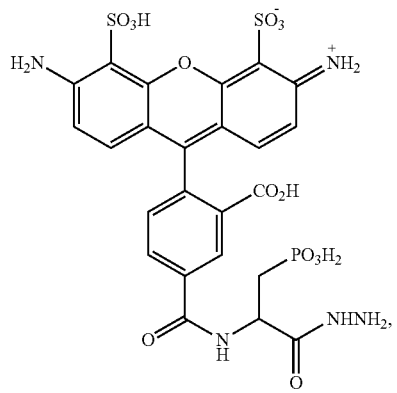

-continued

Compound 3

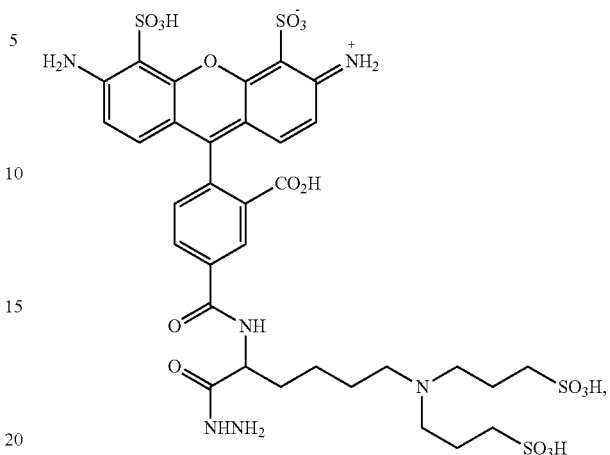

Compound 4

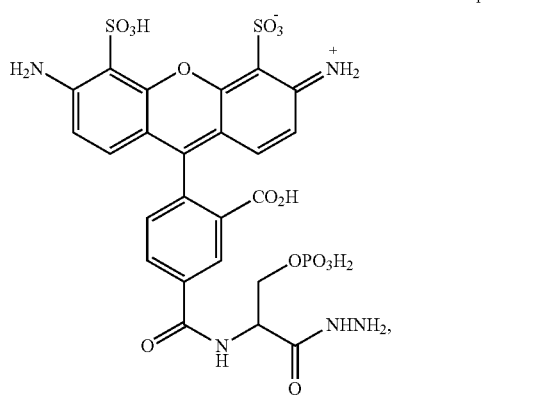

Compound 5

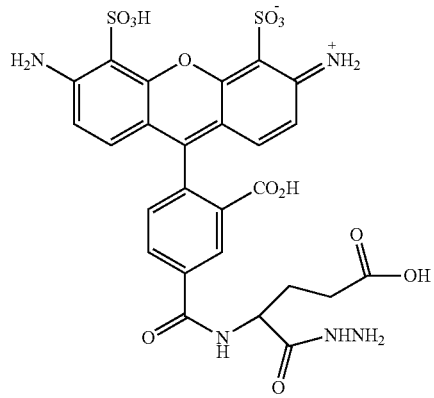

Compound 6

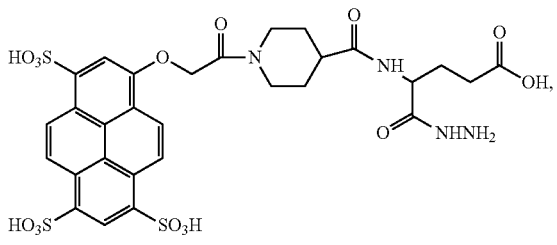

-continued
and
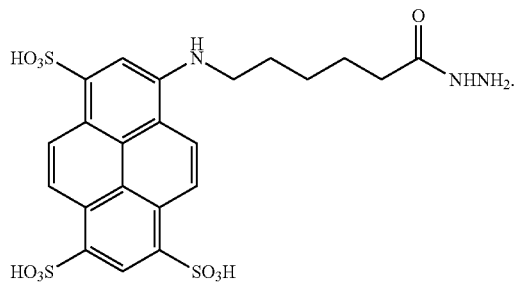
Compound 30